United States Patent
Kaneko

(10) Patent No.: US 9,958,418 B2
(45) Date of Patent: May 1, 2018

(54) TOUCH DETECTION DEVICE USED IN WATER HANDLING EQUIPMENT, AND FAUCET APPARATUS INCLUDING THE SAME

(71) Applicant: TOTO LTD., Kitakyushu-shi, Fukuoka (JP)

(72) Inventor: Yoshiyuki Kaneko, Kitakyushu (JP)

(73) Assignee: TOTO LTD., Kitakyushu-Shi, Fukuoka (JP)

(*) Notice: Subject to any disclaimer, the term of this patent is extended or adjusted under 35 U.S.C. 154(b) by 0 days. days.

(21) Appl. No.: 15/189,262

(22) Filed: Jun. 22, 2016

(65) Prior Publication Data

US 2017/0003253 A1    Jan. 5, 2017

(30) Foreign Application Priority Data

Jul. 1, 2015 (JP) .................................. 2015-132444
Apr. 28, 2016 (JP) .................................. 2016-090605

(51) Int. Cl.
*G01N 9/24* (2006.01)
*G01N 29/12* (2006.01)
(Continued)

(52) U.S. Cl.
CPC ............. *G01N 29/12* (2013.01); *G01H 11/08* (2013.01); *H03K 17/96* (2013.01); *H03K 17/964* (2013.01);
(Continued)

(58) Field of Classification Search
CPC ...... E03C 1/055; E03C 1/05; Y10T 137/9464; Y10T 137/0318; H03K 17/96;
(Continued)

(56) References Cited

U.S. PATENT DOCUMENTS 7,265,746 B2 * 9/2007 Knowles ............... G06F 3/0436
                                                    345/156
7,337,085 B2 * 2/2008 Soss ....................... G06F 3/0414
                                                    702/104
(Continued)

FOREIGN PATENT DOCUMENTS

DE   10 2013 003 821 A1   9/2014
EP   1 330 777             7/2003
(Continued)

OTHER PUBLICATIONS

European Search Report issued in European Patent Application No. 16176692.8 dated Nov. 9, 2016.
(Continued)

*Primary Examiner* — Jonathan Dunlap
(74) *Attorney, Agent, or Firm* — Baker & Hostetler LLP

(57) ABSTRACT

A touch detection device capable of operation by a light touch, and of preventing false operations even when used in water handling equipment includes a sensing portion for sensing contact by a target object; a vibration excitation element attached to this sensing portion, a drive circuit for exciting vibration in the sensing portion, and a contact determining circuit for determining whether a target object is contacting a sensing portion based on vibration of the sensing portion after stopping the application of an AC voltage to the vibration excitation element by this drive circuit.

16 Claims, 33 Drawing Sheets

(51) Int. Cl.
*H03K 17/96* (2006.01)
*G01H 11/08* (2006.01)
*E03C 1/05* (2006.01)
*F21V 33/00* (2006.01)
*G01L 1/14* (2006.01)
*G06F 3/043* (2006.01)

(52) U.S. Cl.
CPC .............. *E03C 1/05* (2013.01); *E03C 1/055* (2013.01); *F21V 33/004* (2013.01); *G01L 1/14* (2013.01); *G06F 3/0436* (2013.01); *H03K 2217/96003* (2013.01); *Y10T 137/0318* (2015.04); *Y10T 137/9464* (2015.04)

(58) Field of Classification Search
CPC ....... H03K 17/964; F21V 33/004; G01L 1/14; G06F 3/0436
USPC ..... 251/129.04, 129.03; 137/551, 78.1, 801; 73/586, 599, 602
See application file for complete search history.

(56) References Cited

U.S. PATENT DOCUMENTS

| | | | | |
|---|---|---|---|---|
| 7,698,084 | B2* | 4/2010 | Soss | G06F 3/0414 345/173 |
| 8,028,355 | B2* | 10/2011 | Reeder | A46B 7/04 4/623 |
| 8,090,497 | B2* | 1/2012 | Ando | H03K 17/9622 200/600 |
| 8,278,941 | B2* | 10/2012 | Kroh | A61B 5/0031 324/633 |
| 8,939,429 | B2* | 1/2015 | Sawaski | E03C 1/057 251/129.04 |
| 9,243,391 | B2* | 1/2016 | Jonte | E03C 1/05 |
| 9,243,392 | B2* | 1/2016 | Marty | E03C 1/057 |
| 9,417,730 | B2* | 8/2016 | Shin | G06F 3/0418 |
| 2004/0246239 | A1 | 12/2004 | Knowles et al. | |
| 2006/0293864 | A1* | 12/2006 | Soss | G06F 3/0418 702/104 |
| 2007/0069168 | A1* | 3/2007 | Jonte | E03C 1/057 251/129.03 |
| 2007/0069169 | A1* | 3/2007 | Lin | E03C 1/0404 251/129.04 |
| 2008/0140282 | A1* | 6/2008 | Ando | H03K 17/9622 701/36 |
| 2008/0167832 | A1* | 7/2008 | Soss | G06F 3/0418 702/104 |
| 2008/0271238 | A1* | 11/2008 | Reeder | A46B 7/04 4/597 |
| 2009/0273353 | A1* | 11/2009 | Kroh | A61B 5/0031 324/655 |
| 2013/0248617 | A1* | 9/2013 | Sawaski | E03C 1/057 239/73 |
| 2014/0000733 | A1* | 1/2014 | Jonte | E03C 1/05 137/552 |
| 2015/0013064 | A1* | 1/2015 | Marty | E03C 1/057 4/668 |
| 2015/0062042 | A1* | 3/2015 | Shin | G06F 3/0418 345/173 |
| 2015/0247307 | A1* | 9/2015 | Reeder | E03C 1/055 4/601 |
| 2015/0253935 | A1* | 9/2015 | Toda | H03K 17/964 345/174 |
| 2015/0358740 | A1* | 12/2015 | Tsai | G01N 29/36 73/632 |
| 2016/0032571 | A1* | 2/2016 | Jepson | G05D 7/0635 137/551 |
| 2016/0177551 | A1* | 6/2016 | Li | E03C 1/057 137/78.1 |

FOREIGN PATENT DOCUMENTS

| | | |
|---|---|---|
| EP | 1 966 892 | 9/2008 |
| WO | 02/35460 A1 | 5/2002 |
| WO | 2007/071516 A1 | 6/2007 |

OTHER PUBLICATIONS

Singapore Search Report issued in Singapore Patent Application No. 10201605239Y dated Nov. 9, 2016.
Proakis J G: "Digital Communications, Passage", Jan. 1, 1995, Digital Communications; McGraw Hill, New York, pp. 39-41,58, XP002289026, ISBN: 978-0-07-113814-7.
European Search Report issued in European Patent Application No. 16 176 692.8 dated Jan. 23, 2018.

* cited by examiner

TOUCH DETECTION DEVICE USED IN WATER HANDLING EQUIPMENT, AND FAUCET APPARATUS INCLUDING THE SAME

TECHNICAL FIELD

The present invention pertains to a touch detection device, and more particularly to a touch detection device used for water handling equipment, and a faucet apparatus comprising same.

BACKGROUND ART

Water handling equipment capable of sensing user operations using a switch or sensor and switching between spouting or shutting off water, or changing the form of water spouting, based on the sensed operation, are starting to be widely adopted. Such faucets or other water handling equipment used for water handling in kitchens, sinks, toilets, bathrooms, and the like are used in environments where water leakage can easily occur, where usage frequency is extremely high, and long durability is expected. Switches or sensors used to sense operations therefore preferably do not include mechanical electrical contacts.

Optoelectric sensors used in automatic faucets and the like have the advantage of touch-free operation, but have slow response and are difficult to use, as well as having poor design characteristics due to their prominent sensor portions. An additional problem is false operations of the optoelectrical sensors due to water or bubbles adhering to the sensor portion.

In addition, while it is possible to operate static-electric sensors with an extremely light touch, false operation is unavoidable in environments where water leaks can easily occur, making these difficult to use for water handling equipment.

Here, a piezo-electric switch is disclosed in Japanese Published Unexamined Patent Application 54-153284 (Patent Document 1). This piezo-electric switch utilizes a piezo-electric element, and is able to sense a user's pressing operation without use of a mechanical electrical contact.

Japanese Published Patent S. 58-40803 (Patent Document 2) discloses a non-contacting pushbutton switch circuit. In this pushbutton switch, as well, a piezo-electric element is used to detect a user pressing operation without use of a mechanical electrical contact.

PRIOR ART REFERENCES

Patent Documents

Patent Document 1
    Japanese Published Unexamined Patent Application 54-153284
Patent Document 2
    Japanese Published Patent S. 58-40803

SUMMARY OF THE INVENTION

Problems to be Resolved by the Invention

However, in the piezo-electric switch set forth in Japanese Published Unexamined Patent Application 54-153284 (Patent Document 1), pressure is applied to the piezo-electric element causing it to elastically deform, and the switch operation is sensed using the electrical charge produced by this elastic deformation, creating the problem that a relatively large operating force is required to operate the switch, and operation is not possible with a light touch.

In the non-contacting pushbutton switch circuit set forth in Japanese Published Patent S. 58-40803, a piezo-electric element is built into an oscillator circuit; applying a pushing force to this piezo-electric element changes electrical characteristics such as the impedance of the piezo-electric element, reducing or stopping the vibration, which can be used to detect a user pressing operation. In this non-contacting pushbutton switch, electrical characteristics change with even a tiny pressure force on the piezo-electric element, changing the vibration state of the vibrating circuit into which the piezo-electric element is built, so operation can be sensed with even a light touch. However because the vibrating state of the vibrating circuit is extremely sensitive to circuit constants, when the piezo-electric for sensing operation is placed in a location separated from the vibration circuit, the problem arises that the vibration state can become unstable, causing false sensing.

For example, if a piezo-electric element built into a vibrating circuit is disposed by itself close to the spout opening of a faucet apparatus and the other parts of the vibrating circuit (the vibrating circuit main body) are disposed on the underside of a counter board on which a faucet apparatus is installed, the lead line connecting the piezo-electric element and the vibrating circuit main body will be relatively long. As a result, the inductance and stray capacitance of this lead line may destabilize the vibrating circuit operation, causing false operations. To prevent such false operations requires that the piezo-electric element be placed close to the vibrating circuit main unit. In this case, because the operating portion is disposed close to the spout opening of the faucet apparatus, the entire vibrating circuit must be built-in close to the spout opening, and freedom of design for the faucet apparatus is greatly restricted.

Therefore the present invention has to the object of providing a touch detection device and water handling apparatus comprising same, capable of operation with a light touch, and of preventing false operations even when used in water handling equipment.

Means for Resolving Problems

In order to resolve the above-described problems, the present invention is a touch detection device used in water handling equipment, comprising: a sensing portion for sensing contact with a target object; a vibration excitation element attached to the sensing portion; a drive circuit for exciting a vibration in the sensing portion by intermittently applying an AC voltage at a predetermined frequency to the vibration excitation element; and a contact determination circuit for determining whether the target object has contacted the sensing portion based on vibration of the sensing portion after application of the AC voltage to the vibration excitation element by the drive circuit.

In the invention thus constituted, an AC (alternating current) voltage at a predetermined frequency is applied intermittently to a vibration excitation element by a drive circuit, and vibration is excited in the sensing portion, to which the vibration excitation element is attached. The contact determination circuit determines whether the target object has contacted the sensing portion based on vibration of the sensing portion after stopping the application of an AC voltage to the vibration excitation element.

In the invention thus constituted, determination of contact by a target object with the sensing portion is made based on vibration of the sensing portion after an AC voltage has been applied, therefore since a change in vibration of the sensing portion is induced by even a light "touch" to the sensing portion, the "touch" can be reliably sensed. Also, since the vibration excitation element is attached so as to induce vibration of the sensing portion, circuits will not become unstable or subject to false operations even if the vibration excitation element is disposed in a location removed from the drive circuit or the contact determination circuit, etc. This enables the drive circuit or contact determination circuit, etc, to be freely placed, thus allowing for the configuration of water handling equipment with high design characteristics.

In the present invention, preferably, the vibration excitation element comprises a piezo-electric element, and the contact determination circuit determines whether the target object has contacted the sensing portion based on an output signal from the vibration excitation element detected after stopping of the application of the AC voltage to the vibration excitation element.

In the invention thus constituted, the vibration excitation element comprises a piezo-electric element, therefore the vibration excitation element can be constituted by a simple structure. Since the contact determination circuit determines contact by a target object with the sensing portion based on the output signal from the vibration excitation element, which is a piezo-electric element, vibration in the sensing portion can be detected without providing separate elements or devices for detecting the vibration of the sensing portion, and the constitution of the touch detection device can be simplified.

In the present invention, preferably, the vibration excitation element comprises an input terminal to which the AC voltage is applied by the drive circuit, the output signal from the vibration excitation element is obtained from the input terminal of the vibration excitation element, and the output of the drive circuit becomes high impedance after application of the AC voltage stops.

In the invention thus constituted, the output signal is obtained from the input terminal, which applies an AC voltage to the vibration excitation element, therefore the wiring for applying the AC voltage and at least a part of the wiring for obtaining an output signal can be shared, permitting the signal line wiring to be simplified. Since the output of the drive circuit goes to high impedance after application of the AC voltage is stopped, a fully accurate output signal can be obtained even when the impedance of the output signal from the vibration excitation element is high.

In the present invention, preferably, the contact determination circuit is configured to determine whether or not the target object has contacted the sensing portion based on a vibration energy of the sensing portion detected after the stopping of the application of the AC voltage by the drive circuit, and the contact determination circuit determines that the target object has made contact when the detected vibration energy is at or below a predetermined threshold value.

In the invention thus constituted, the contact determination circuit detects touching based on the vibration energy of the sensing portion after stopping the application of AC voltage, therefore even a tiny attenuation of vibration caused by touch with a hand, etc. can be captured, so a high sensitivity touch detection device can be configured.

In the present invention, preferably, the contact determination circuit is configured to determine whether or not the target object has contacted the sensing portion based on a vibration amplitude of the sensing portion, and the contact determination circuit determines that the target object has made contact when the time for the vibration amplitude to attenuate to a predetermined amplitude or less, is a predetermined time or less.

In the invention thus constituted, the contact determination circuit detects a touch based on the time until the vibration amplitude attenuates to a predetermined amplitude or below, therefore vibration attenuation can be detected with a simple circuit, and the cost of the touch detection device can be constrained.

In the present invention, preferably, the contact determination circuit is configured to determine whether or not the target object has contacted the sensing portion based on a vibration amplitude of the sensing portion, and the contact determination circuit determines that the target object has made contact when the vibration amplitude detected after elapse of a predetermined time following the end of application of the AC voltage by the drive circuit, attenuates to a predetermined amplitude or below.

In the invention thus constituted, the contact determination circuit detects a touch based on the vibration amplitude after elapse of a predetermined time following the end of application of an AC voltage, therefore vibration attenuation can be detected with a simple circuit, and the cost of the touch detection device can be constrained.

In the present invention, preferably, the contact determination circuit comprises an anomaly sensing circuit for preventing false sensing, and the anomaly sensing circuit senses an anomaly based on the output signal from the vibration excitation element detected during application of the AC voltage to the vibration excitation element.

In the invention thus constituted, the anomaly sensing circuit senses anomalies based on output signals during application of an AC voltage to the vibration excitation element, therefore anomalies can be sensed without complicating the touch detection step, and false sensing can be constrained.

In the present invention, preferably, the anomaly sensing circuit senses the anomaly when the amplitude of the output signal detected during application of the AC voltage is larger than the amplitude in normal operations, and the contact determination circuit does not determine the contact of the target object when the anomaly has been sensed.

In the invention thus constituted, the anomaly sensing circuit senses an anomaly based on the amplitude of the output signal when an AC voltage is being applied, and does not sense contact by the target object when an anomaly is sensed, therefore the occurrence of anomalies can be sensed using simple signal processing even if water droplets or the like are adhered to the sensing portion, and false operations due to false sensing can be prevented.

In the present invention, preferably, during application of the AC voltage to the vibration excitation element, the anomaly sensing circuit senses anomaly when the amplitude of the output signal exceeds a predetermined level, and the contact determination circuit does not determine the contact of the target object when the anomaly has been sensed.

In the invention thus constituted, the anomaly sensing circuit senses anomalies based on fluctuations in the amplitude of an output signal when an AC voltage is being applied, therefore anomaly occurrences can be reliably sensed, and false operations caused by false sensing can be avoided.

The present invention preferably further includes a contact determination confirming circuit, wherein after the determination has first been made by the contact determination circuit that the target object has made contact, the contact determination confirming circuit performs a contact determination confirming operation to further reduce the possibility of false sensing.

In the invention thus constituted the contact determination confirming circuit performs a contact determination confirming operation after target object contact has first been determined by the contact determination circuit, therefore false sensing can be more reliably prevented. The contact determination confirming operation is performed after a determination is first made by the contact determination circuit of target object contact, so unnecessary contact determination confirming operations can be avoided, under no risk of false sensing.

In the present invention, preferably, the contact determination confirming circuit performs the contact determination confirming operation, in which the AC voltage to the vibration excitation element is applied for a predetermined confirmation period longer than the normal period of application of the AC voltage, and the determination of contact by the contact determination circuit is confirmed based on the output signal from the vibration excitation element detected during the confirmation period.

In the invention thus constituted, in the contact determination confirming operation an AC voltage is applied to the vibration excitation element for a predetermined confirmation period longer than normal, so anomalies occurring while the AC voltage is being applied can be more reliably detected.

The present invention preferably further includes a frequency adjustment circuit for adjusting the frequency of the AC voltage applied to the vibration excitation element; wherein the frequency adjustment circuit adjusts the frequency of the AC voltage to a resonant frequency of the sensing portion, to which the vibration excitation element is attached.

In the invention thus constituted, the frequency adjustment circuit adjusts the frequency of the AC voltage applied to the resonant frequency of the sensing portion, to which the vibration excitation element is attached. As the sensing portion vibrates at the resonant frequency, the sensing portion can be made to vibrate at a large amplitude using a small excitation force, and the touch detection device can be activated with little energy consumed.

In the present invention, preferably, the frequency adjustment circuit applies the AC voltage for a predetermined period multiple times at different frequencies, and the frequency at which the amplitude of the output signal from the vibration excitation element is maximal following the stopping of the AC voltage application, is determined by the frequency adjustment circuit to be the resonant frequency at which the sensing portion, to which the vibration excitation element is attached.

In the invention thus constituted, the frequency of the AC voltage can also be adjusted after the sensing portion and the vibration excitation element are installed in the water handling equipment, so the frequency of the applied AC voltage can be matched to the resonant frequency even when the resonant frequency has been offset due to the passage of time.

In the present invention, preferably, when there are multiple frequencies at which the amplitude of the output signal detected after application of the AC voltage, is maximized, then among the frequencies at which amplitude is maximized, the frequency at which amplitude fluctuations of the output signal are smallest during application of the AC voltage to the vibration excitation element, is determined by the frequency adjustment circuit to be the resonant frequency of the sensing portion, to which the vibration excitation element is attached.

In the invention thus constituted, the resonant frequency of the sensing portion, to which the vibration excitation element is attached, is automatically and reliably set by a simple algorithm.

The present invention preferably further includes a frequency offset sensing circuit for sensing the occurrence of a frequency offset between the resonant frequency of the sensing portion and the frequency of the AC voltage applied to the vibration excitation element; wherein when the frequency offset is sensed by the frequency offset sensing circuit, the frequency adjustment circuit performs an adjustment so that the frequency of the AC voltage matches the resonant frequency of the sensing portion.

In the present invention it is desirable for the frequency of the AC voltage applied to the vibration excitation element and the sensing portion resonant frequency to sufficiently match. It can occur, however, that due to temperature changes, aging, and the like in the sensing portion, the sensing portion resonant frequency changes temporarily or permanently after initial adjustment of the AC voltage frequency. When such frequency offsets occur, there is a risk that sensing performance will not be fully realized, or that false sensing will occur. It is difficult, however, for a user to discover frequency offsets in a touch detection device. The invention thus constituted comprises a frequency offset sensing circuit for sensing the occurrence of offsets between the sensing portion resonant frequency and the frequency of an AC voltage applied to the vibration excitation element; when a frequency offset is sensed by the frequency offset sensing circuit, the frequency adjustment circuit performs an adjustment so that the AC voltage frequency matches the resonant frequency of the sensing portion, so frequency offsets can be monitored, and the touch detection device can be maintained in a favorable state at all times.

In the present invention, preferably, the frequency adjustment circuit adjusts the frequency when the frequency offset sensed by the frequency offset sensing circuit is continuously present for a predetermined frequency offset determination time or greater.

In some cases permanent changes in the sensing portion resonant frequency occur due to aging, but there are also temporary changes caused by temperature changes, such as hot water contacting the sensing portion. Hence when the frequency is immediately adjusted for the given reason of a frequency offset occurring between the sensing portion resonant frequency and the AC voltage frequency, there is a potential that frequency adjustments will be made more difficult due to resonant frequency changes during adjustment, or that the degree of the offset will actually be increased. In the invention thus constituted, the frequency adjustment circuit performs a frequency adjustment when frequency offset sensing by the frequency offset sensing circuit has continued for a predetermined frequency offset determination time or greater, therefore automatic adjustment by the frequency adjustment circuit can be more reliably performed.

In the present invention, preferably, when the resonant frequency of the sensing portion is below the frequency of the AC voltage applied to the vibration excitation element, the frequency offset determination time is set to be longer than when the resonant frequency of the sensing portion is above the frequency of the AC voltage applied to the vibration excitation element.

The present inventors have discovered that the drop in sensing portion resonant frequency is often the result of adhesion of water droplets to the sensing portion. There is a high probability that such frequency offsets caused by adhesion of water droplets will be eliminated with the passage of time, so it is better not to make immediate adjustments even when an offset is sensed. The inventors discovered that the state whereby the sensing portion resonant frequency is higher than the AC voltage frequency in most cases occurs because a frequency adjustment was made when water droplets had previously adhered, lowering the AC voltage frequency. In such cases it is desirable to immediately adjust the frequency. In the invention thus constituted, the frequency offset determination time is set to be longer if the sensing portion resonant frequency is below the frequency of the AC voltage applied to the vibration excitation element than if the sensing portion resonant frequency is above the frequency of the AC voltage applied to the vibration excitation element, therefore temporary changes in resonant frequency caused by water droplet adhesion can also be effectively handled.

In the present invention, preferably, the frequency adjustment circuit is constituted to search for the resonant frequency of the sensing portion within a predetermined frequency range, and to be capable of executing a first adjustment mode and a second adjustment mode between which different search frequency ranges are used, wherein in the first adjustment mode the resonant frequency is searched within a first frequency range which includes a standard frequency of the sensing portion, and in the second adjustment mode the resonant frequency is searched within a second frequency range narrower than the first frequency range, which includes the current frequency of the AC voltage.

The inventors discovered that the sensing portion resonant frequency offset occurs due to differences between individual sensing portions and adherence of water droplets, etc. to the sensing portion, and that the size of such resonant frequency offsets varies depending on the cause of the frequency offset. Also, the device cannot be used as a touch detection device during operation of the frequency adjustment circuit, which poses an inconvenience to the user when the frequency adjustment is time consuming. In the invention thus constituted, a resonant frequency within a first frequency range including the standard frequency of the sensing portion is searched in the first adjustment mode, and a resonant frequency including the frequency of the current AC voltage and within a second frequency range narrower than the first frequency range is searched in the second adjustment mode, therefore adjustment according to the cause of the frequency offset occurrence can be performed in a short time.

The present invention preferably further includes a determination circuit for determining whether a frequency adjustment by the frequency adjustment circuit has succeeded; wherein in the first adjustment mode, when the determination circuit determines that the frequency adjustment has failed, the resonant frequency is repeatedly searched until the frequency adjustment succeeds, while in the second adjustment mode, when the determination circuit determines that the frequency adjustment has failed, the frequency of the current AC voltage is maintained without repeatedly searching for the resonant frequency.

In the invention thus constituted, in the first adjustment mode, if the determination circuit determines that the frequency adjustment has failed, a resonant frequency is repeatedly searched until the frequency adjustment succeeds, while in the second adjustment mode, if the determination circuit determines that the frequency adjustment has failed, the frequency of the current AC voltage is maintained without repeatedly searching for a resonant frequency, therefore an appropriate frequency adjustment can be performed according to the usage state of the touch detection device, and reliable frequency adjustment and reduced unusable time can both be achieved.

In the present invention, preferably, the frequency adjustment circuit is constituted for applying AC voltages to the vibration excitation element at multiple frequencies within the predetermined frequency range, respectively obtaining output signals from the vibration excitation element for each application of an AC voltage, and performing the frequency adjustment by analyzing envelope detection waveforms of these output signals, while the determination circuit determines that the frequency adjustment by the frequency adjustment circuit has failed when the envelope detection waveforms include a waveform which does not decrease monotonically after application of the AC voltage.

After completion of application of an AC voltage, the reverberation vibration waveform has a large initial amplitude then becomes a damped vibration waveform in which the amplitude gradually decreases, but when significant noise is mixed in with the acquired waveform, or something contacts the sensing portion, distortion occurs in the damped vibration waveform, such that the detected waveform is not a monotonically decreasing waveform. In the invention thus constituted, when a non-monotonically decreasing waveform is included in the detected waveform after application of an AC voltage, a determination is made that frequency adjustment by the frequency adjustment circuit has failed, therefore incorrect frequency adjustment due to the effects of noise, etc. can be prevented.

In the present invention, preferably, the frequency adjustment circuit is constituted to apply the AC voltage to the vibration excitation element at multiple frequencies within the predetermined frequency range, to acquire output signals from the vibration excitation element when each AC voltage is applied, to search for the resonant frequency based on these output signals, and then to make a determination, while the determination circuit determines that the frequency adjustment by the frequency adjustment circuit has failed when a vibration energy of the sensing portion detected after the AC voltage at the determined resonant frequency is applied, does not reach a predetermined threshold value.

In a situation where the applied AC voltage frequency and the sensing portion resonant frequency do not match well, vibration of the sensing portion at the resonant frequency increases vibration of the sensing portion, and reverberation vibration energy after the AC voltage is applied also increases. However, if the frequency adjustment is performed with large quantities of water droplets adhered to the sensing portion or with objects contacting the sensing portion during the frequency adjustment, the reverberation vibration energy is reduced. A resonant frequency thus searched without the occurrence of sufficient reverberation vibration has a high probability of containing a large error. In the invention thus constituted, if the vibration energy of the sensing portion does not reach a predetermined threshold value after stopping the application of the AC voltage at the determined resonant frequency, a determination is made that the frequency adjustment by the frequency adjustment circuit has failed, so incorrect frequency adjustments due to frequency adjustment in an inappropriate environment can be prevented.

In the present invention, preferably, once the contact by the target object has first been determined by the contact determination circuit, the contact determination confirming circuit performs the contact determination confirming operation in which the AC voltage at a confirming frequency different from the normal frequency of the AC voltage is applied, and the contact determination confirming circuit fixes the judgment of contact with the sensing portion when the contact of the target object is also determined by the contact determination circuit by applying the AC voltage at the confirming frequency.

In the present invention when the target object contacts the sensing portion, the phenomenon of diminishing reverberation vibration energy after completion of application of an AC voltage is utilized to detect target object contact. However, the sensing portion cannot be sufficiently excited even when there is an offset between the frequency of the applied AC voltage and the resonant frequency of the sensing portion, so the reverberation vibration energy drops. The sensing portion resonant frequency also changes when water droplets and the like have adhered to the sensing portion, resulting in a drop in reverberation vibration energy, with the risk that target object contact will be falsely sensed. In the invention thus constituted, if an AC voltage at a confirmation frequency different from the normal AC voltage frequency is applied as a contact determination confirming operation, and contact by the target object is confirmed by the contact determination circuit using the application of AC voltage at the confirmation frequency as well, the judgment of contact with the sensing portion is fixed. Thus even if a mistaken determination of target object contact is made by the contact determination circuit due to frequency offset, the contact determination confirming circuit performs an excitation using an AC voltage at a confirming frequency different from the normal AC voltage frequency, therefore even when the resonant frequency is offset, a large reverberation vibration is excited as the confirming frequency approaches the resonant frequency, and false sensing due to frequency offsets can be effectively suppressed.

Also, the present invention is a faucet apparatus for switching between water spouting and shut off by a touch operation, comprising: the touch detection device of the present invention; an operating portion including the sensing portion; and an on-off valve for opening and closing based on a determination of contact by the target object with the sensing portion performed by the touch detection device.

Effect of the Invention

Using the touch detection device of the present invention and a faucet apparatus comprising same, operation can be performed with a light touch, and false operation can be prevented even when used in water handling equipment.

EMBODIMENTS

Next, referring to the attached figures, we explain a faucet apparatus according to a first embodiment of the invention. The touch detection device of the first embodiment of the invention is built into the faucet apparatus of the present embodiment; user operations are sensed using this touch detection device to allow switching between spouting and water shut off.

Figure 1:
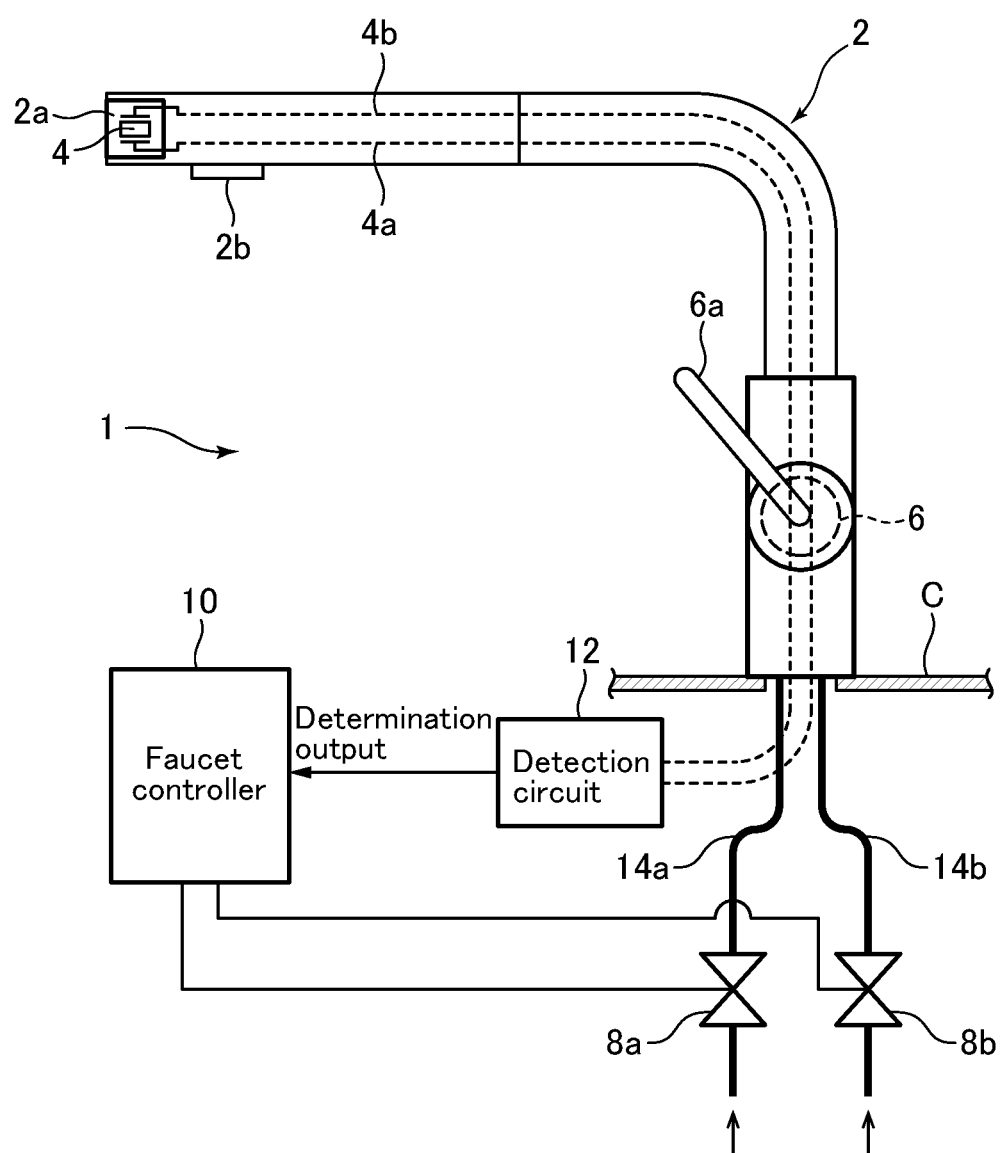
FIG. 1 A block diagram showing the simplified constitution of a faucet apparatus in a first embodiment of the invention.
Figure 2:
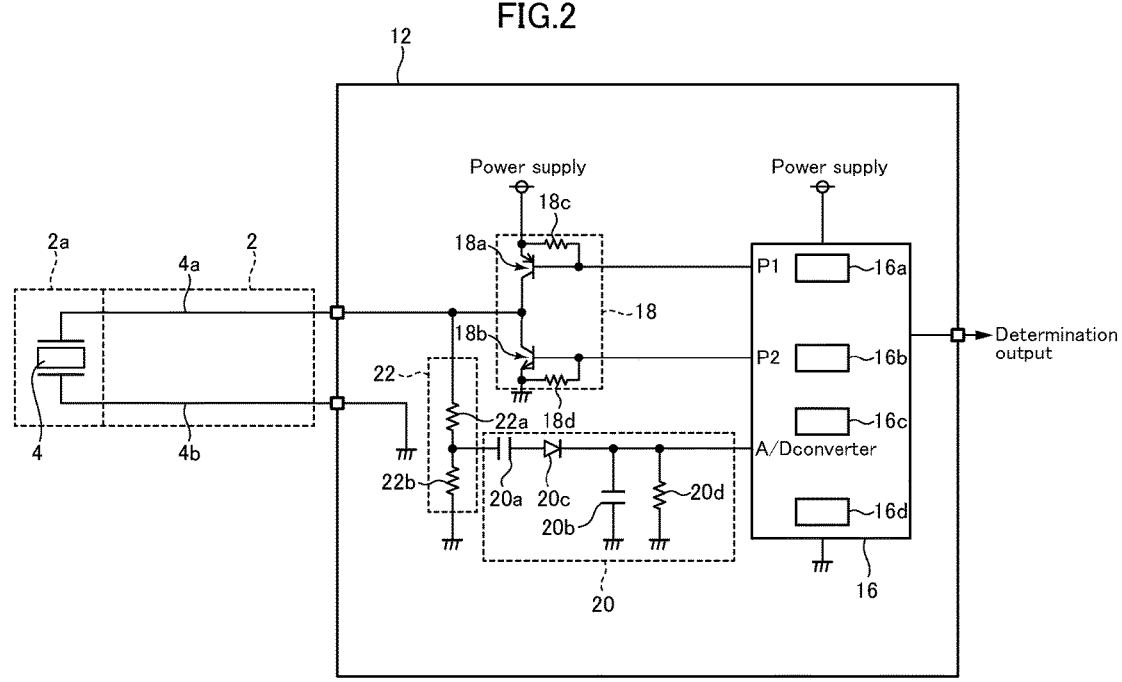
FIG. 2 A circuit diagram showing the simplified constitution of a touch detection device in a first embodiment of the invention.
Figure 3:
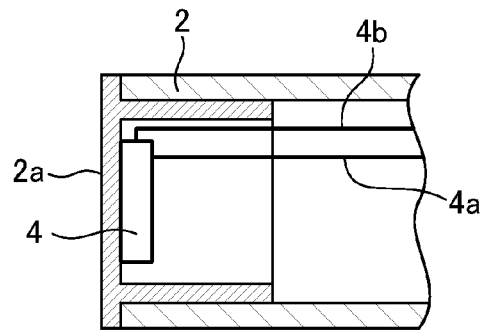
FIG. 3 A cross section showing an expanded view of a sensing portion disposed at the tip portion of the faucet apparatus in a first embodiment of the invention.

FIG. 1 is a block diagram showing the simplified constitution of a faucet apparatus in the present embodiment. FIG. 2 is a circuit diagram showing the simplified constitution of a touch detection device in the present embodiment. FIG. 3 is a cross section showing an expanded view of a sensing portion disposed at the tip portion of the faucet apparatus.

As shown in FIG. 1, the flush toilet 1 of a first embodiment of the invention has: a faucet main body 2 attached on a counter board C, a sensing portion 2a disposed on the tip portion of this faucet main body 2, a piezo-electric element 4, being a vibration excitation element attached to this sensing portion 2a, and a hot/cold mixing valve 6 built into the base portion of the faucet main body 2. In addition, the flush toilet 1 has: a hot water electromagnetic valve 8a and cold water electromagnetic valve 8b, disposed on the bottom side of a counter board C, being on/off valves for respectively switching between the supply and shut off of hot and cold water, a faucet controller 10 for controlling the opening and closing of these electromagnetic valves, and a detection circuit 12 for sending signals to this faucet controller 10 in response to operations of the sensing portion 2a. Note that within the faucet apparatus 1 of the present embodiment, the sensing portion 2a, piezo-electric element 4, and detection circuit 12 constitute a touch detection device according to a first embodiment of the invention.

The faucet apparatus 1 of the present embodiment is constituted so that the hot water electromagnetic valve 8a and cold water electromagnetic valve 8b are opened and closed by a user lightly touching the sensing portion 2a disposed on the tip portion of the faucet main body 2, thereby enabling switching between a water shut-off state and a water spouting state. Hence in the present embodiment the tip of the faucet main body 2 on which the sensing portion 2a is disposed functions as an operating portion for the faucet apparatus 1.

The faucet main body 2 is a metal tubular member having: a base portion rising essentially vertically from the counter board C, and a horizontal portion extending essentially horizontally from the end of this base portion; a spout opening 2b is disposed at the end of the horizontal portion.

The sensing portion 2a is disposed to form an end surface at the end of the faucet main body 2, and a signal for sensing whether a target object such as a user's hand has contacted the sensing portion 2a is sent to the detection circuit 12. As described below, a piezo-electric element 4 is built into the sensing portion 2a, and this piezo-electric element 4 is electrically connected to the detection circuit 12 by the two signal lines 4a, 4b which are passed through the interior of the faucet main body 2.

The hot/cold mixing valve 6 is built into the base portion of the faucet main body 2, and is respectively connected to the hot water supply pipe 14a connected to the downstream hot water electromagnetic valve 8a, and the cold water supply pipe 14b connected on the downstream side of the cold water electromagnetic valve 8b. A hot water adjustment handle 6a is attached to the hot/cold mixing valve 6; the mixing ratio of hot water supplied from the hot water supply pipe 14a to cold water supplied from the cold water supply pipe 14b is set by adjusting this hot water adjustment handle 6a, so the temperature of the water spouted from the spout opening 2b can be adjusted. Water mixed in the hot/cold mixing valve 6 is guided through a water conduit member (not shown) disposed inside the faucet main body 2, and spouted from the spout opening 2b.

The hot water electromagnetic valve 8a and cold water electromagnetic valve 8b are electromagnetic valves opened and closed in response to control signals from the faucet controller 10. The hot water electromagnetic valve 8a is connected to piping from a hot water supply device (not shown), and when open allows hot water to flow out to the hot water supply pipe 14a. The cold water electromagnetic valve 8b is connected to a public water supply, and when opened allows water to flow out to the cold water supply pipe 14b.

The faucet controller 10 outputs a control signal to the hot water electromagnetic valve 8a and the cold water electromagnetic valve 8b in response to the output signal from the detection circuit 12, opening and closing these valves.

The detection circuit 12 is electrically connected to the piezo-electric element 4 built into the sensing portion 2a, and outputs a determination output signal to the faucet controller 10. The detection circuit 12, by applying an AC voltage to the piezo-electric element 4, causes it to ultrasonically vibrate at a predetermined frequency, and acquires an output signal from the piezo-electric element 4 terminal. In addition, a determination is made of whether a target object, being a user's hand or the like, has touched (contacted) the sensing portion 2a based on an output signal acquired from the piezo-electric element 4, and the resulting determination is output to the faucet controller 10 as a determination output signal.

Specifically, the faucet controller 10 and the detection circuit 12 can be comprised by combining electronic components such as a microprocessor or microcomputer, semiconductors, resistors, capacitors, etc., and programs for running the microprocessor, etc. The faucet controller 10 and the detection circuit 12 can also be comprised as a single unit of the above electronic components.

Next, referring to FIG. 2, we explain the constitution of the detection circuit 12.

As shown in FIG. 2, a microcomputer 16 and a voltage divider circuit 22 are built into the detection circuit 12.

The microcomputer 16, using a program which runs it, is constituted to function as a contact determination circuit 16a, contact determination confirming circuit 16b, anomaly sensing circuit 16c, and frequency adjustment circuit 16d.

The operation of these circuits is discussed below. The microcomputer 16 is constituted to control two transistors forming a drive circuit 18 using output signals from two output ports P1 and P2. An A/D converter circuit for converting an analog voltage signal output from the signal conversion circuit 20 is built into the microcomputer 16. Each of the circuits built into the microcomputer 16 performs calculations based on the converted digital values to determine whether the sensing portion 2a has been touched.

The drive circuit 18 is formed of a PNP transistor 18a connected to the power supply, an NPN transistor 18b connected to ground, and two resistors 18c, 18d. The emitter terminal on the PNP transistor 18a is connected to a power supply, and the base terminal thereof is connected to output port P1 on the microcomputer 16. The resistor 18c is connected between the base and emitter of the PNP transistor 18a. At the same time, the NPN transistor 18b emitter terminal is connected to ground, while the base terminal is connected to the output port P2 on the microcomputer 16. The resistor 18d is connected between the base and the emitter of the NPN transistor 18b. Furthermore, each of the collector terminals on the PNP transistor 18a and NPN transistor 18b is connected to one another, and to one of the electrodes (input terminals) of the piezoelectric element 4 through the signal line 4a. The other electrode on the piezo-electric element 4 is connected to ground through the signal line 4b.

The PNP transistor 18a and NPN transistor 18b are mutually turned on and off at a predetermined cycle by signals from the microcomputer 16 output ports P1, P2. With the PNP transistor 18a is turned on and the NPN transistor 18b is turned off, a voltage equal to the power supply voltage is output on the signal line 4a, and with the PNP transistor 18a turned off and the NPN transistor 18b turned on, the signal line 4a is at ground potential. Repeated alternation of these states at a predetermined cycle results in the application of an AC voltage at a predetermined frequency to one of the electrodes on the piezo-electric element 4 via the signal line 4a. When the AC voltage is not applied to the piezo-electric element 4, both transistors are turned off, and the collectors on each transistor are placed in a high impedance state (effectively electrically disconnected). Note that in the present embodiment, the alternating turning on and off of the PNP transistor and NPN transistor results in application of an AC voltage to the piezo-electric element 4, but it is also possible to apply an AC voltage using any desired switching element such as an FET.

The voltage divider circuit 22 comprises two resistors, 22a and 22b, and divides the voltage appearing on one of the terminals of the piezo-electric element 4 so as to adjust to an appropriate voltage. I.e., the signal on one of the terminals of the resistor 2a is connected to the signal line 4a, and the other terminal is connected to the other terminal of the resistor 22b. The other terminal of the resistor 22b is connected to ground. The voltage appearing on the signal line 4a is in this manner voltage divided by the resistors 22a, 22b and adjusted to an appropriate voltage. As noted above, with an AC voltage applied to the piezo-electric element 4, the power supply voltage and ground potential alternately appear on one of the terminals (signal line 4a) of the piezo-electric element 4. In response, with the output of the drive circuit 18 placed in a high impedance state (both transistors off), an electromotive force generated by the piezo-electric element 4 appears on the signal line 4a. The voltage divider circuit 22 divides these voltages and outputs the divided voltage to the signal conversion circuit 20. I.e., the terminal connected to one of the electrodes on the piezo-electric element 4 functions as an input terminal for applying an AC voltage, and the output signal from the piezo-electric element 4 is obtained from this input terminal.

The signal conversion circuit 20 comprises two capacitors 20a, 20b, a diode 20c, and a resistor 20d. One of the terminals of the capacitors 20a, 20b is connected to the connecting point of resistors 22a, 22b; the other terminal thereof is connected to the anode terminal of a diode 20c. In addition, the other diode 20c terminal is connected to the input terminal of an A/D converter built into the microcomputer 16. The cathode terminal of the diode 20c is connected to ground through the capacitor 20b and the resistor 20d, respectively. The DC (direct current) component of the output signal from the voltage divider circuit 22 is in this manner removed by the capacitor 20a, the signal from which the AC component is removed is envelope-detected by the diode 20c, and the high frequency component thereof is cut by the capacitor 20b and the voltage divider circuit 22 output signal is input to the A/D converter in the microcomputer 16.

Next, referring to FIGS. 2 and 3, we explain the constitution of the sensing portion 2a.

As shown in FIG. 3, the sensing portion 2a is constituted by a metal member attached at the end of the faucet main body 2, and together with the faucet main body 2 forms the external appearance of the faucet apparatus 1. The sensing portion 2a has a disk portion touched by users hand, etc., and a cylindrical portion extending on the rear surface side of this disk portion.

In the present embodiment, the piezo-electric element 4 is a disk-shaped element using a piezo-electric ceramic such as barium titanate or lead zirconate titanate, and electrodes are mounted on both sides of this piezo-electric ceramic. By applying an AC voltage through these signal lines 4a, 4b, the piezo-electric element 4 repetitively deforms so as to bend as a whole, thereby vibrating. The piezo-electric element 4 is adhered by adhesive to the rear surface side of the sensing portion 2a disk portion, therefore the piezo-electric element 4 and the disk portion bend and vibrate as an integral unit. I.e., the sensing portion 2a is made to bend and vibrate at an amplitude of approximately a few μm by applying an AC voltage at a predetermined frequency to the piezo-electric element 4. Conversely, when the piezo-electric element 4 is bent and vibrated, an electromotive force is generated between the electrodes thereof (between signal lines 4a, 4b). Note that in the present embodiment the frequency of the applied AC voltage is set at approximately 40 kHz, which is the resonant frequency when the piezo-electric element 4 and the disk portion flexurally vibrate as an integral unit. The resonant frequency is preferably set within an ultrasonic band of approximately 20 kHz to approximately 60 kHz.

Figure 4:
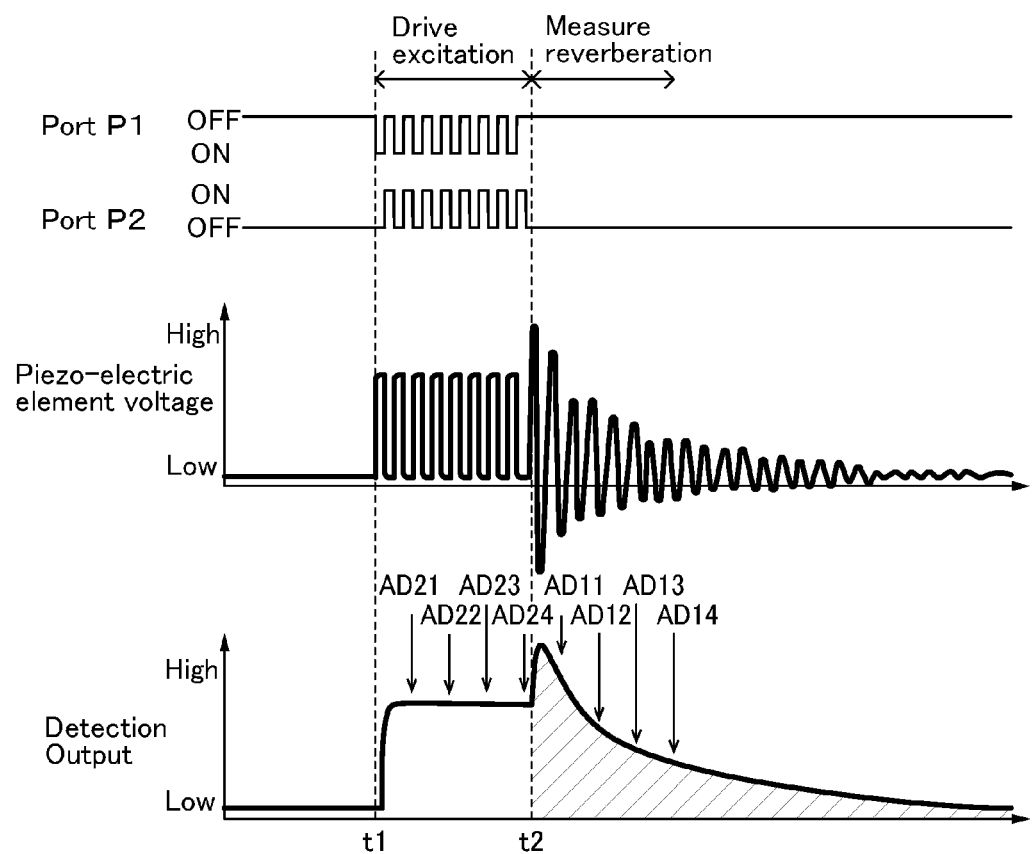
FIG. 4 A diagram showing a typical output waveform at a piezo-electric element when a user is not touching the sensing portion in a first embodiment touch detection device of the invention.
Figure 5:
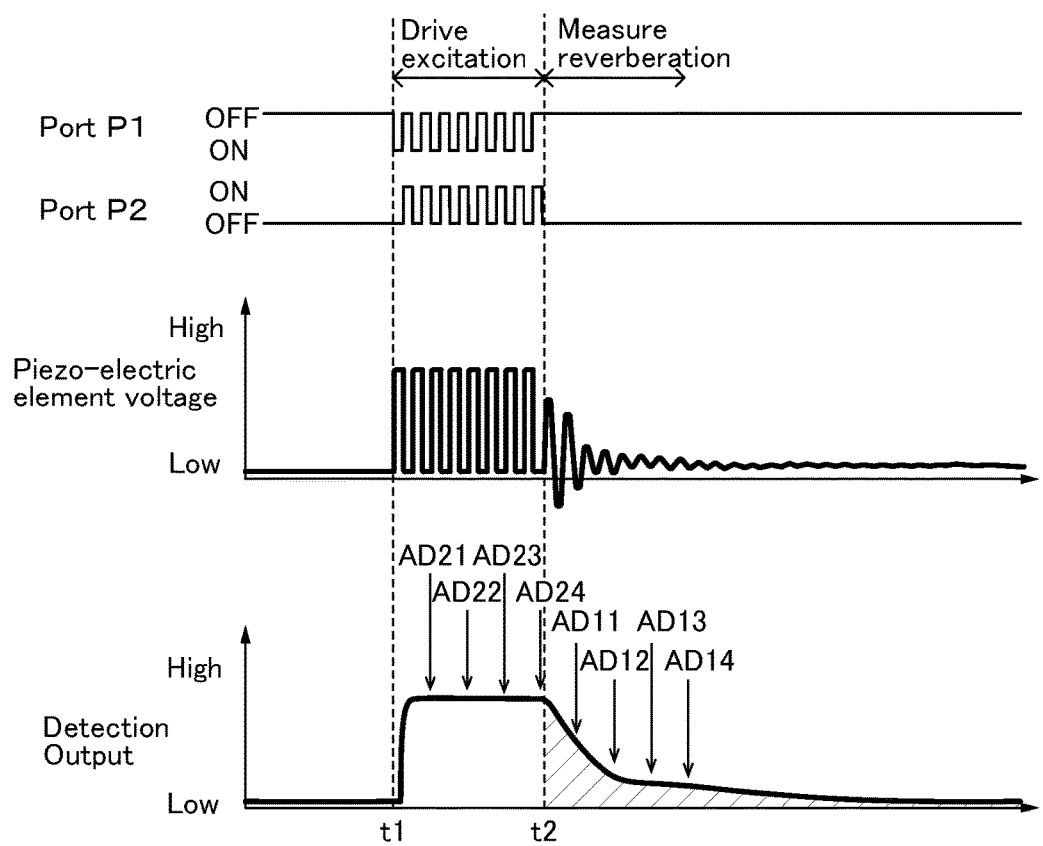
FIG. 5 A diagram showing a typical output waveform at a piezo-electric element when a user is touching the sensing portion in a first embodiment touch detection device of the invention.

Next, referring to FIGS. 4 and 5, we explain the principle of detection in a touch detection device according to a first embodiment of the invention.

In a touch detection device according to a first embodiment of the invention, FIG. 4 shows a typical output waveform from the piezo-electric element 4 when a user does not touch the sensing portion 2a, and FIG. 5 shows a typical output waveform from the piezo-electric element 4 when a user touches the sensing portion 2a. Note that FIGS. 4 and 5 show the output voltage waveform from the output ports P1, P2 (FIG. 2) of the microcomputer 16 on the top, the output voltage waveform of the piezo-electric element 4 (the voltage waveform between the signal lines 4a and 4b) in the middle, and the output voltage waveform from the signal conversion circuit 20 (input waveform to the microcomputer 16 A/D converter) on the bottom. Also, FIGS. 4 and 5, etc, show signal waveforms schematically, and differ from actual waveforms with respect to items such as the number of waves output during application of an AC voltage.

First, application of an AC voltage to the piezo-electric element 4 is started at time t1 in FIG. 4. I.e., as shown in the top portion of FIG. 4, the outputting of a voltage pulse alternately on the output ports P1, P2 of the microcomputer 16 results in alternately turning on the PNP transistor 18a and the NPN transistor 18b in the drive circuit 18 (FIG. 2). Thus, as shown in the middle diagram in FIG. 4, a pulse-shaped AC voltage is applied between the two electrodes of the piezo-electric element 4 (signal lines 4a, 4b). The application of this AC voltage results in flexural vibration of the piezo-electric element 4. As described above, the frequency of the AC voltage applied to the piezo-electric element 4 is set to match the resonant frequency of the sensing portion 2a and the piezo-electric element 4, which vibrate as a single unit. Therefore the amplitude of the flexural vibration by the sensing portion 2a and the piezo-electric element 4 resulting from the application of an AC voltage is approximately a few μm, and the amplitude becomes larger than when the vibration is excited at other frequencies. Note that during application of an AC voltage, the piezo-electric element 4 terminal (signal line 4a) is connected to either the power supply voltage or ground by either the PNP transistor 18a or the NPN transistor 18b, therefore the voltage between the two electrodes of the piezo-electric element 4 (center drawing in FIG. 4) is dominated by these (it is not the case that the electromotive force generated by the flexural vibration of the piezo-electric element 4 is being manifested).

Next, at time t2 in FIG. 4, application of an AC voltage to the piezo-electric element 4 is stopped. When the application of the AC voltage is stopped, both the PNP transistor 18a and the NPN transistor 18b of the drive circuit 18 are turned off, and the drive circuit 18 output goes to high impedance (a state of electrical disconnection). At the same time, the sensing portion 2a and the piezo-electric element 4 are flexurally vibrated at the resonant frequency by excitation of vibration between times t1 and t2, and the vibration remains after application of the AC voltage is stopped at time t2 (this phenomenon is generally referred to as "reverberation"), then gradually attenuates (the vibration amplitude diminishes). After application of the AC voltage is stopped, the output of the drive circuit 18 goes to a high impedance, therefore the electromotive force generated by the flexural vibration of the piezo-electric element 4 appears between the two terminals of the piezo-electric element 4 (between signal lines 4a, 4b) (time t2 forward in the middle drawing in FIG. 4).

In the touch detection device of the first embodiment of the invention, a determination as to whether or not the sensing portion 2a has been touched is made based on the degree of the "reverberation vibration" remaining in the sensing portion 2a (and the piezo-electric element 4) after stopping the application of an AC voltage.

Here, as shown in the middle drawing in FIG. 4, if the sensing portion 2a has not been touched, the vibration amplitude is large after time t2 when the application of an AC voltage is stopped, and the time until that vibration attenuates also lengthens. On the other hand, as shown in the middle section of FIG. 5, when the sensing portion 2a has been touched (there is contact by a user's hand, etc. with the sensing portion 2a), the voltage amplitude is small after time t2, and that vibration also attenuates in a short period. I.e., it is believed that if a user's hand or the like contacts the sensing portion 2a, sensing portion 2a vibration is absorbed by the contacting hand or the like, and the "reverberation vibration" remaining after stopping the application of an AC voltage diminishes.

In the present embodiment, the DC component of the voltage waveform on the piezo-electric element 4 shown in the middle of FIGS. 4 and 5 is removed, and a determination of whether a touch has occurred is made based on the envelope-detected output waveform from the signal conversion circuit 20 (bottom of FIGS. 4 and 5). Specifically, in the present embodiment a determination of whether touching has occurred is made based on the size of the area surrounded by the output waveform from the signal conversion circuit 20 after time t2 (the area of the diagonally shaded portion in FIGS. 4 and 5. This is proportional to the vibration energy of the sensing portion 2a and the piezo-electric element 4 after excitation stops).

Next, referring to FIGS. 6 through 15, we explain the operation of a faucet apparatus 1 according to a first embodiment of the invention.

Figure 6:
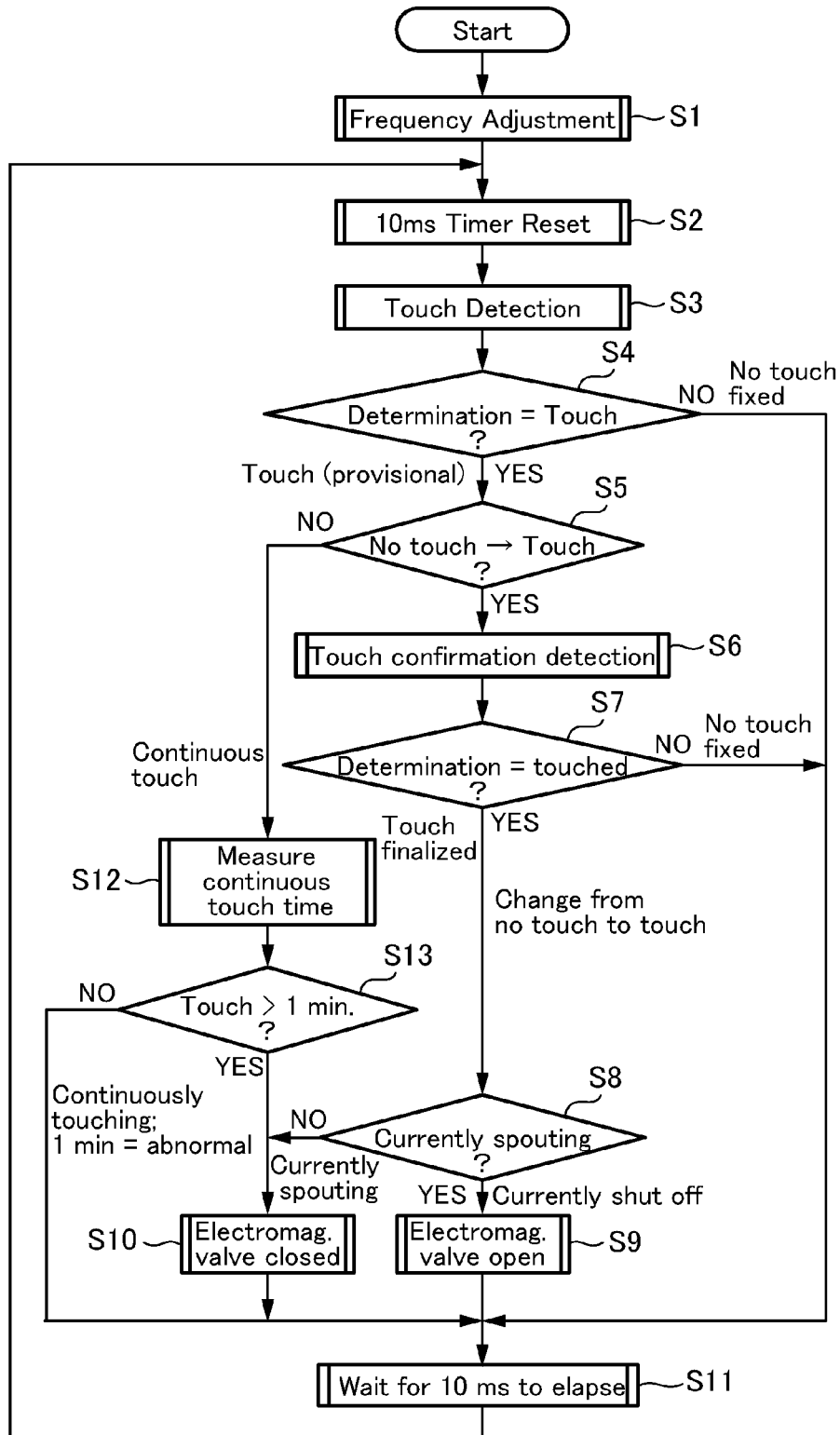
FIG. 6 A main flow diagram showing the operation of a faucet apparatus in a first embodiment of the invention.
Figure 7:
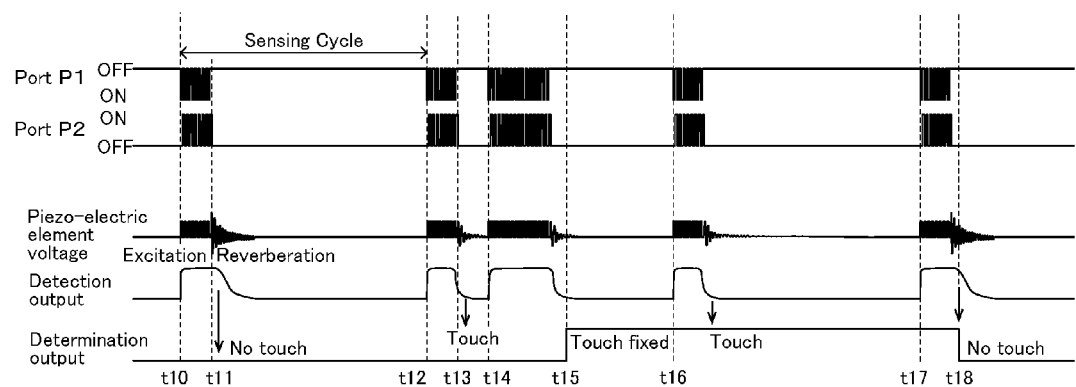
FIG. 7 A time chart showing an example of the operation of a faucet apparatus in a first embodiment of the invention.
Figure 8:
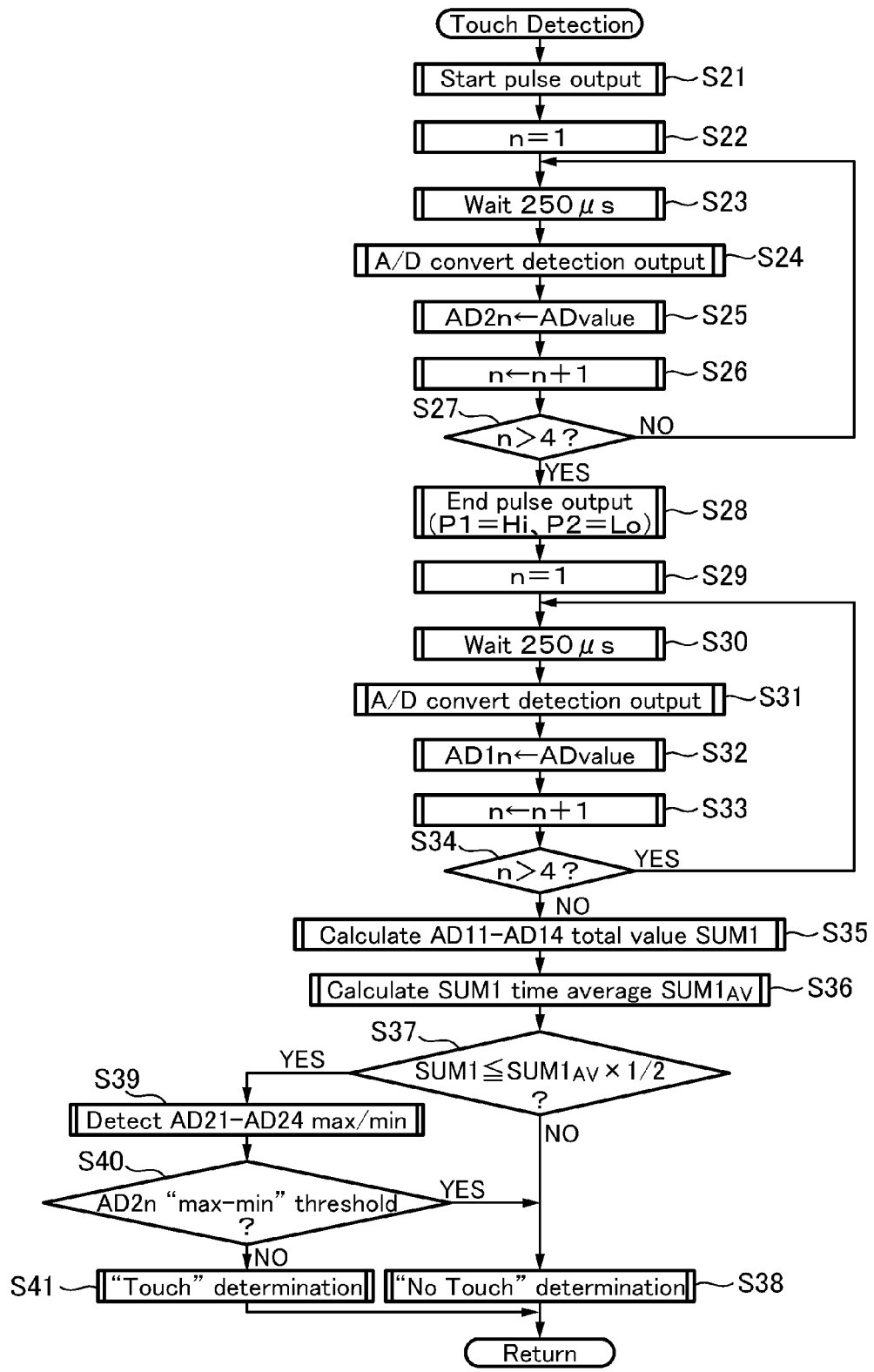
FIG. 8 A touch detection flow called as a subroutine from the main flow in FIG. 6.

FIG. 6 is a main flow diagram showing the operation of a faucet apparatus in a first embodiment of the invention; FIG. 7 is a time chart showing an example of the operation thereof. FIG. 8 is a touch detection flow called as a subroutine from the main flow in FIG. 6. Note that the FIG. 7 time chart, like the time charts in FIGS. 4 and 5, shows the output voltage waveform output ports P1, P2 in the first level, the output voltage waveform of the piezo-electric element 4 in the second level, and the output voltage waveform from the signal conversion circuit 20 in the third level, and shows the determination output from the detection circuit 12 output to the faucet controller 10 in the bottommost level.

The processing in the FIG. 6 flow chart is executed by the microcomputer 16 built into the detection circuit 12.

First, a frequency adjustment of the AC voltage applied to the piezo-electric element 4 is executed in step S1. This frequency adjustment is processing by which the frequency of the AC voltage applied to the piezo-electric element 4 is accurately matched to the resonant frequency of the sensing portion 2a and the piezo-electric element 4; in the present embodiment, this processing is executed when the power supply to the detection circuit 12 is turned on to the detection circuit 12. As a variant example, it is also possible to constitute the invention by placing a switch (not shown) on the detection circuit 12 for executing a frequency adjustment, so that a frequency adjustment is executed by operating this switch.

In order to fully realize performance of the touch detection device of the present embodiment, the frequency of the applied AC voltage must be sufficiently matched to its resonant frequency. There are individual differences in the resonant frequencies at which a sensing portion 2a and a piezo-electric element 4 vibrate significantly, and it is desirable to adjust the frequency of the applied AC voltage according to the faucet main body 2 combined with the detection circuit 12 (the sensing portion 2a and the piezo-electric element 4). Also, by providing such frequency adjustment functionality, individual variability of faucet main bodies 2 combined with detection circuits 12 can be addressed, and a general purpose detection circuit 12 capable of combination with multiple types of faucet main body 2 can be constituted. Specific processing in step S1 is described later.

Next, in step S2 of FIG. 6 the 10 ms timer is reset. In the present embodiment, application of an AC voltage to the piezo-electric element 4 is executed intermittently each 10 ms, which is the sensing cycle. In step S2, a 10 ms timer controlling this AC voltage application interval is reset, and timer counting is started. The sensing cycle is preferably set to approximately 10 to 100 ms.

In addition, in step S3 the touch detection flow shown in FIG. 8 is executed as a subroutine. The touch detection executed in step S3 is executed based on the principle explained using FIGS. 4 and 5: the specific processing in the FIG. 8 flow is explained below. Also, in the example shown in FIG. 7, step S3 is executed at time t10, and an AC voltage is applied to the piezo-electric element 4.

Next, in step S4, a determination is made of whether the detection result in step S3 was a "touch" or a "no touch," If a "touch," the system advances to step S5; if a "no touch," the system advances to step S11. In the example shown in FIG. 7, because the reverberation after the excitation (application of AC voltage) executed from time t10 to t11 is large, a "no touch" determination is made. In step S11, after a "non-step" determination, the system stands by until the count started in step S2 reaches 10 ms, and when 10 ms have elapsed returns to step S2.

In step S2, the 10 ms timer is again reset and counting restarted, and in step S3 touch detection is again executed. In the example shown in FIG. 7, step S3 is again executed at time t12, after 10 ms have elapsed from the start of the previous excitation at time t10. In addition, in the FIG. 7 example, because reverberation is small after stopping (from time t13 forward) the excitation started at time t12, the detection results at step S3 are determined to be a "touch." When a "touch" is determined in step S3, the system advances from step S4 to step S5.

At step S5, a judgment is made as to whether the detection results at step S3 have changed from "no touch" to "touch." In the FIG. 7 example, because the detection result for the previous iteration started at time t10 is a "no touch," and the detection result for the current iteration started at time t12 is a "touch," the system advances to step S6.

In step S6, the flow chart shown in FIG. 8, which is for a "touch confirming detection," is executed as a subroutine. This "touch confirming detection" is processing executed in order to prevent false sensing due to a "touch detection" in step S3 if the detection result from step S3 changes from "no touch" to "touch," Specifically, "touch confirming detection" is executed by applying an AC voltage to the piezo-electric element 4 for a longer period than the "touch detection;" specific processing thereof is discussed below. In the FIG. 7 example, "touch confirming detection" is started at the time t14, immediately following the completion of "touch detection" in step S3.

In step S7, a determination is made of whether the "touch confirming detection" results were a "touch" or not. If those results were a "no touch," there is a high probability the detection of a "touch" in step S3 was a false sensing, therefore the system advances to step S11 without opening and closing the electromagnetic valve, and stands by until 10 ms have elapsed from time t12. On the other hand if the "touch confirming detection" result was a "touch," the "touch" determination is fixed, and the system advances to step S8.

In step S8 a determination is made of whether the faucet apparatus 1 is in a spouting state; if it is spouting, the system advances to step S10; if it is not spouting, the system advances to step S9. In step S10, the sensing portion 2a has been newly touched in the spouting state (time t12), therefore the hot water electromagnetic valve 8a and the cold water electromagnetic valve 8b are closed, and a switch is made to the shut off state. Specifically, when a "touch" detection is fixed in the detection circuit 12, a signal indicating "touch confirmed" is output from the detection circuit 12 to the faucet controller 10, and the faucet controller 10 sends a control signal to the hot water electromagnetic valve 8a and the cold water electromagnetic valve 8b, closing these. In step S9, on the other hand, the sensing portion 2a has been newly touched in the shut off state (time t12), therefore the hot water electromagnetic valve 8a and the cold water electromagnetic valve 8b are opened, and a switch is made to the spouting state. In the example show in FIG. 7, detection of a "touch" is fixed by the touch confirming detection in step S6 started at time t14; at time 15, a determination output indicating that the "touch" detection at time t15 has been fixed is output to the faucet controller 10.

In this manner, even when a "touch" of the sensing portion 2a is detected, touch detection in step S3 is performed at a regular interval every 10 ms, which is the predetermined sensing cycle. In other words, in the example shown in FIG. 7, step S3 is performed at time t16, 10 ms after time t12. In the touch detection executed at time t16, as well, reverberation is still small, and the sensing portion 2a remains in a touched state, therefore the processing in the FIG. 6 flow is executed in the following order: step S3→S4→S5→S12.

In step S12, the "touch" state continuous time is measured. Specifically, at time t15 in FIG. 7, the elapsed time after fixing a "touch" determination is measured.

Next, in step S13, a determination is made of whether the continuous touch time measured in step S12 has exceeded 1 minute. If it does not exceed 1 minute, the system advances to step S11, and during the time a user is touching the sensing portion 2a, the processing in step S11→S2→S3→S4→S5→S12→S13→S11 is repeated. On the other hand, if more than 1 minute has elapsed, the system advances from step S13→S10, and the hot water electromagnetic valve 8a and cold water electromagnetic valve 8b are closed regardless of the faucet apparatus 1 state. I.e., a user touching the sensing portion 2a for more than 1 minute is an abnormal operation, and there is a high potential for false sensing of a touch, or of a failure. The hot water electromagnetic valve 8a and cold water electromagnetic valve 8b are therefore closed irrespective of the faucet apparatus 1 state, preventing water waste.

In addition, when a "no touch" is detected in the step S3 touch detection executed at time t17 in FIG. 7, it is confirmed that the user has removed his/her hand from the sensing portion 2a, and the determination output from the detection circuit 12 is changed to a "no touch" (time t18). However, the faucet apparatus 1 state continues to be switched (between the spouting or the shut off state) at time t15 in FIG. 7. Subsequent to time t18, in the FIG. 6 flow the processing in steps S3→S4→S11→S2→S3 are repeated until the sensing portion 2a is again touched by a user.

Thereafter if a user again touches the sensing portion 2a and this touch is confirmed, processing for the FIG. 6 flow is performed in the sequence of step S3→S4→S5→S6→S7→S8 to switch the state of the faucet apparatus 1 (returning to the state prior to time t15 in FIG. 7). Thus in the faucet apparatus 1 of the present embodiment, the spouting state and shut off state are alternately switched each time a user touches the sensing portion 2a (being the operation from the time a user touches until he removes his/her hand from the sensing portion 2a).

Next, referring to FIGS. 4, 5, and 8, we explain details of the touch detection executed in FIG. 6, step S3.

In the touch detection flow shown in FIG. 8, an AC voltage is applied to the piezo-electric element 4 for 1 ms, exciting the sensing portion 2a. Next, depending on the size of the reverberation during the 1 ms after stopping the application of an AC voltage, a determination is made of whether a user has touched the sensing portion 2a. Note that the touch detection flow shown in FIG. 8 is executed by the contact determination circuit 16a and anomaly sensing circuit 16c constituted by the microcomputer 16 and a program.

First, in FIG. 8 step S21, application of an AC voltage to the piezo-electric element 4 is started (time t1 in FIGS. 4 and 5). Next, in step S22, the value of variable n is reset to 1. In addition, in steps S23-S27, during application of the AC voltage, the signal conversion circuit 20 (FIG. 2) output voltage (bottom portion of FIGS. 4 and 5) is sampled and A/D converted 4 times every 250 μsec. By this means, during the 1 ms excitation period, 4 output voltage values $AD_{21}$, $AD_{22}$, $AD_{23}$, and $AD_{24}$ (bottom portion of FIGS. 4 and 5) are acquired from the signal conversion circuit 20.

Next, in step S28, the outputs from the microcomputer 16 (FIG. 2) ports P1 and P2 are respectively set to Hi and Lo, which results in turning off both the PNP transistor 18a and the NPN transistor 18b (termination of AC voltage output; time t2 in FIGS. 4 and 5). In step S29, the value of variable n is reset to 1. Furthermore, in steps S30-S34, immediately after stopping the application of the AC voltage, the signal conversion circuit 20 output voltage is sampled and A/D converted 4 times each 250 μsec. By this means, during the 1 ms excitation period, 4 output voltage values $AD_{11}$, $AD_{13}$, and $AD_{14}$ (bottom portion of FIGS. 4 and 5) are acquired from the signal conversion circuit 20.

Next, in step S35, a total SUM1 is calculated for the output voltage values $AD_{11}$, $AD_{12}$, $AD_{13}$, and $AD_{14}$ acquired in steps S30-S34. This SUM1 value is strongly correlated to the area of the diagonally shaded portion in FIGS. 4 and 5, and is a quantity indicating the reverberation energy of the sensing portion 2a vibration.

In addition, in step S36 an average value $SUM1_{AV}$ is calculated from each of the SUM1 values respectively calculated when the FIG. 8 flow chart is executed for the most recent 3 minutes. I.e., the $SUM1_{AV}$ is a moving average value for the last 3 minutes of SUM1. Here the time during which a user is touching the sensing portion 2a in a single operation is approximately 1 sec at the longest, therefore the majority of the SUM1 values calculated during the past 3 minutes may be assumed to have been acquired in the "no touch" state. Hence the $SUM1_{AV}$, which is the average of SUM1, indicates the size of the average reverberation energy in the "no touch" state.

Next, in step S3, the SUM1 and the $SUM1_{AV}$ values are compared. When SUM1 is greater than ½ $SUM1_{AV}$, the system advances to step S38. I.e., when SUM1 is greater than ½ $SUM1_{AV}$, the reverberation energy SUM1 detected in the current iteration differs greatly from the average reverberation energy $SUM1_{AV}$ in the "no touch" case, therefore in step S38 a "no touch" determination is made, and one iteration of the FIG. 8 flow chart processing is completed. This "no touch" determination is used for judging in the main flow (FIG. 6) step S4.

On the other hand when SUM1 has a value ½ or less of $SUM1_{AV}$, the system advances to step S39. I.e., when SUM1 is ½ or less of $SUM1_{AV}$, the reverberation energy SUM1 detected in the current iteration has dropped much more than the average reverberation energy $SUM1_{AV}$ in the "no touch" case, so there is a high potential that the sensing portion 2a has been touched. I.e., in the present embodiment, a determination is made of whether a "touch" of the sensing portion 2a has been made based on the sensing portion 2a vibration energy after the application of an AC voltage is stopped; when the vibration energy is at or below a predetermined threshold, it is determined that a "touch" has been made.

In step S39, the maximum and minimum values are extracted from the 4 output voltage values $AD_{21}$, $AD_{22}$, $AD_{23}$, and $AD_{24}$ acquired during application of an AC voltage.

In addition, a determination is made in step S40 of whether the value resulting from subtracting the minimum value from the maximum value extracted in step S39 is greater than a predetermined threshold value. If the value resulting from subtracting the minimum value from the maximum value is at or below a predetermined threshold value; the system advances to step S41; in step S41, a determination of "touch" is made, and one interaction of the FIG. 8 flow chart processing is completed. This "touch" determination is used for judging in the main flow (FIG. 6) step S4.

On the other hand if the value resulting from subtracting the minimum value from the maximum value extracted in step S39 is greater than a predetermined threshold value, the system advances to step S38; in step S38 a "no touch" determination is made, and one iteration of the FIG. 8 flow chart processing is completed. I.e., the anomaly sensing circuit 16c built into the microcomputer 16 senses an anomaly when the AC voltage varies by a predetermined value or more during application of an AC voltage to the piezoelectric element 4, and does not determine a "touch." Thus even if a determination is made that the reverberation energy SUM1 currently detected in step S37 has dropped, if the difference between the maximum value and minimum value in step S40 is greater than a predetermined value, a determination of "no touch" is made for reasons explained below.

Figure 9:
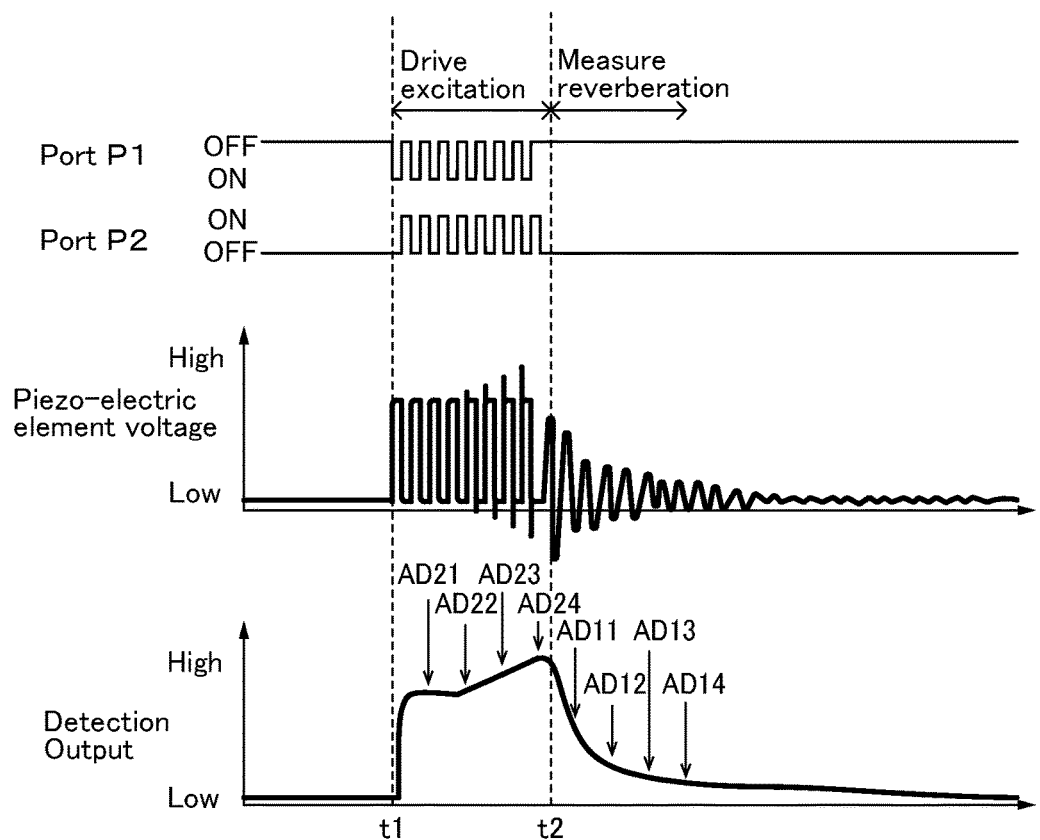
FIG. 9 A diagram showing an example of an output waveform when the sensing portion resonant frequency is very slightly offset from the frequency of the applied AC voltage.

FIG. 9 is diagram showing an example of an output waveform when the sensing portion 2a resonant frequency is very slightly offset from the frequency of the applied AC voltage. Note that FIG. 9 is a waveform showing the state whereby the sensing portion 2a is not being touched.

As explained above, the touch detection in a first embodiment of the invention applies an AC voltage at a frequency matching the sensing portion 2a and the piezo-electric element 4, which vibrate as a single unit, and determines whether a touch operation has occurred based on the reverberation vibration after application of the AC voltage has ended. In a touch detection device used in water handling equipment such as that in the present embodiment, however, water droplets frequently adhere to the sensing portion. The present inventors discovered that if water droplets do adhere in this manner, the resonant frequency of the sensing portion 2a and the piezo-electric element 4 drops slightly due to the mass of the adhered water droplets, adversely affecting the reliability of the determination.

The inventors discovered that when the resonant frequency of the faucet main body 2 and the piezo-electric element 4 in this way change, the resonant frequency and the frequency of the AC voltage applied to the piezo-electric element 4 become slightly offset, and what is known as the "harmonic beat" phenomenon occurs. This type of change in resonant frequency can also occur in cases such as when the sensing portion 2a temperature changes due to the effect of hot or cold water impinging on the sensing portion 2a. FIG. 9 is an example of the output waveform when the "buzzing" phenomenon occurs; in this case, the output waveform from the piezo-electric element 4 during application of the AC voltage differs from FIGS. 4 and 5.

We now explain the above-described phenomenon. When the sensing portion 2a and the piezo-electric element 4 are flexurally vibrating, an electromotive force is generated between the electrodes (between signal lines 4a, 4b) by the deformation of the piezo-electric element 4. This is the same as the state in which an AC voltage is applied to the input terminal (signal line 4a) relative to the piezo-electric element 4. However; if the resonant frequency of the sensing portion 2a and piezo-electric element 4 matches the frequency of the applied AC voltage, the PNP transistor 18a turns on at the timing when a negative electromotive force is produced on the piezo-electric element 4 input terminal (signal line 4a), and the NPN transistor 18b turns on at the timing when a positive electromotive force is produced. I.e., the ideal excitation state is one in which the AC voltage applied voltage and the voltage terminal electromotive force are in an opposite phase relationship. In that instance, since the impedance is lower than the piezo-electric element 4 impedance when the PNP transistor 18a and NPN transistor 18b are on, the waveform makes it appear that the piezo-electric element 4 input terminal (signal line 4a) is connected either to a power supply voltage or to ground.

In the output waveform shown in FIG. 9, the voltage waveform during application of an AC voltage has values which instantaneously exceed the power supply voltage at times when a pulse is rising. Similarly when a pulse is falling, it has instantaneous values at or below ground potential. This phenomenon arises because the sensing portion 2a and piezo-electric element 4 resonant frequency is slightly offset from the frequency of the applied AC voltage. When an AC voltage is applied to the sensing portion 2a and the piezo-electric element 4, a flexural vibration is produced at the natural resonant frequency. If an AC voltage completely opposite in phase to the electromotive force created by this flexural vibration is applied, the waveform is as shown in FIGS. 4 and 5 described above. However when water droplets adhere to the sensing portion 2a and the resonant frequency drops slightly, for example, the frequency on ports P1 and P2 output by the microcomputer 16 (FIG. 2) is fixed, so an AC voltage is applied at a higher frequency than the resonant frequency. This means that an offset arises in the timing at which the original anti-phase shifts to in-phase, whereby when the piezo-electric element 4 is still producing positive electromotive force the PNP transistor 18a turns on and a applies positive voltage, and when it is still producing a negative electromotive force, the NPN transistor 18b turns on and a negative voltage is applied.

For example, if the PNP transistor 18a turns on and the signal line 4a rises to a potential near the power supply voltage, and a positive voltage at the piezo-electric element 4 electromotive force is further applied thereto, a voltage exceeding the power supply voltage will be applied to the PNP transistor 18a collector. More specifically, the current resulting from the positive electromotive force on the piezo-electric element 4 flows from the collector to the base of the PNP transistor 18a (during this time it is a PN junction and therefore a forward diode), and further to the power supply side through the resistor 18c. Hence the PNP transistor 18a does not function as a transistor switch, and as shown in FIG. 9, a waveform exceeding the power supply voltage appears on the signal line 4a. The relationship between the negative electromotive force and the NPN transistor 18b is the same phenomenon as a polarity reversal. While the way in which timing is offset must conversely also be considered, the same phenomenon also occurs when the piezo-electric element 4 resonant frequency is high (generally a trend at low temperatures) as when the frequency is low, as described above.

Thus in cases where there is an offset between the resonant frequency and the frequency of the applied AC voltage, a phenomenon arises whereby the pulse waveform becomes chaotic during application of the AC voltage, and the amplitude changes. To prevent detection of a "touch" resulting in false sensing in such frequency offset states, a "no touch" determination is made when the difference between the maximum value and the minimum value during application of the AC voltage is greater than a predetermined threshold value in step S40 of FIG. 8.

Also, in the output waveform shown in FIG. 9, the distortion of the waveform appearing in the falling portion of the pulse waveform gradually increases. It is believed that the primary cause of this phenomenon is that the offset in the timing between the piezo-electric element 4 electromotive force and the applied AC voltage gradually increases due to the difference between the piezo-electric element 4 resonant frequency and the frequency of the applied AC voltage. An additional cause is believed to be that the piezo-electric element 4 vibration amplitude gradually increases after vibration by application of an AC voltage is started, so that the electromotive force produced increases. In the output waveform shown in FIG. 9, the reverberation vibration after application of an AC voltage is smaller than in FIG. 4, regardless of whether the sensing portion 2a has been touched. This is because the piezo-electric element 4 vibration amplitude is not sufficiently large, due to the offset between the resonant frequency of the sensing portion 2a and piezo-electric element 4, and the frequency of the AC voltage which excite these. Hence when a "touch" or "no touch" determination is made based on reverberation vibration in a state in which the resonant frequency and the AC voltage frequency are offset, there is risk of a false sensing.

The "touch confirming detection" processing executed in step S6 of FIG. 6 is processing devised to avoid this type of false sensing.

Figure 10:
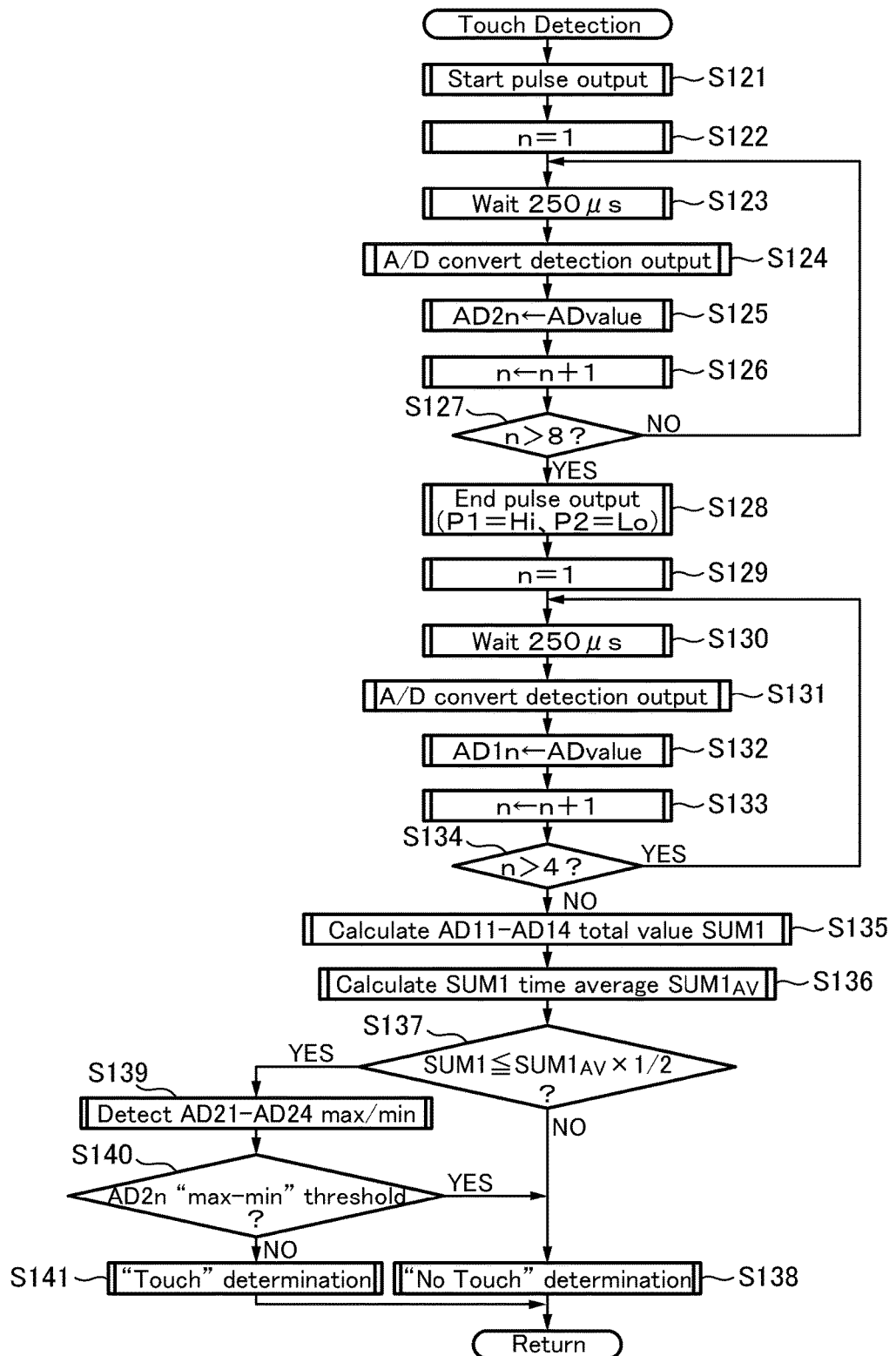
FIG. 10 A flow chart showing the touch confirming detection process called as a subroutine in step S6 of FIG. 6.
Figure 11:
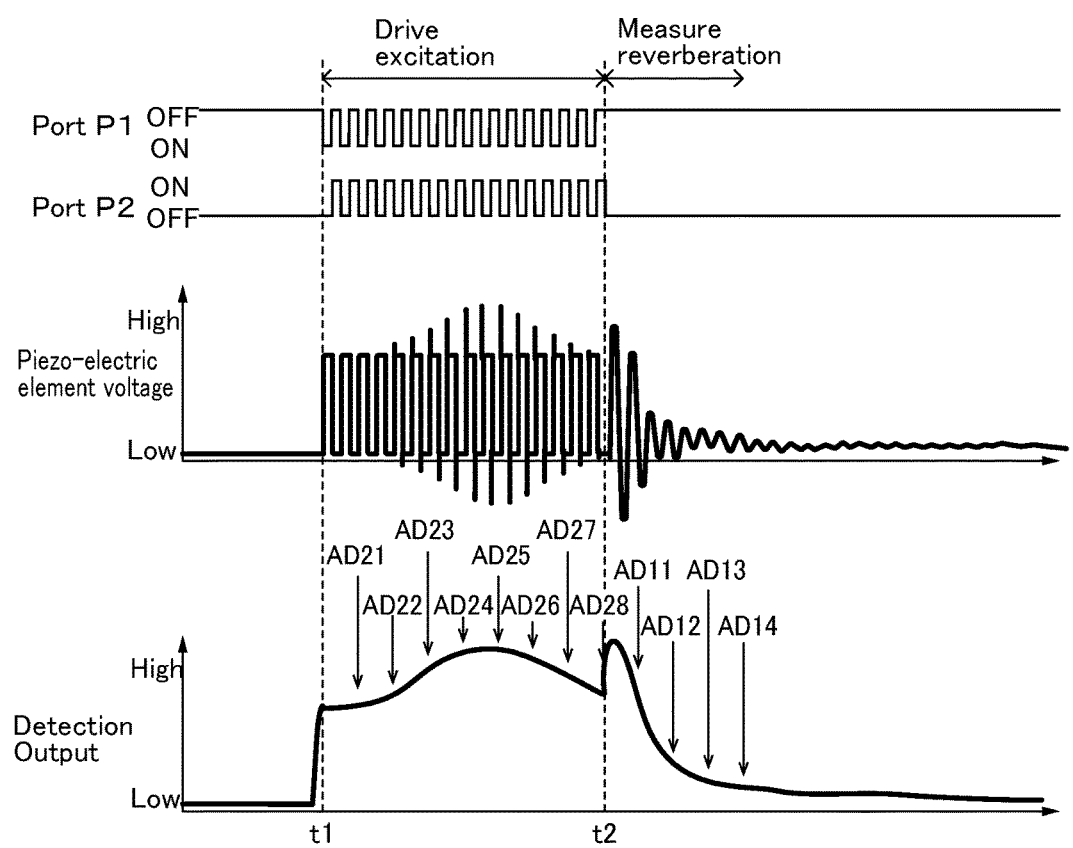
FIG. 11: A diagram showing an example of an output waveform when a touch confirming detection is performed in a state in which the sensing portion resonant frequency is slightly offset from the frequency of the applied AC voltage.

Next, referring to FIGS. 10 and 11, we explain touch confirming detection in detail. This "touch confirming detection" processing is executed as a contact confirmation determination after a user's "touch" has first been determined. Note that the touch confirming detection flow shown in FIG. 10 is executed by the contact determination confirming circuit 16b constituted by the microcomputer 16 and a program.

FIG. 10 is a flow chart showing the "touch confirming detection" processing called as a subroutine in step S6 of FIG. 6. FIG. 11 is a diagram showing an example of an output waveform when a touch confirming detection is performed with the sensing portion 2a resonant frequency slightly offset from the frequency of the applied AC voltage. Note that FIG. 11 is a waveform showing the state whereby the sensing portion 2a is not being touched.

Here the touch confirming detection flow chart shown in FIG. 10 is the same as the touch detection flow chart shown in FIG. 8 except for steps S127 and S139. I.e., in the "touch detection" shown in FIG. 8, an AC voltage was being applied over a 1 ms period, and 4 output voltage values $AD_{21}$ through $AD_{24}$ were being acquired every 250 μs during this period, whereas in the "touch confirming detection" shown in FIG. 10, an AC voltage is applied over a 2 ms period as a predetermined confirmation time, and 8 output voltage values $AD_{21}$ through $AD_{23}$ were being acquired every 250 μs during this period. In association with this, in step 139 the maximum and minimum values are extracted from among the 8 output voltage values $AD_{21}$ through $AD_{23}$, and in step S140, the difference between these are compared with a threshold value.

The output waveform obtained with this type of touch confirming detection is extended as shown in FIG. 11, with the AC voltage application time being the confirmation time, thereby making it easier to grasp the disturbance (change) in the pulse waveform amplitude during application of the AC voltage. Also, in the FIG. 11 output waveform the amplitude exceeding the power supply voltage in the pulse waveform temporarily increases, then diminishes. This is believed to result from the frequency offset between the frequency at which the sensing portion 2a and the piezo-electric element 4 vibrate and the frequency of the applied AC voltage, which causes the phase relationship of the two vibrations to change over time, so that when the polarity of the piezo-electric element 4 electromotive force matches the polarity of the drive circuit 18 output, i.e. when in the same phase (around $AD_{25}$ in the bottom portion of FIG. 11), the amplitude of the pulse waveform increases. If application of the AC voltage is continued further, as time elapses the timing at which the above-described same phase is reached returns to the reverse phase timing, which is the original timing for applying the AC voltage (around $AD_{23}$ in the bottom portion of FIG. 11). This is the reason for the "harmonic beat" phenomenon occurring in the waveform. Thus by setting a long AC voltage application time, increases in the pulse waveform amplitude during application of the AC voltage (during the confirmation period) can be detected, with the result that small offsets in the resonant frequency can be detected, and false determinations can be prevented.

Note that the AC voltage application time is 1 ms in FIG. 8, and double that or 2 ms in FIG. 10. In the present embodiment, however, when an AC voltage is applied at the resonant frequency of the sensing portion 2a and piezo-electric element 4, 1 ms is set as a sufficient time to reach a stable flexural vibration state. Therefore even if application of the AC voltage is increased to greater than 1 ms, the flexural vibration amplitude will not increase further. Hence the same processing as shown in FIGS. 8 and 10 is sufficient for determining the reverberation vibration after completion of application of an AC voltage.

In the present embodiment if no water droplets or the like are adhering to the sensing portion 2a, the sensing portion 2a can be vibrated at a sufficient vibration amplitude by the 1 ms excitation resulting from "touch detection" processing, so a "touch" can be detected. Hence, as shown in FIG. 7, in normal operations the "touch detection" processing must be performed every 10 ms, which is the sensing cycle, and when this processing results in a "touch" determination (times t12-t14 in FIG. 7), "touch confirming detection" processing is executed (times t14-t15 in FIG. 7), a "touch" detection is confirmed, and false sensing is prevented. The sensing portion 2a vibration time can in this way be minimized, electrical power required for vibration saved, and longevity of the piezo-electric element 4 extended.

In addition, in a state whereby water droplets or the like are adhered to the sensing portion 2a, when a user's hand has contacted the sensing portion 2a, the vibration amplitude of the sensing portion 2a (and the piezo-electric element 4) during application of an AC voltage to the piezo-electric element 4 is constrained, so that the electromotive force generated by piezo-electric element 4 also diminishes. For this reason, with a hand or the like on the sensing portion 2a, even when the sensing portion 2a and piezo-electric element 4 resonant frequency is offset from the frequency of the applied AC voltage, no disturbance of the pulse waveform occurs during application of the AC voltage (there is no major change in the pulse waveform amplitude resulting in the type of waveform shown in FIGS. 9, 11, etc.). Therefore in cases where the pulse waveform is disturbed during application of an AC voltage, even if a determination of "no touch" is made (FIG. 8, step S40; FIG. 10, step S140), reliable sensing can be accomplished when a user touch operation has occurred.

Next, referring to FIGS. 12 through 15, we explain the automatic adjustment of an AC voltage applied to the piezo-electric element 4.

Figure 12:
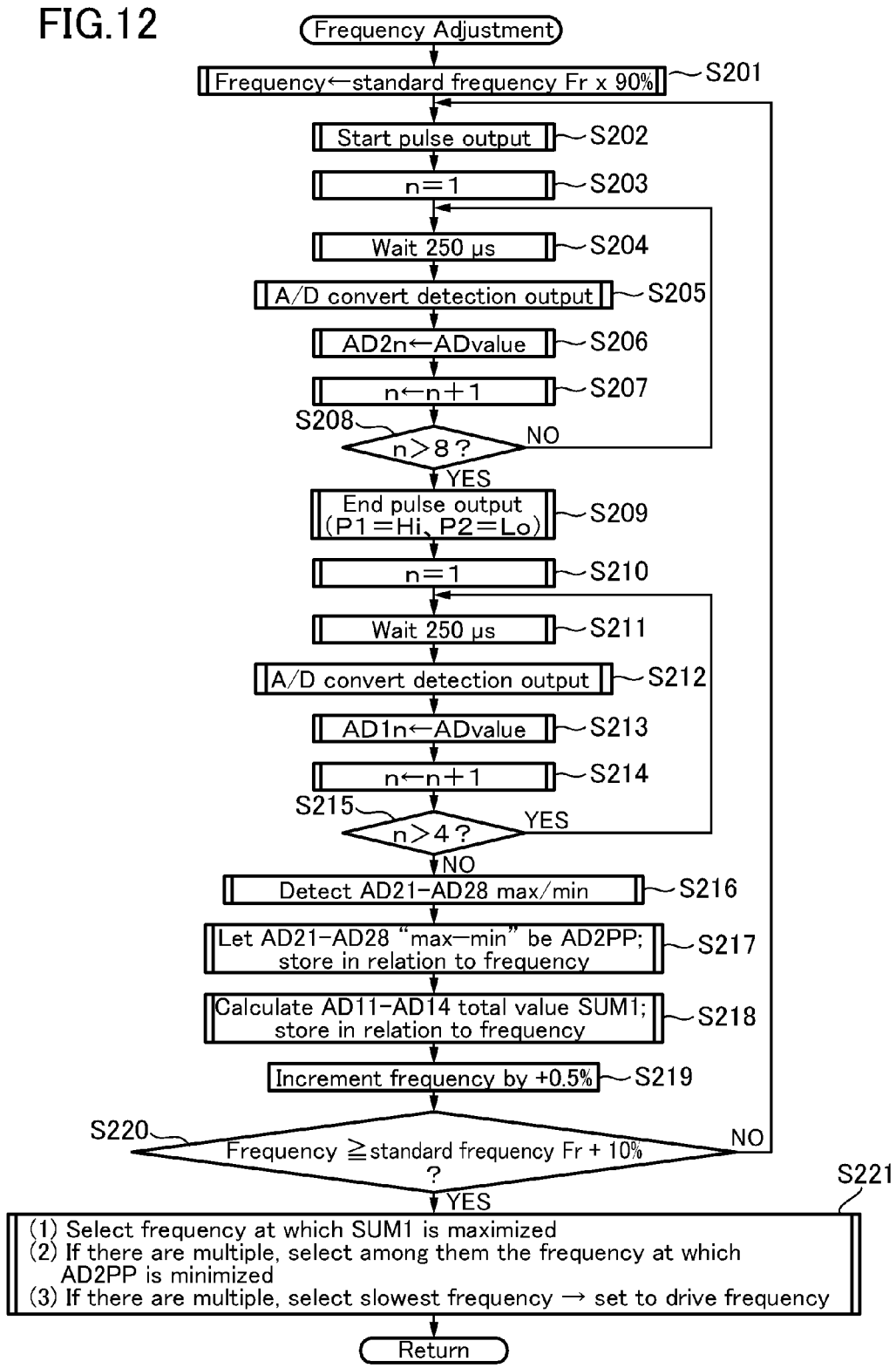
FIG. 12: A flow chart showing the frequency adjustment process called as a subroutine in step S1 of FIG. 6.
Figure 13:
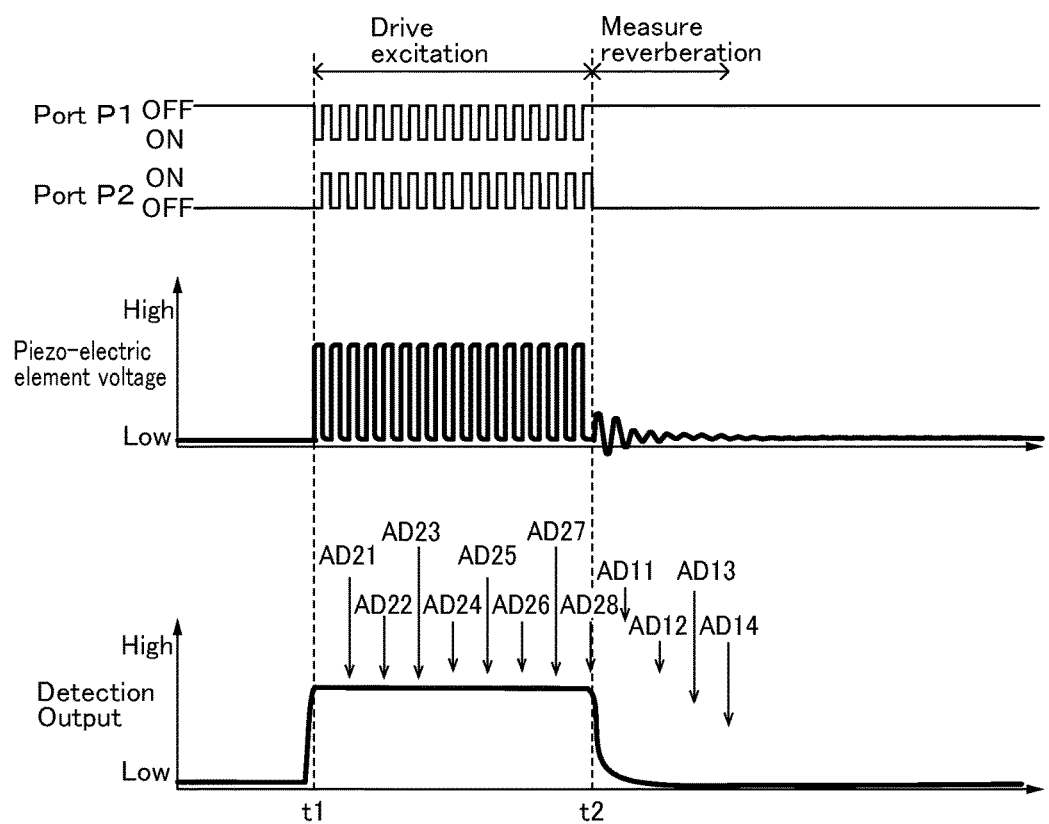
FIG. 13: An example of an output waveform when the sensing portion resonant frequency and the frequency of the applied AC voltage are relatively greatly offset.
Figure 14:
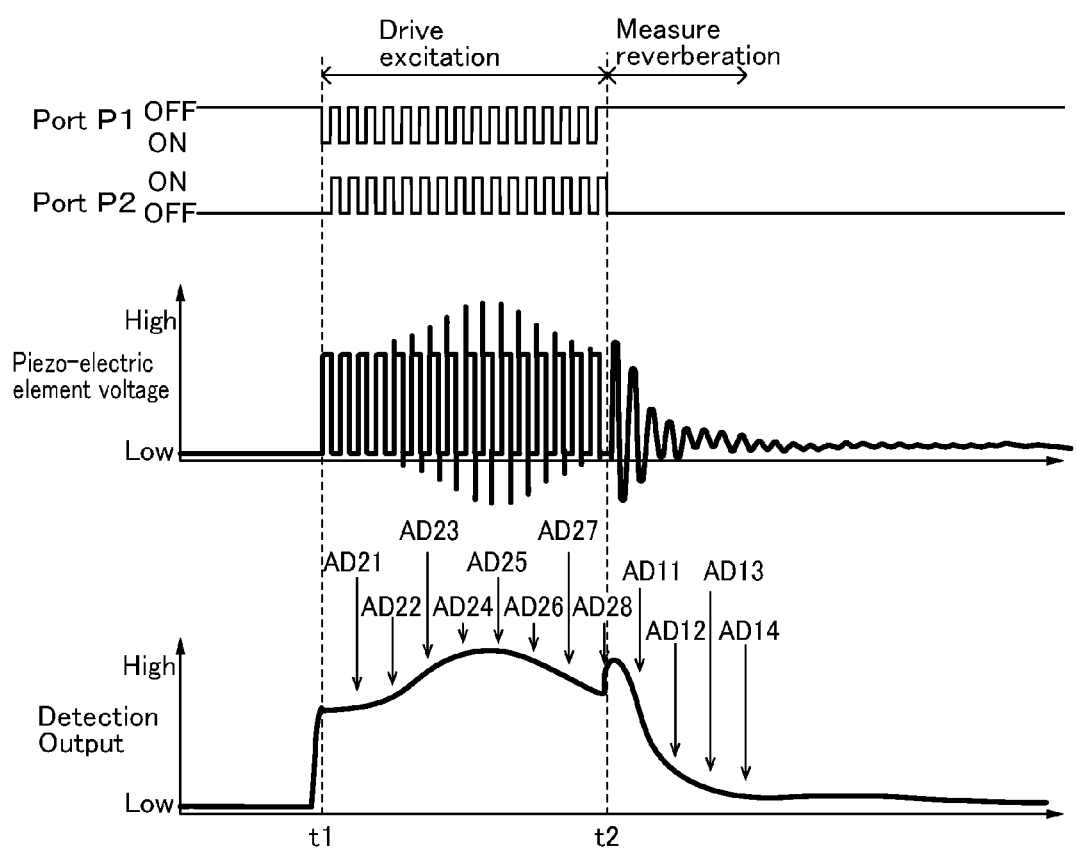
FIG. 14 An example of an output waveform when the sensing portion resonant frequency and the frequency of the applied AC voltage are slightly offset.
Figure 15:
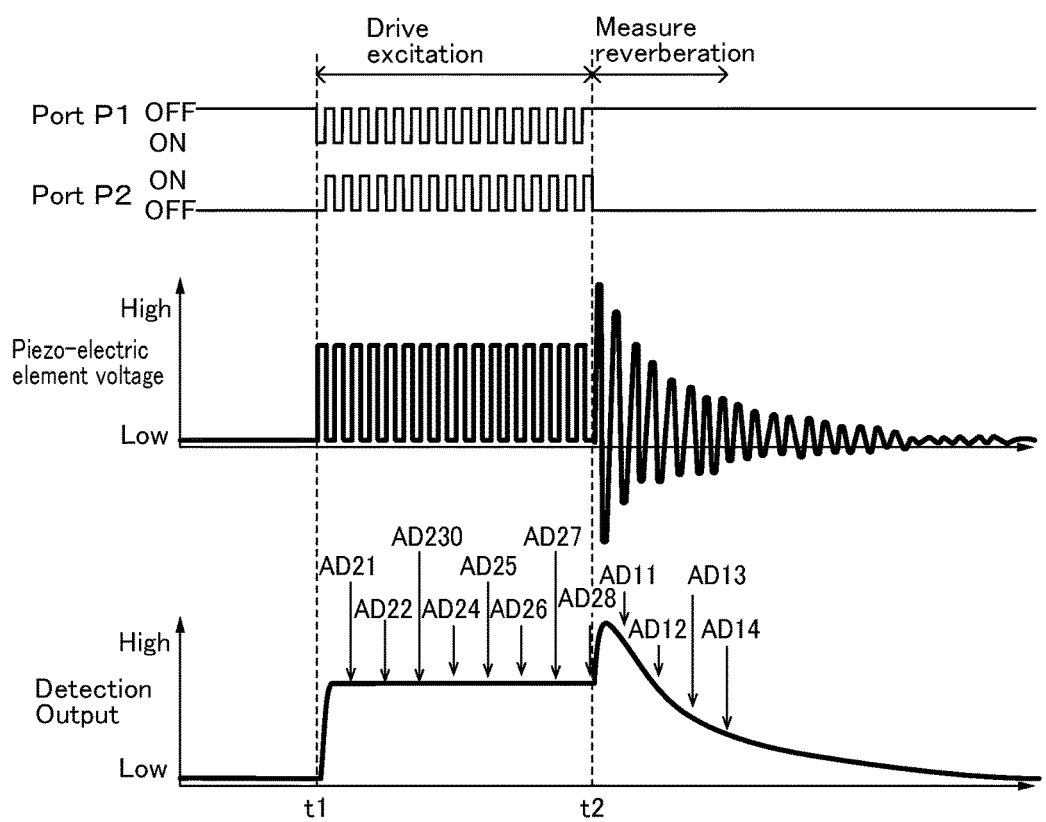
FIG. 15 An example of an output waveform when the sensing portion resonant frequency and the frequency of the applied AC voltage are fully matched.

FIG. 12 is a flow chart showing the "frequency adjustment" processing called as a subroutine in step S1 of FIG. 6. This "frequency adjustment" processing is executed by a frequency adjustment circuit 16d comprising the microcomputer 16 and a program. FIGS. 13 through 15 are diagrams showing the relationship of the sensing portion 2a resonant frequency and applied AC voltage frequency offset, to the outputted waveform. FIG. 13 is an example of an output waveform when the sensing portion 2a resonant frequency and the frequency of the applied AC voltage are relatively greatly offset. FIG. 14 is an example of an output waveform when the sensing portion 2a resonant frequency and the frequency of the applied AC voltage are slightly offset. FIG. 15 is an example of an output waveform when the sensing portion 2a resonant frequency and the frequency of the applied AC voltage are fully matched.

As described above, the resonant frequency of the sensing portion 2a and piezo-electric element 4, which vibrate as a single unit, must sufficiently match the frequency of the AC voltage to the piezo-electric element 4. However there are individual differences among sensing portions 2a and piezo-electric elements 4, and some degree of variability among the resonant frequencies thereof. It is therefore desirable to adjust the frequency of the AC voltage output by the detection circuit 12 (FIG. 2) to match the resonant frequency of the sensing portion 2a and the signal line 4a connected and used therewith. The detection circuit 12 built into the touch detection device of the present embodiment comprises a function for automatically adjusting the applied AC voltage frequency to match the resonant frequency of the connected sensing portion 2a and the piezo-electric element 4. Providing this function makes it possible to handle variability among sensing portions 2a and piezo-electric elements 4, and to handle aging-induced changes in resonant frequency, replacements of sensing portions 2a or piezo-electric elements 4 after product shipment, and so forth. In addition, a general purpose detection circuit, capable of being freely combined and used, can be constituted for multiple types of sensing portions and piezo-electric elements with differing basic design features, such as shape and dimension, or differing frequencies.

FIG. 12 is a flow chart showing "frequency adjustment" processing. In this "frequency adjustment" processing, an AC voltage is first applied to the piezo-electric element 4 over a 2 ms period, and 8 output voltage values $AD_{21}$ through $AD_{28}$ are acquired every 250 µs during this period (steps S202-S209 in FIG. 12); next, 4 output voltage values $AD_{11}$ through $AD_{14}$ in the reverberation vibration over the 1 ms following the end of voltage application are acquired every 250 µs (steps S210-S214). In addition, the value of the difference $AD_{2PP}$ between the maximum and minimum values of the output voltage values $AD_{21}$ through $AD_{28}$ acquired in this manner, and the total value of the output voltage values $AD_{11}$ through $AD_{14}$ are stored together with the frequency of the applied AC voltage (step S216-S218). Such applications of AC voltage and acquisitions of output voltage values are executed for multiple frequencies (steps S201, S219, S220), and the frequency closest to the resonant frequency is set as the frequency of the AC voltage to be applied for "touch detection" processing and "touch confirming detection" (step 221).

Specifically, the frequency of the AC voltage is varied in 0.5% increments within a ±10% range relative to the standard frequency Fr, which is the design value of the resonant frequency of the sensing portion 2a and piezo-electric element 4, and output voltage values (difference $AD_8$ between maximum and minimum values; and total value of $AD_{11}$ through $AD_{14}$) are stored.

FIGS. 13-15 are examples of the output waveform thus acquired.

First, when the resonant frequency of the sensing portion 2a and the piezo-electric element 4 is greatly offset from the applied AC voltage frequency, the reverberation vibration after stopping the application of the AC voltage becomes extremely small, as shown in FIG. 13. In such cases, the total value of the output voltage values $AD_{11}$ to $AD_{14}$ becomes extremely small. The amplitude of the pulse waveform during application of the AC voltage is also constant (the difference $AD_{2PP}$ between the output voltage value $AD_{21}$ to $AD_{28}$ becomes essentially 0). This is because the piezo-electric element 4 is not excited up to a very large amplitude even when an AC voltage is applied, due to the relatively large offset between the resonant frequency and the frequency of the applied AC voltage.

Next, as shown in FIG. 14, when the resonant frequency and the frequency of the applied AC voltage are slightly offset, the piezo-electric element 4 is excited to a relatively large amplitude by the application of an AC voltage. Therefore when the reverberation vibration after stopping the application of the AC voltage is large, the total value of output voltage values $AD_{11}$ through $AD_{14}$ is also relatively large. On the other hand, because of the tiny offset in phase between the vibration of the piezo-electric element 4 during application of an AC voltage and the AC voltage pulse waveform, part of the output voltage value increases (close to $AD_{25}$) during application of the AC voltage. The difference $AD_{2PP}$ between the maximum and minimum values of the output voltage values $AD_{21}$ through $AD_{25}$ in this way increases.

Also, as shown in FIG. 15, when the resonant frequency and the applied AC voltage frequency sufficiently match, the piezo-electric element 4 is greatly excited by the application of the AC voltage, therefore the reverberation vibration reaches a maximum after stopping of the AC voltage application, and the total of the output voltage values $AD_{11}$ to $AD_{14}$ also reaches a maximum. On the other hand, the relationship between the vibration of the piezo-electric element 4 during application of the AC voltage and the phase of the AC voltage pulse waveform is constant, so the amplitude of the pulse waveform during application of the AC voltage will not exceed the range of the power supply voltage. The difference $AD_{2PP}$ between the maximum and minimum values of the output voltage values $AD_{21}$ through $AD_2$ in this way decreases.

In step S221 of the FIG. 12 flow chart, the properties described above are utilized to find the resonant frequency of the sensing portion 2a and the piezo-electric element 4. Specifically, first of all, the frequency at which reverberation vibration (the total of output voltage values $AD_{11}$ to $AD_{14}$) was maximized is selected as the resonant frequency. Next, in cases where there are multiple frequencies at which reverberation vibration is maximized, the frequency at which the difference $AD_{2PP}$ between the maximum and minimum values is smallest is selected as the resonant frequency. If there are multiple equivalent frequencies for both the reverberation vibration and the difference $AD_{2PP}$ between the maximum and minimum values, the lowest frequency among them is selected as the resonant frequency. This is because when the resonant frequency at which the piezo-electric element 4 impedance is extremely small and the anti-resonant frequency at which that impedance is extremely high are in close proximity, the resonant frequency appears on the low frequency side.

Using the touch detection device of a first embodiment of the invention, a determination of contact by a user's hand with the sensing portion 2a is made based on vibration of the sensing portion 2a after application of an AC voltage is stopped (time t2 forward in FIGS. 4 and 5), therefore the vibration on the sensing portion 2a changes with even a light "touch" thereof, and a "touch" can be reliably sensed. Since the piezo-electric element 4 is attached in order to vibrate the sensing portion 2a, no circuit is required and no false operations occur even the piezo-electric element 4 is disposed at a location separate from the drive circuit 18 or the contact determination circuit 16a, etc. Thus the detection circuit 12 can be freely disposed, and water handling equipment with high design characteristics can be configured.

Using the touch detection device of the present invention, the vibration excitation element comprises a piezo-electric element, so the vibration excitation element can be constituted by a simple structure. Since the contact determination circuit 16a determines contact by a user's hand or the like with the sensing portion 2a based on an output signal from the piezo-electric element 4, vibration in the sensing portion 2a can be detected without providing separate elements or devices for detecting the vibration of the sensing portion 2a, so the constitution of the touch detector can be simplified.

Moreover, using the touch detection device of the present embodiment, an output signal is obtained from the signal line 4a which applies an AC voltage to the piezo-electric element 4, therefore the wiring for applying the AC voltage and at least a part of the wiring for obtaining an output signal can be shared, enabling the signal line wiring 4a to be simplified. Also, since the output of the drive circuit 18 goes to high impedance after application of the AC voltage is stopped (time t2 forward in FIGS. 4 and 5), a fully accurate output signal can be obtained even when the impedance of the output signal from the vibration excitation element 4 is high.

Also, using the touch detection device of the present embodiment, the PNP transistor 18a detects a touch based on the vibration energy in the sensing portion 2a (the shaded area in FIGS. 4 and 5; SUM1 in FIG. 8) after application of an AC voltage is stopped (time t2 forward in FIGS. 4 and 5), therefore even a tiny attenuation of vibration caused by touching with a hand or the like can be reliably captured, and a highly sensitive touch detection device can be constituted.

In addition, using the touch detection device of the present embodiment, the anomaly sensing circuit 16c senses anomalies (steps S39 and S40 in FIG. 8) based on the output signals (output voltage values $AD_{21}$ to $AD_{24}$ in FIG. 8) during application of an AC voltage to the piezo-electric element 4 (times t1-t2 in FIG. 9), therefore anomalies can be sensed without complicating the touch detection steps, and the occurrence of false sensing can be constrained.

In addition, using the touch detection device of the present embodiment, the anomaly sensing circuit 16c senses anomalies (steps S39 and S40 in FIG. 8) based on fluctuations in output signal amplitude (the value of the maximum value minus the minimum value of output voltage values $AD_{21}$ to $AD_{24}$) during application of an AC voltage (times t1-t2 in FIG. 9), therefore the occurrence of anomalies can be reliably sensed, and false operations due to false sensing can be prevented.

Furthermore, using the touch detection device of the present embodiment the contact determination confirming circuit 16b executes a contact determination confirmation operation (step S6 in FIG. 6; FIG. 10) after contact by a hand or the like has first been determined by the contact determination circuit 16a (steps S3, S4 in FIG. 6), therefore false sensing can be more reliably prevented. The contact determination confirmation operation is executed after target object contact has first been determined by the contact determination circuit 16a, therefore an unnecessary contact determination confirmation operation can be prevented, with no risk of false sensing (FIG. 6 steps S4→S11, steps S5→S12).

Also, using the touch detection device of the present embodiment, an AC voltage is applied in the contact determination confirmation operation (step S6 in FIG. 6) to the piezo-electric element 4 for a longer than normal predetermined confirmation period (times t1 to t2 in FIG. 11), therefore anomalies during application of an AC voltage can be more reliably detected.

In addition, using the touch detection device of the present embodiment the frequency adjustment circuit 16d adjusts the frequency of the AC voltage applied to the frequency at which the sensing portion 2a, with piezo-electric element 4 attached, resonates (FIG. 15). Since the sensing portion 2a vibrates at the resonant frequency, the sensing portion 2a can be made to vibrate at a large amplitude using a small excitation force, and the touch detector can be activated with little energy consumed.

Using the touch detection device of the present embodiment, the frequency adjustment circuit 16d applies an AC voltage multiple times at different frequencies for a predetermined time (times t1 to t2 in FIGS. 13 through 15) and decides the frequency at which the output signal from the piezo-electric element 4 reaches its maximum amplitude after stopping application of the AC voltage (time t2 forward in FIGS. 13 through 15) as the frequency at which a sensing portion 2a with a piezo-electric element 4 attached resonates (step S221 in FIG. 12). In the invention thus constituted, the frequency of the AC voltage can also be adjusted after installing the sensing portion 2a and the vibration excitation element into water handling equipment, therefore the frequency of the applied AC voltage can be matched to the resonant frequency even when the resonant frequency has been offset due to the passage of time.

In addition, in the touch detection device of the present embodiment when there are multiple existing frequencies for which the output signal amplitude is maximized after stopping application of an AC voltage (time t2 forward in FIGS. 13 through 15), the frequency adjustment circuit 16d decides on the frequency at which, of those frequencies at which amplitude was maximized, fluctuations in output signal amplitude during application of an AC voltage to the piezo-electric element 4 were smallest, as the frequency at which a sensing portion 2a with a piezo-electric element 4 attached resonates (FIG. 12, Step S221). Hence the frequency of a sensing portion 2a with a piezo-electric element 4 attached is reliably sent in an automatic manner by a simple algorithm.

Next, referring to FIGS. 16 through 21, we explain the operation of a faucet apparatus 1 according to a second embodiment of the invention.

In the faucet apparatus of the present embodiment, only the "touch detection" processing and the "touch confirming detection" processing called as respective subroutines from the main flow steps S3 and S6 in FIG. 6 differ from the first embodiment described above. Therefore here we explain only the aspects of the second embodiment of the invention different from the first embodiment of the invention, and we omit an explanation of similar parts.

Figure 16:
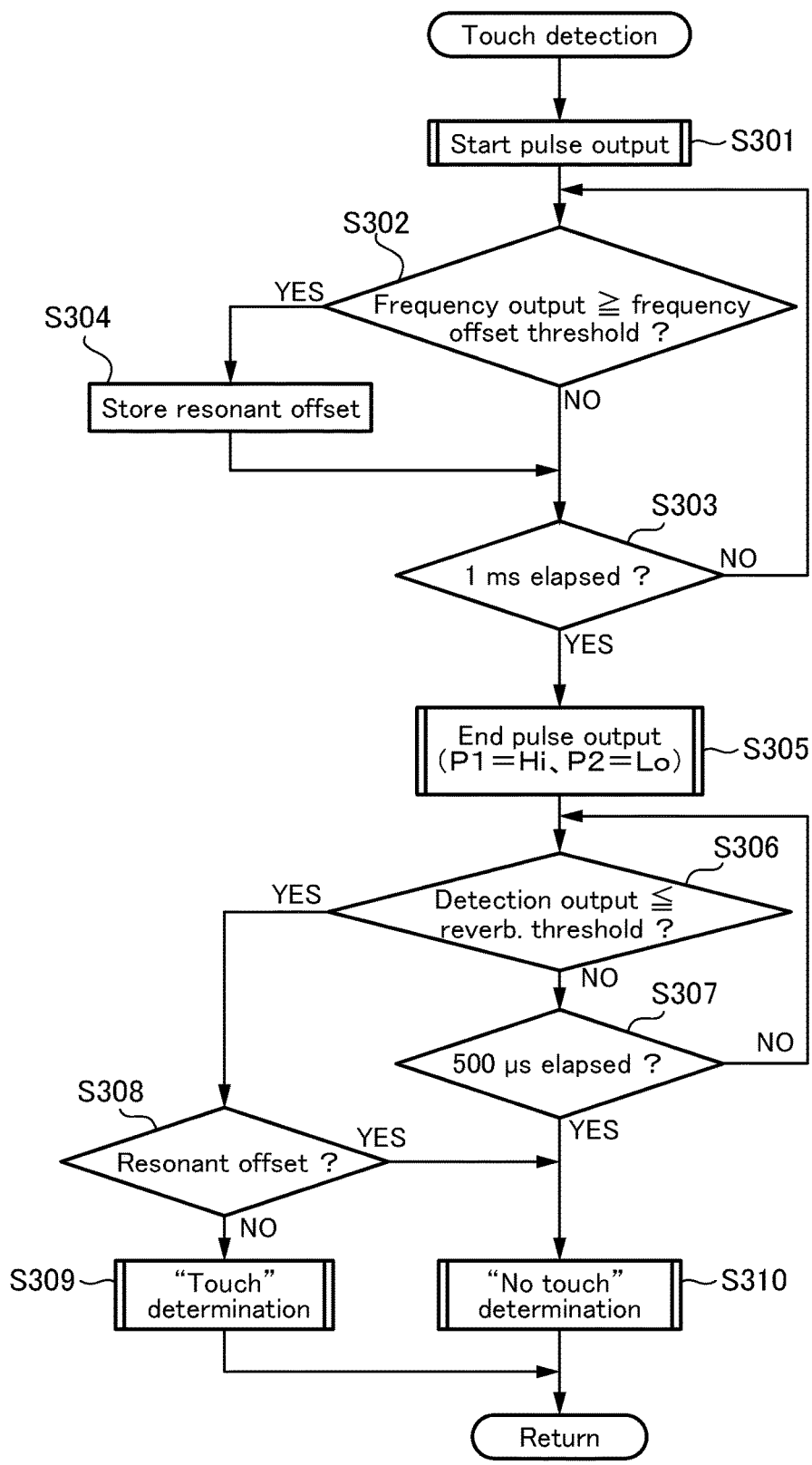
FIG. 16 A touch detection flow called as a subroutine from the main flow in FIG. 6 in a second embodiment of the invention.
Figure 17:
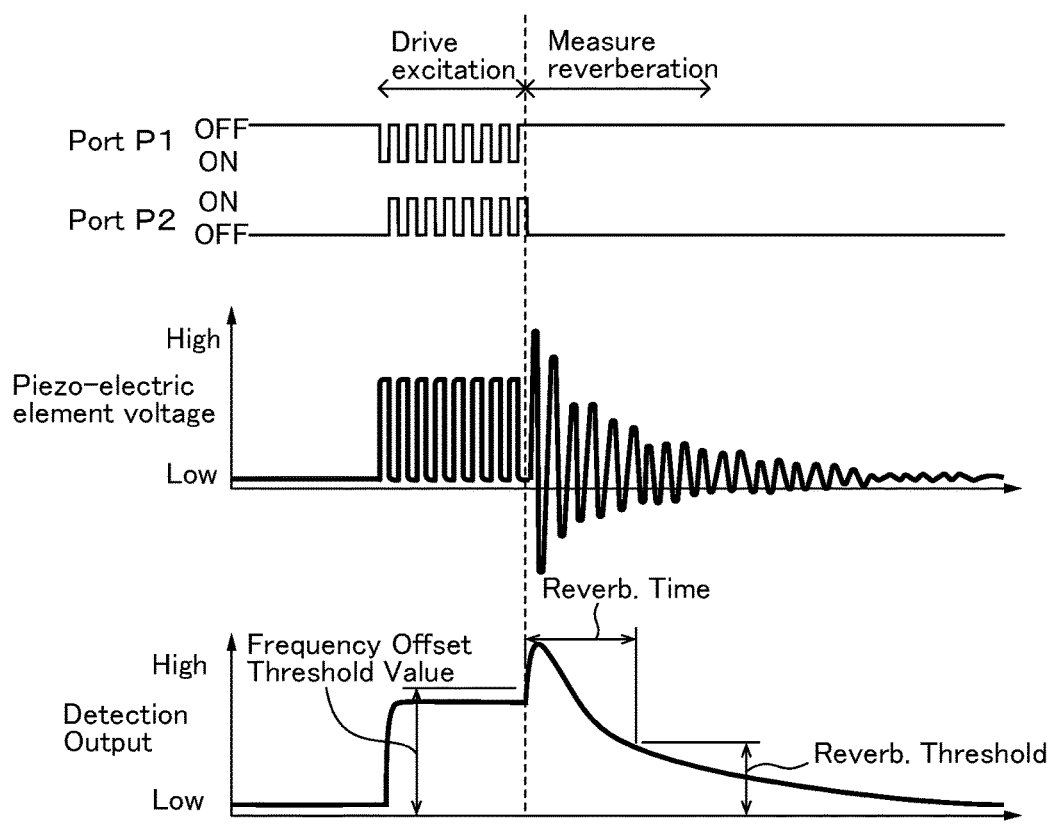
FIG. 17 A diagram showing a typical output waveform at a piezoelectric element when a user is not touching the sensing portion in a second embodiment touch detection device of the invention.
Figure 18:
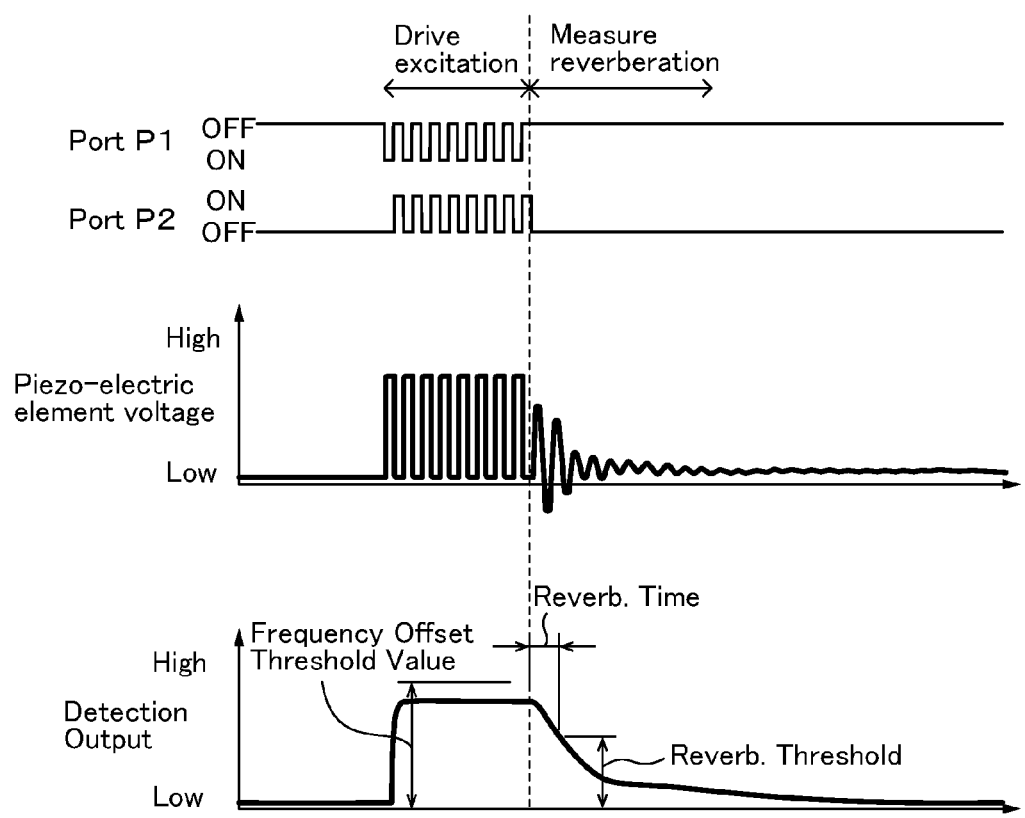
FIG. 18 A diagram showing a typical output waveform at a piezo-electric element when a user is touching the sensing portion in a second embodiment touch detection device of the invention.
Figure 19:
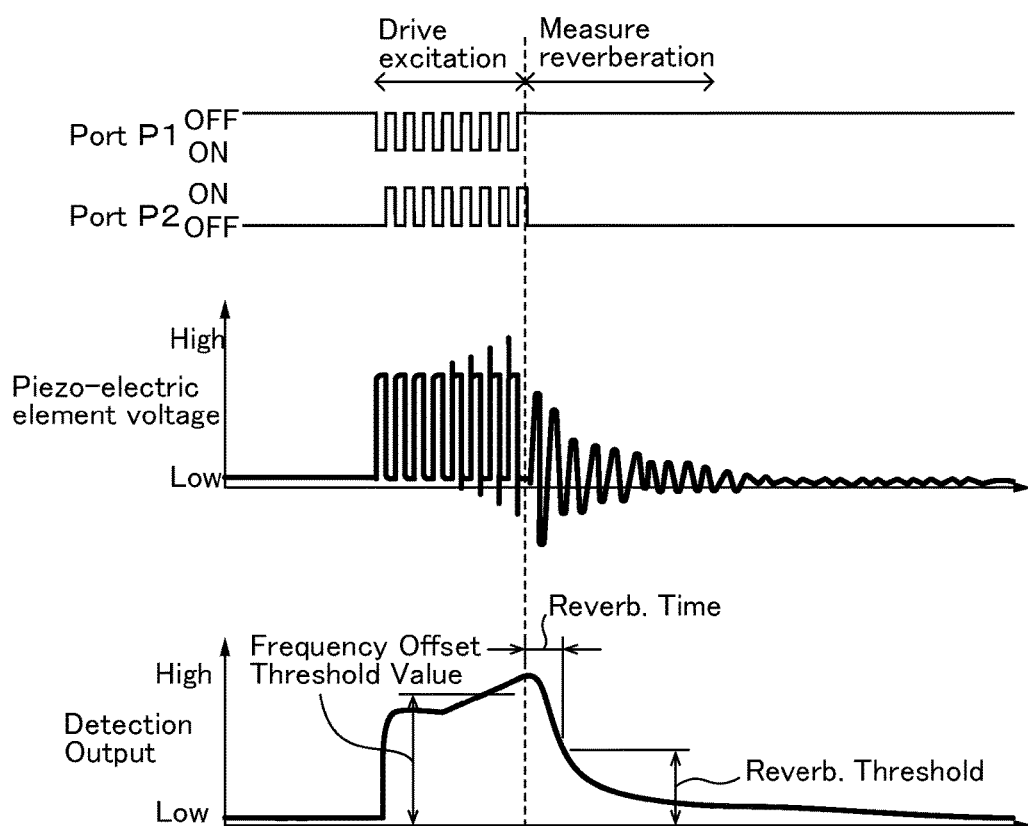
FIG. 19 A diagram showing an example of an output waveform when the sensing portion resonant frequency is very slightly offset from the frequency of the applied AC voltage.
Figure 20:
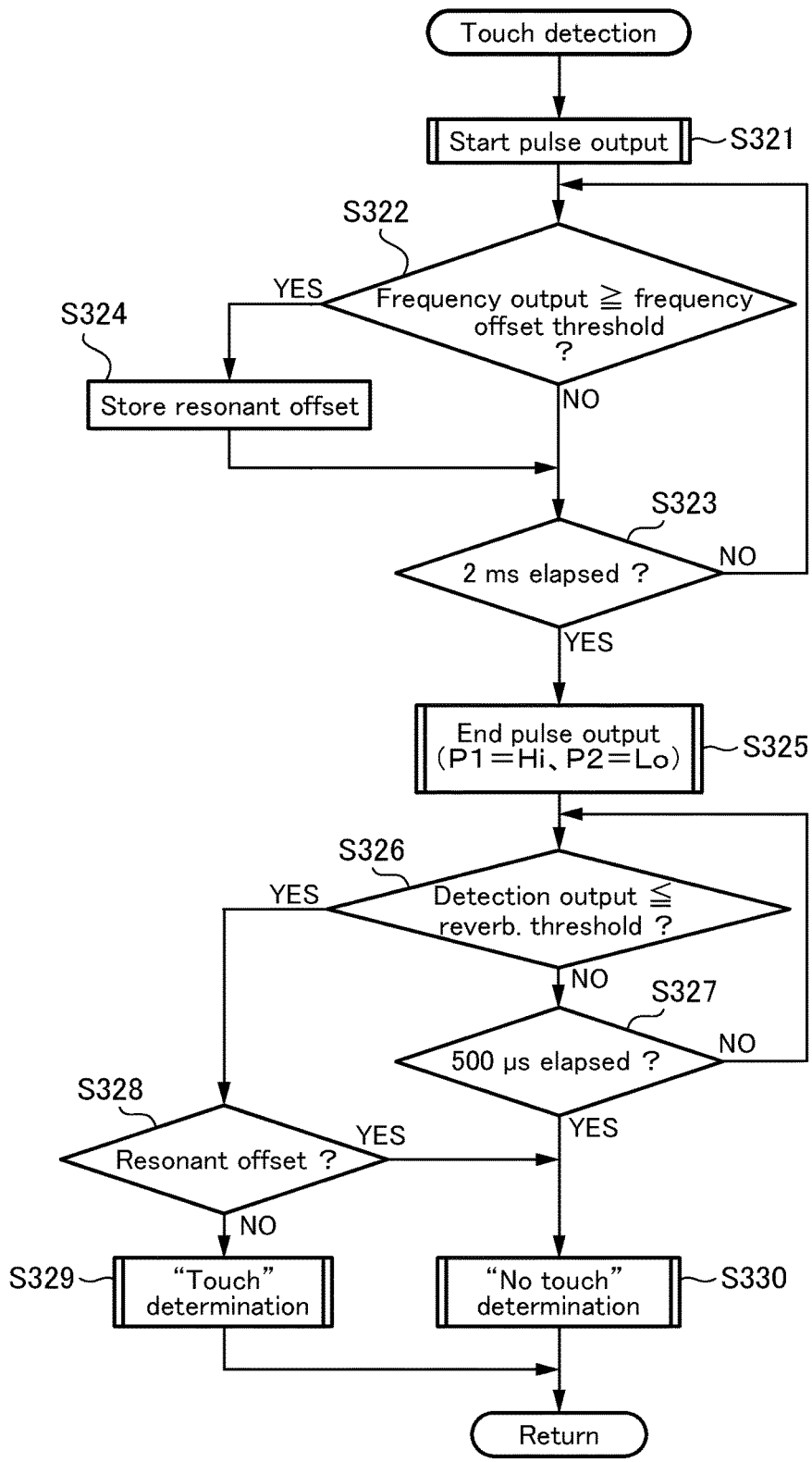
FIG. 20 A touch confirming detection flow called as a subroutine from the main flow in FIG. 6 in a second embodiment of the invention.
Figure 21:
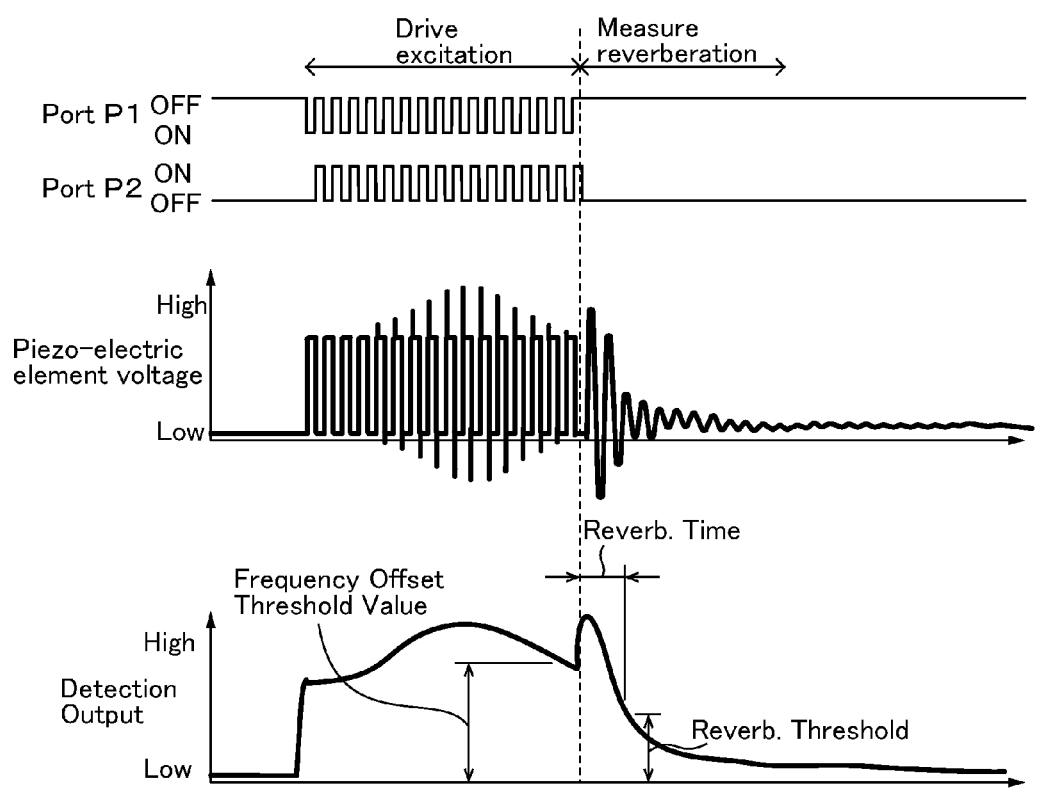
FIG. 21 A diagram showing an example of an output waveform when a touch confirming detection is performed in a state in which the sensing portion resonant frequency is slightly offset from the frequency of the applied AC voltage.

FIG. 16 is a touch detection flow called as a subroutine from the main flow in FIG. 6 in a second embodiment of the invention. FIG. 17 is a diagram showing a typical output waveform at a piezo-electric element when a user is not touching the sensing portion in a second embodiment touch detection device of the invention. FIG. 18 is a diagram showing a typical output waveform at a piezoelectric element when a user is touching the sensing portion in a second embodiment touch detection device of the invention. FIG. 19 is a diagram showing an example of an output waveform when the sensing portion resonant frequency is very slightly offset from the frequency of the applied AC voltage. FIG. 20 is a touch confirming detection flow called as a subroutine from the main flow in FIG. 6 in a second embodiment of the invention. FIG. 21 is a diagram showing an example of an output waveform when a touch confirming detection is performed with the sensing portion resonant frequency slightly offset from the frequency of the applied AC voltage.

In the touch detection device of the present embodiment, the FIG. 16 flow chart is executed as a subroutine performing "touch detection" processing.

First, application of the AC voltage to the piezoelectric element 4 is started at step S301. Next, in step S302, a determination is made of whether the envelope detection output (output from the signal conversion circuit 20) is at or above a predetermined "frequency offset threshold;" this processing is repeated until 1 ms has elapsed after starting the application of an AC voltage (steps S303, 305). If the detection force reaches the "frequency offset threshold" or above during application of an AC voltage, the system advances to step S304, and the fact that the threshold was exceeded is stored.

As shown in Fig. in the bottom portion of FIGS. 17 and 18, the "frequency offset threshold" is set to a value slightly greater than the normal envelope detection output when the sensing portion 2a resonant frequency matches the frequency of the applied AC voltage. I.e., as described in the first embodiment, when the sensing portion 2a resonant frequency and the frequency of the applied AC voltage match sufficiently, the pulse waveform amplitude during application of an AC voltage (during excitation) is almost the same as the power supply voltage (middle portion of FIGS. 17 and 18), and the fact that this envelope-detected pulse waveform is output from the signal conversion circuit 20. On the other hand, as shown in the middle portion section of FIG. 19, when the sensing portion 2a resonant frequency is offset from the frequency of the applied AC voltage due to adhesion or the like of water droplets to the sensing portion 2a, the pulse waveform amplitude during AC voltage application becomes larger than normal operation amplitude, with a part exceeding the power supply voltage range. Thus, as shown in the bottom section of FIG. 19, the output from the signal conversion circuit 20 exceeds the "frequency offset threshold."

Next, in step S306, a determination is made of whether the envelope detection output (the output from the signal conversion circuit 20) after stopping the application of an AC voltage has fallen to a predetermined "reverberation threshold" or below. This processing is repeated until 50 μsec have elapsed after stopping the application of the AC voltage (step S307). Note that, as shown in FIGS. 17 through 19, in the present embodiment the "reverberation threshold" is set to be approximately 50% of the normal envelope detection output.

Before 500 μs have passed after stopping the application of an AC voltage, the system advances to step S308 when the envelope detection output drops to the "reverberation threshold" or below; on the other hand if the envelope detection output does not drop below the "reverberation threshold" despite the elapse of 500 μs after stopping the application of an AC voltage, the system advances to step S310. In step S310, a determination is made that no user's hand or the like is touching the sensing portion 2a, i.e., of "no touch." This determination is made because in the "no touch" case, the reverberation vibration is large after stopping the application of an AC voltage, and a relatively large vibration remains even after 500 μs elapse following that stoppage.

In step S308, on the other hand, during application of an AC voltage a judgment is made that the envelope detection output is equal to or above the "frequency offset threshold;" when equal to or above the "frequency offset threshold," the system advances to step S310, and a "no touch" determination is made. This is because when the sensing portion 2a resonant frequency is offset from the frequency of the applied AC voltage, reverberation vibration is small even for a "no touch," and the reverberation vibration quickly drops to the "reverberation threshold" or below, so a "no touch" determination is made, and false sensing is prevented. As explained in the first embodiment, when a user "touches," the envelope detection output does not equal or exceed the "frequency offset threshold" even if water droplets or the like adhere to the sensing portion 2a, therefore a "touch" determination can be made even if water droplets or the like are adhering.

If the envelope detection output does not become equal to or greater than the "frequency offset threshold" during application of an AC voltage, the system advances from step S308 to step S309, and a determination is made that a user has touched the sensing portion 2a with a hand or the like, i.e., that a "touch" has occurred. This is because when a user has "touched," the reverberation vibration is small, and reverberation vibration drops at an early stage to the "reverberation threshold" or below. Thus after stopping the application of an AC voltage, if a vibration amplitude attenuates to a predetermined amplitude or below after elapse of a predetermined time, a "touch" determination is made.

Next, referring to FIGS. 20 and 21, we explain touch confirming detection in a second embodiment of the invention.

FIG. 20 is flow chart showing the "touch confirming detection" processing called as a subroutine in step S6 of FIG. 6. FIG. 21 is a diagram showing an example of an output waveform when a touch confirming detection is performed in a state in which the sensing portion 2a resonant frequency is slightly offset from the frequency of the applied AC voltage. Note that FIG. 21 is a waveform of the state whereby the sensing portion 2a is not being touched.

Here the touch confirming detection flow chart shown in FIG. 20 is identical to the touch detection flow chart shown in FIG. 16 except that its step S323 differs from step S303 in FIG. 16. I.e., whereas the AC voltage was applied for 1 ms in the "touch detection" processing shown in FIG. 16, the AC voltage is applied for 2 ms in the "touch confirming detection" processing shown in FIG. 20.

As shown in FIG. 21, when an AC voltage is applied over a 2 ms period, disturbance of the pulse waveform during application of the AC voltage can be more accurately detected, and an accurate determination can be made of whether the "frequency offset threshold" is exceeded during application of the AC voltage. Thus by extending the AC voltage application time, the offset between the sensing portion 2a resonant frequency and the frequency of the applied AC voltage can be accurately detected, and false sensing can be prevented.

Also, in the above-described second embodiment, a "touch" or "no touch" determination can be made based on whether the time for the envelope detection output (the output from the signal conversion circuit 20) to drop to a predetermined "reverberation threshold" or below is 500 μs or less after stopping the application of AC voltage. Thus as shown in the first embodiment, a "touch" or "no touch" determination can be made using a microcomputer, without performing an integration calculation (processing to obtain a total of multiple A/D conversion values) on output values from the signal conversion circuit 20. In the second embodiment, for example, a determination can be made using a timer to measure the time after stopping the application of an AC voltage, and a comparator for detecting whether an envelope detection output has dropped to a level equal to a "reverberation threshold" or less. I.e., by measuring the time until detection of the comparator drops to the "reverberation threshold," a determination can be made of "touch" or "no touch." This enables the detection circuit to be simplified.

In addition, in the above-described second embodiment, a determination was made based on the time required for the envelope detection output to drop to a predetermined "reverberation threshold" or below, but as a variant example, a "touch" or "no touch" determination can also be made by measuring the envelope detection output upon the elapse of a predetermined time after stopping the application of AC voltage, and based on whether the envelope detection output reaches predetermined threshold value or below. I.e., a "touch" determination is made if a vibration amplitude attenuates to a predetermined amplitude or below upon the elapse of a predetermined time after stopping the application of an AC voltage. In this variant example, a determination can be made with a computer and a timer, and can be performed with a simple circuit.

Next, referring to FIGS. 22 through 32, we explain a faucet apparatus 1 according to a third embodiment of the invention.

The faucet apparatus of the present embodiment differs from the first embodiment only with respect to the detection circuit constitution and effect. Therefore here we explain only the aspects of the third embodiment of the invention different from the first embodiment of the invention, and we omit an explanation of similar parts.

In the above-described invention, the first and second embodiments are touch detection devices used in a water handling apparatus; an AC voltage at a frequency matching the sensing portion 2a resonant frequency is intermittently applied, and sensing of contact by user's hand, etc. with the sensing portion 2a was based on sensing portion 2a reverberation vibration (FIG. 4) after stopping the application of AC voltage. I.e., determination of a "touch" to the sensing portion 2a is made based on the characteristic that when a user's hand contacts the sensing portion 2a, reverberation vibration diminishes (FIG. 5).

Also, in the above-described first and second embodiments of the invention, when the amplitude of the output signal from the piezo-electric element 4 increases during application of an AC voltage (FIG. 9), the sensing portion 2a resonant frequency changes due to factors such as temperature changes and adhesion of water droplets; a determination is made that an offset has occurred relative to the frequency of the AC voltage applied to the piezo-electric element 4; and a "touch" determination is not made even if reverberation is decreasing.

In addition, the frequency of the applied AC voltage is varied and the size of the reverberation is measured; the frequency at which this is maximized is assumed to be the sensing portion 2a resonant frequency, and the AC voltage frequency is automatically adjusted accordingly (FIG. 12).

Automatically adjusting the frequency of the applied AC voltage enables variability and fluctuations etc. in the sensing portion 2a or the detection circuit 12 to be absorbed so that the AC voltage frequency can be matched to the resonant frequency. However in some cases automatic frequency adjustment cannot be accurately performed, depending on factors such as the environment in which the adjustment is performed. By automatically adjusting the frequency prior to factory shipment, the adjustment environment can be matched to certain conditions, thereby enabling accurate adjustment to be made. Considering aging-induced changes in the sensing portion 2a resonant frequency, or replacements of failed sensing portions 2a, it is desirable to also be able to perform automatic adjustment at the site where the faucet apparatus is actually used.

Thus in some cases conditions for accurate adjustment are difficult when performing automatic frequency adjustment on site, such as when a user is touching the sensing portion during the automatic adjustment, or water droplets are adhered to the sensing portion 2a, or the sensing portion 2a is in contact with hot water or ice, and at an extremely high or low temperature. It is also conceivable that electrical noise may accidentally interfere during automatic adjustment, introducing errors into the adjustment results.

Changes in resonant frequency caused by adhesion of water droplets or extreme high or low temperatures are temporary events; falling off or evaporation of water droplets or a return of the sensing portion 2a temperature to room temperature result in restoration of the resonant frequency to a normal value. Therefore the appropriate way to handle an offset between the applied AC voltage frequency and the resonant frequency is depends on the root cause thereof. Operation of the touch detection device can actually become unstable if automatic adjustments are performed frequently to change AC voltage frequency in response to temporary changes in resonant frequency. Also, when automatic adjustments are performed frequently, usability of the touch detection device degrades, since no touch detection can be performed during that interval.

In addition, water droplets frequently adhere to the sensing portion 2a of the water handling equipment. Therefore when an offset occurs between the frequency of the applied AC voltage and the resonant frequency, it is desirable to prevent false "touch" sensing, and not wait to perform an automatic adjustment.

The faucet apparatus of a third embodiment of the invention has the object of solving these problems.

Figure 22:
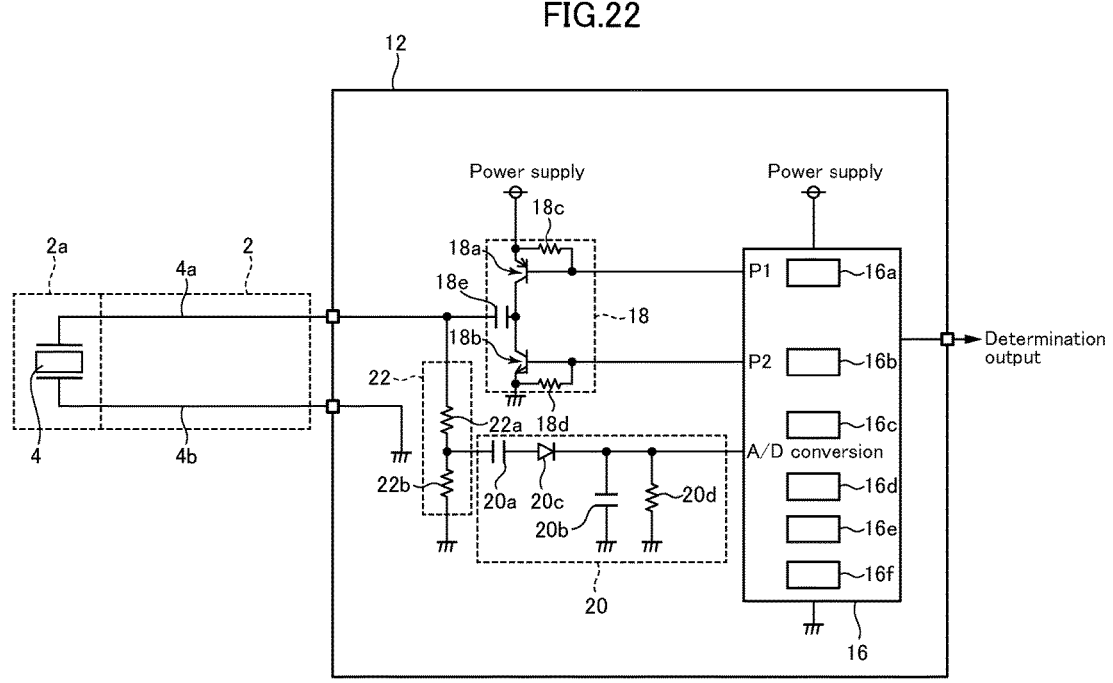
FIG. 22 A circuit diagram showing the simplified constitution of a detection circuit in a third embodiment of the invention.

FIG. 22 is a circuit diagram showing the simplified constitution of a detection circuit in the present embodiment.

As shown in FIG. 22, a microcomputer 16, a drive circuit 18, a signal conversion circuit 20, and a voltage divider circuit 22 are built into the detection circuit 12 of the present embodiment.

This differs from the first embodiment in that the output of the drive circuit 18 (the connecting point of each of the collectors on the PNP transistor 18a and the NPN transistor 18b) is connected to the signal line 4a through a junction capacitor 18e. Thus if there is an offset in the drive circuit 18 voltage output, only the AC voltage component thereof is applied to the signal line 4a.

The microcomputer 16 in the present embodiment differs from the first embodiment in that, in addition to a contact determination circuit 16a, it has built into it a contact determination confirming circuit 16b, an anomaly sensing circuit 16c, a frequency adjustment circuit 16d, a frequency offset sensing circuit 16e, and a determining circuit 16f for determining the outcome of a resonant frequency detection. This frequency offset sensing circuit 16e and determining circuit 16f are also achieved using a program for operating the microcomputer 16.

Next, referring to FIGS. 23 through 32C, we explain the operation of a faucet apparatus 1 according to a third embodiment of the invention.

Figure 23:
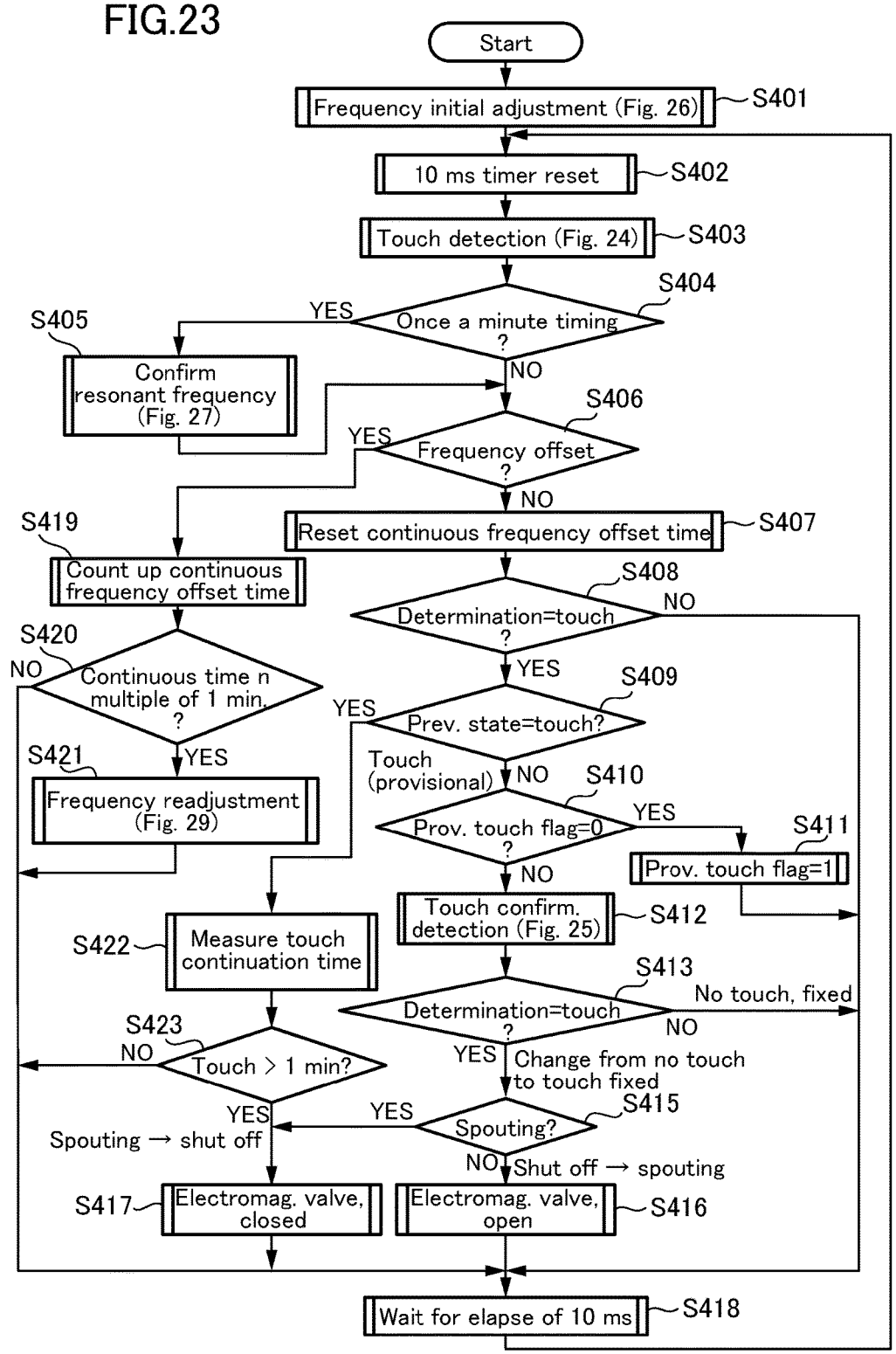
FIG. 23 A main flow diagram showing the operation of a faucet apparatus in a third embodiment of the invention.

FIG. 23 is a main flow diagram showing the action of a faucet apparatus in the present embodiment.

The processing in the FIG. 23 flow chart is executed by the microcomputer 16 built into the detection circuit 12.

Figure 26:
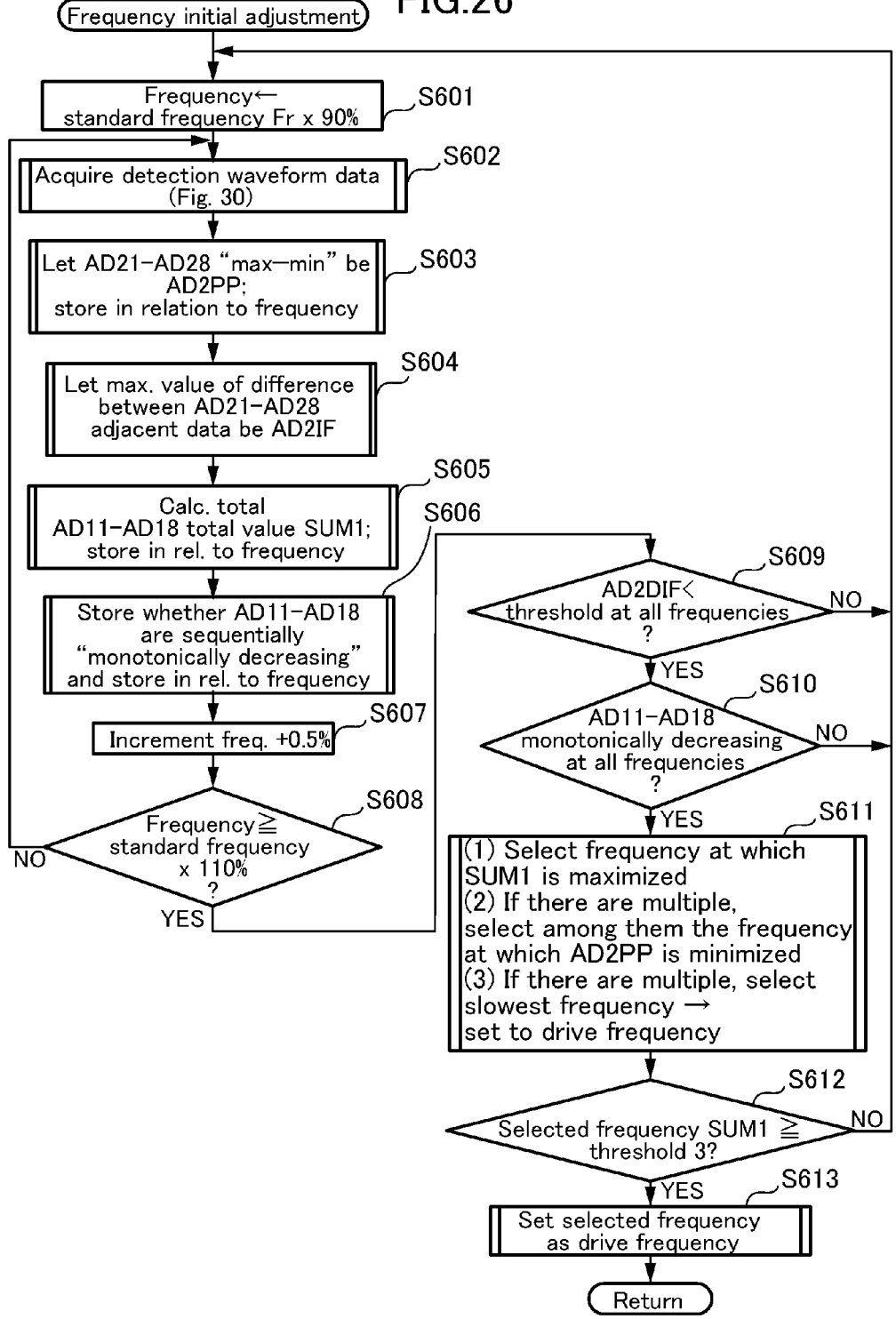
FIG. 26 A frequency initial adjustment flow executed by a frequency adjustment circuit.

First, adjustment of the AC voltage frequency applied to the piezo-electric element 4 is executed in step S401 of FIG. 23. This frequency adjustment is a type of processing by which the frequency of the AC voltage applied to the piezo-electric element 4 is accurately matched to the resonant frequency of the sensing portion 2a and the piezo-electric element 4; in the present embodiment, this processing is executed when the power supply to the detection circuit 12 is turned on. In this step S401, the flow chart shown in FIG. 26 is called as a subroutine. Specific processing in the FIG. 26 flow chart is explained below.

Next, the 10 ms timer is reset in step S402 of FIG. 23. In the present embodiment, application of an AC voltage to the piezo-electric element 4 is executed intermittently each 10 ms, which is the sensing cycle. In step S402, the 10 ms timer controlling this AC voltage application interval is reset, and timer counting is started.

Figure 24:
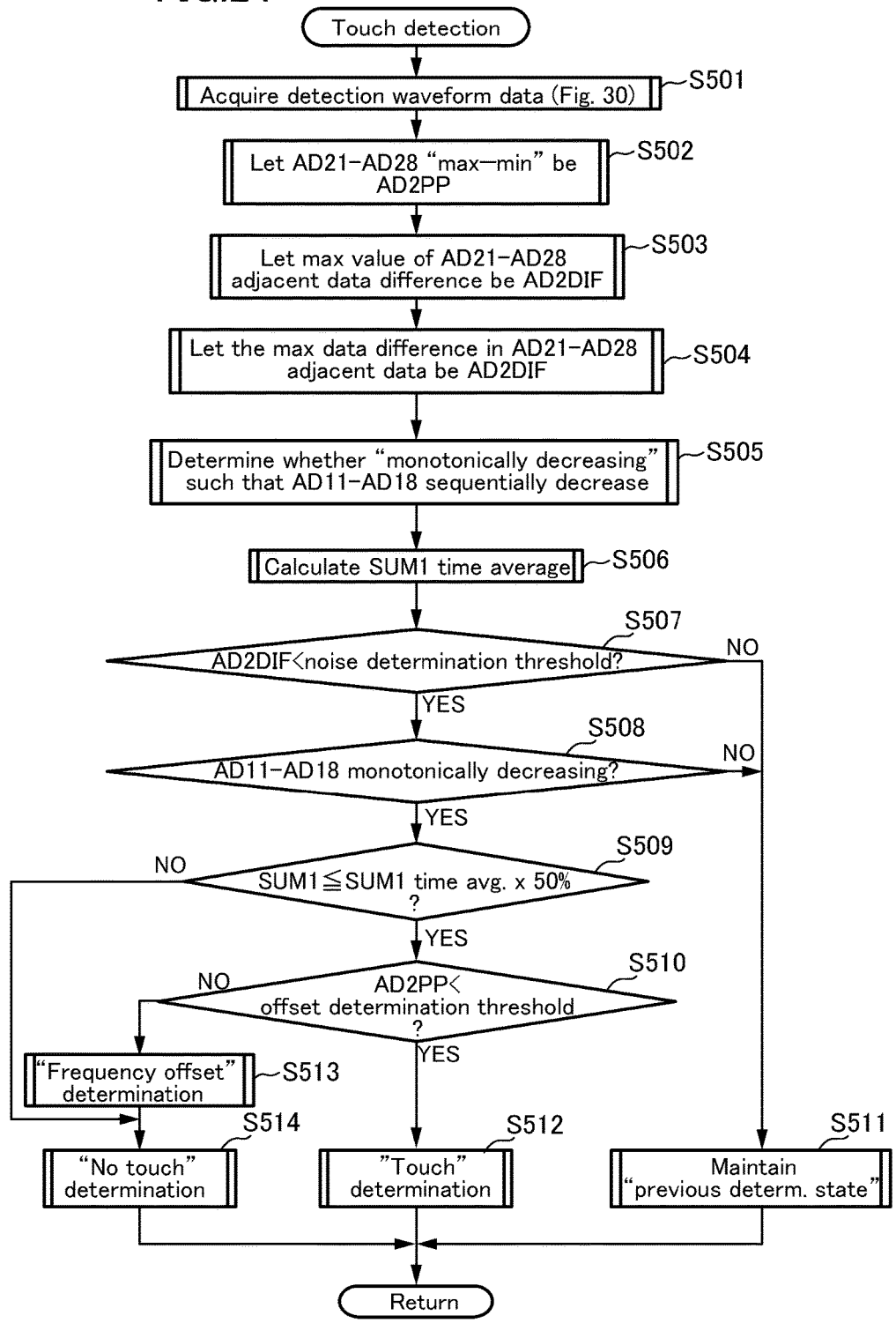
FIG. 24 A touch detection flow called as a subroutine from the main flow.

In addition, in step S403, touching of the sensing portion 2a by a user is detected. I.e., a user is determined to have touched the sensing portion 2a if an AC voltage at a predetermined frequency is applied to the piezo-electric element, based on vibration of the sensing portion 2a after application of the AC voltage has stopped. Specifically, in step S403 the flow chart shown in FIG. 24 is called as a subroutine. Specific processing in the FIG. 24 flow chart is explained below.

Next, in step S404 a determination is made of whether the predetermined timing for confirming a match with the resonant frequency has arrived. I.e., confirmation is made at predetermined time intervals of whether the frequency of the AC voltage applied to the piezo-electric element matches the resonant frequency of the sensing portion 2a. In the present embodiment it is desirable for the frequency of the AC voltage applied to the piezo-electric element and the sensing portion 2a resonant frequency to match. The frequency offset sensing circuit 16e implemented using the microcomputer 16 confirms every 1 minute during operation of the detection circuit 12 that the AC voltage frequency and the resonant frequency sufficiently match. If it is the time to firm the frequency match, the system advances to step S405 and a confirmation is made of whether there is a match; if it is not time to confirm, the system advances to step S406 without confirming.

Figure 27:
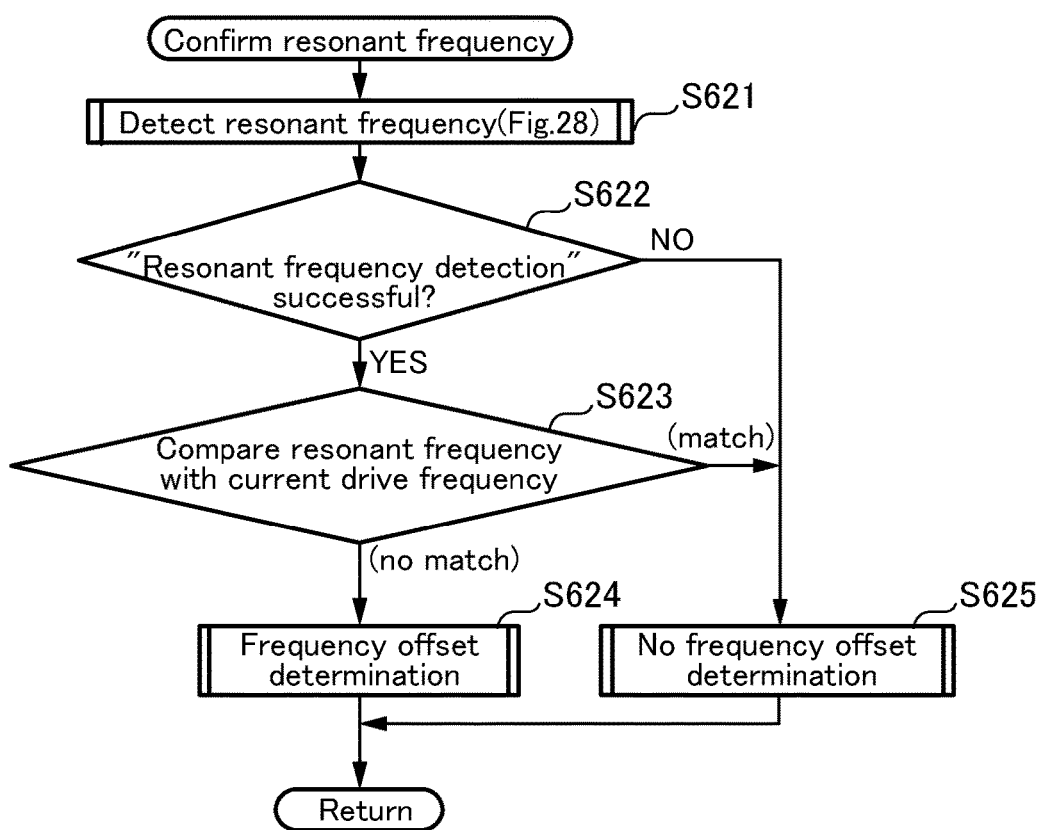
FIG. 27 A resonant frequency confirmation flow called as a subroutine from the main flow.

In step S405, the flow chart shown in FIG. 27 is called as a subroutine. Specific processing in the FIG. 27 flow chart is explained below.

In step S406, a judgment is made of whether the AC voltage frequency and the resonant frequency in the step S405 confirmation were matching; if they did match, the system advances to step S407; if they were offset, it advances to step S419. Note that if a determination is made in step S404 that the timing is not the timing for confirming a match with the resonant frequency, and the system advances from step S404→S407, a judgment in step S406 is formed based on confirmation results in step S405 executed in the recent past. Therefore when an offset between the AC voltage frequency and the resonant frequency is temporarily confirmed in step S405, processing shifts for at least the following 1 minute from step S406 to step S419.

Next, in step S419, counting begins of the time over which a frequency offset continues, following a judgment of "frequency offset occurring" in step S406. In this counting, a judgment is made in step S406 that "no frequency offset is occurring," which is continued until the continuous time count is reset in step S407.

Next, in step S420, a judgment is made of whether the counted frequency offset continuous time is n minutes (where n is an integer). If n minutes, the system advances to step S421; if not n minutes, the system advances to step S418. In step S418, the system stands by until the timer with which the count was started at step S402 reaches 10 ms; when 10 ms elapses, the system returns to step S402, and step S402 and subsequent processing is repeated.

Figure 29:
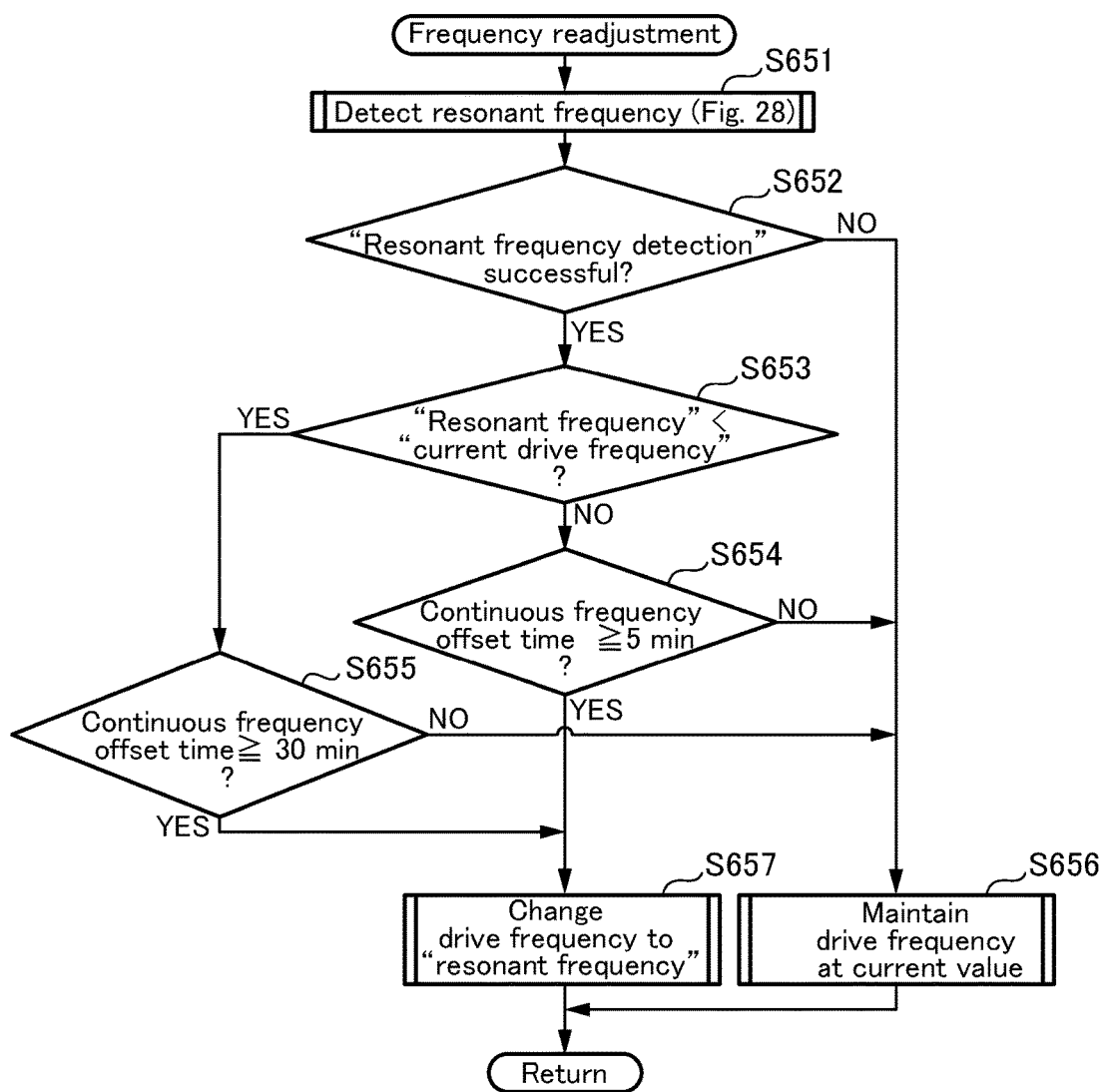
FIG. 29 An AC voltage frequency readjustment flow called as subroutine from the main flow.

On the other hand when the counted frequency offset continuous time is n minutes, the system advances to step S421, and the frequency re-adjustment flow shown in FIG. 29 is executed as a subroutine. Therefore the step S421 frequency readjustment flow is executed every 1 minute while the frequency offset is continuing. Specific processing in the FIG. 29 flow chart is explained below.

In the meantime, when the AC voltage frequency and the resonant frequency match, the system advances to step S407, and in step S407 the frequency offset continuous time which was being counted is reset. As described above, in the processing in step S419 and below, a count is made of the continuous time over which the frequency of the AC voltage applied to the piezo-electric element is offset from the sensing portion 2a resonant frequency. In step S407, because a determination of "no frequency offset" was made in step S406, the frequency offset continuous time that was being counted is reset.

Next, in step S408, a determination is made of whether the detection result in step S403 was a "touch" or a "no touch." If a "touch," the system advances to step S409; if a "no touch," the system advances to step S418. In step S418 following a "no touch" determination, the system stands by until the timer for which the count was started at step S402 reaches 10 ms: when 10 ms elapse, the system returns to step S402, and the S402 and subsequent processing is repeated.

On the other hand in Step S408, if the detection result in step S403 was a "touch," the system advances to step S409, and in step S409 a judgment is made of whether the previous state was a "touch." I.e., in step S409 a judgment is made of whether the determination of a "touch" was fixed when the previous step S409 was executed. Note that in step S413 (described below) executed in the previous loop, the state in which a "touch" is determined is referred to as "confirming a touch determination." In step S409, if the previous state was a "touch (touch determination fixed)," the system advances to step S422; if the previous state was a "touch (touch determination not fixed)," the system advances to step S410.

Next, in step S410, a judgment is made of whether the "provisional touch flag" is 0. Here "provisional touch flag" is a flag which, when there is no "touch determination fixing," but there is a "touch" fixing in the step S403 touch detection executed in the previous instance, is changed to a "1." I.e., when executing step S410, the system advances to step S411 when the "provisional touch flag"=0, and the "provisional touch flag" is changed to 1 in step S411.

In step S411, after the "provisional touch flag" has been changed to 1, the system advances to step S418; when the timer on which the count was started reaches 10 ms, the processing following step S402 is repeated. When step S410 is again executed with the "provisional touch flag"=1, processing shifts to the step S412 touch confirming detection. Thus from a state of "no touch" ("provisional touch flag"=0), if a determination is made in step S408 that the state detected in step S403 (touch detection) has continued for 2 continuous "touch" iterations, processing shifts from step S410 to step S412, and a touch confirming detection is executed.

Figure 25:
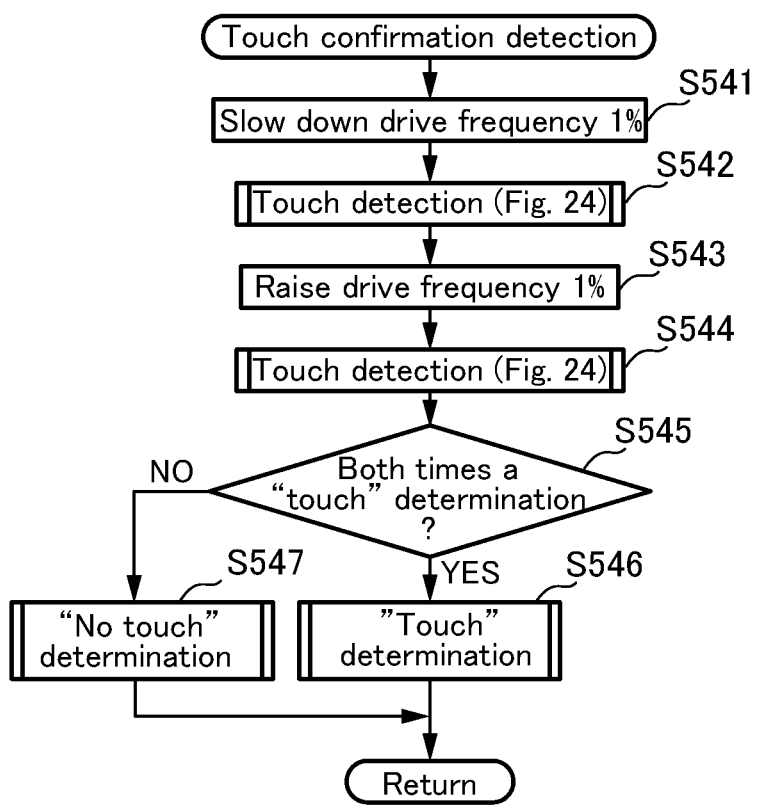
FIG. 25 A touch detection confirmation flow called as a subroutine from the main flow.

In step S412, the flow chart shown in FIG. 25, which is for "touch confirming detection," is executed as a subroutine. This "touch confirming detection" is processing executed to prevent false sensing by "touch detection" in step S403 if the detection result from step S403 changes twice successively from "no touch" to "touch." Specific processing in "touch confirming detection" is discussed below.

In step S413, a determination is made of whether the "touch confirming detection" results were a "touch" or not. If a "no touch," there is a high probability the detection of "touch" in step S403 was a false sensing, therefore the system advances to step S418 without opening or closing the electromagnetic valve, and stands by until 10 ms have elapsed from time t12. On the other hand if the "touch confirming detection" result was "touch," then a "touch determination fixed" is implemented, and the system advances to step S415.

In step S415 a determination is made of whether the faucet apparatus 1 is in a spouting state; if spouting, the system advances to step S416; if it is not spouting, the system advances to step S417. In step S417, the sensing portion 2a has been newly touched in the spouting state, so the hot water electromagnetic valve 8a and the cold water electromagnetic valve 8b are closed, and a switch is made to the shut off state. In step S416, on the other hand, the sensing portion 2a has been newly touched in the shut off state, therefore the hot water electromagnetic valve 8a and the cold water electromagnetic valve 8b are opened, and a switch is made to the spouting state.

In this manner, even if a "touch determination fixed" has been implemented for the sensing portion 2a, the touch detection in step S403 is performed at a fixed interval every 10 ms, which is the predetermined sensing cycle. If a user's "touch" of a sensing portion 2a continues in the "touch determination fixed" state, processing in the FIG. 23 main flow proceeds as follows: step S403→S404→S406→S407→S408→S409→S422 (assumes no "frequency offset" is occurring).

In step S422, the "touch" state continuous time is measured. Specifically, in step S413 the elapsed time following a "touch determination fixed" is measured.

Next, in step S423, a determination is made of whether the continuous touch time measured in step S422 has exceeded 1 minute. If 1 minute is not exceeded, the system advances to step S418, and while the user is touching the sensing portion, the following processing is repeated: step S418→S402→S403→S404→S406→S407→S408→S409→S422→S423→S418 (assumes no "frequency offset" is occurring). On the other hand, if 1 minute has been exceeded, the system advances from step S423 S417, and the hot water electromagnetic valve 8*a* and cold water electromagnetic valve 8*b* are closed regardless of the faucet apparatus 1 state. I.e., a user touching the sensing portion 2*a* for more than 1 minute is an abnormal operation, and there is a high potential that the touch was falsely sensed or the device is broken. The hot water electromagnetic valve 8*a* and cold water electromagnetic valve 8*b* are therefore closed irrespective of the faucet apparatus 1 state, preventing water waste.

In addition, when a "no touch" is detected in the step S403 touch detection, it is recognized that the user has removed his/her hand from the sensing portion 2*a*, and the determination output from the detection circuit 12 is changed to "no touch." However, the faucet apparatus 1 state continues to be in the recently switched state (between the spouting or the shut off state). After a "no touch" detection, until the user again touches the sensing portion 2*a*, the processing in steps S402→S403→S404→S406→S407→S408→S418→S402 are repeated in the FIG. 23 main flow (assumes no "frequency offset" is occurring).

Thereafter if the user again touches the sensing portion 2*a*, and this state is continued, then in the FIG. 23 main flow processing will be carried out in the order of: step S402→S403→S404→S406→S407→S408→S409→S410→S411→S418→S402→S403→S404→S406→S407→S408→S409→S410→S412→S413→S415, so the "touch determination is fixed," and the faucet apparatus 1 state is switched. Thus in the faucet apparatus 1 of the present embodiment, the spouting state and shut off state are alternately switched each time a user touches the sensing portion 2*a* (the operation from the state in which a user's hand is removed from the sensing portion 2*a* until touching).

Figure 30:
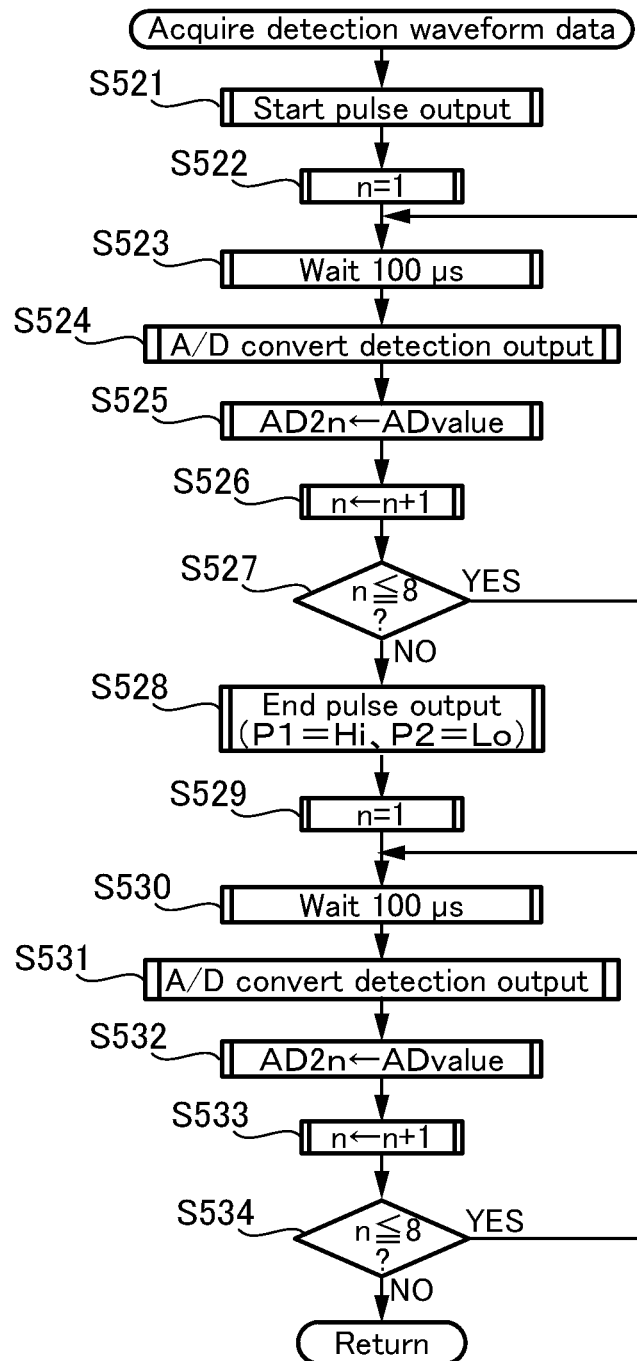
FIG. 30 An envelope detection waveform data acquisition flow called as a subroutine from the touch detection flow.
Figure 31:
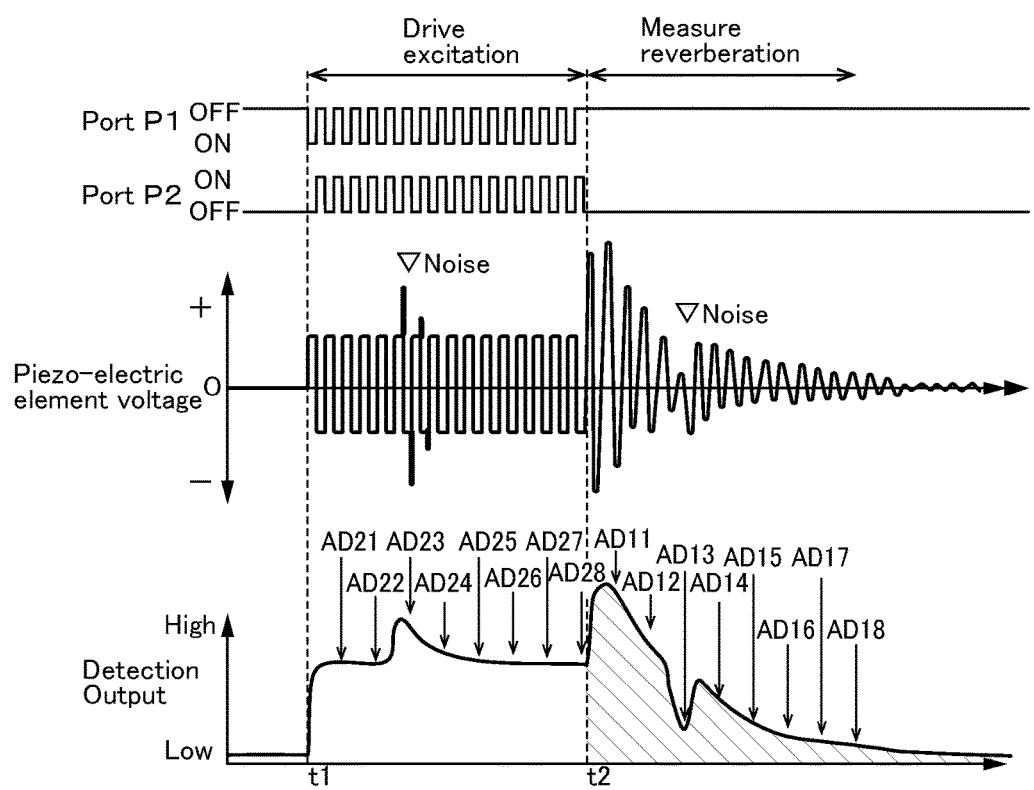
FIG. 31 A diagram showing an example of an acquired envelope detection waveform.

Next, referring to FIGS. 24, 30, and 31, we explain details of the touch detection executed in FIG. 23, step S403.

FIG. 24 is a touch detection flow called as a subroutine from the main flow; FIG. 30 is an envelope detection waveform data acquisition flow called as a subroutine from the touch detection flow. Note that the touch detection flow shown in FIG. 24 is executed by the contact determination circuit 16*a* and anomaly sensing circuit 16*c* constituted by the microcomputer 16 and a program.

Also, FIG. 31 is a diagram showing an example of an acquired envelope detection waveform. Note that FIG. 31 also shows the output voltage waveform from the output ports P1, P2 (FIG. 22) of the microcomputer 16 on the top, the output voltage waveform of the piezo-electric element 4 (the voltage waveform between the signal lines 4*a* and 4*b*) in the middle, and the output voltage waveform from the signal conversion circuit 20 (envelope detection waveform: input waveform to the microcomputer 16 A/D converter) on the bottom. In addition, FIG. 31 shows signal waveforms schematically, and differs from actual waveforms with respect to items such as the number of waves output during application of the AC voltage.

First, the touch detection flow shown in FIG. 24 is called as a subroutine from step S403 in FIG. 23, which is the main flow; the envelope detection waveform data acquisition flow shown in FIG. 30 is called as a subroutine from this touch detection flow step S501.

In the envelope detection waveform data acquisition flow shown in FIG. 30, an AC voltage is first applied to the piezo-electric element 4 over a 0.8 ms period to excite the sensing portion 2*a*, and envelope detection waveform values $AD_{21}$ to $AD_{28}$ are acquired. Detection waveform values $AD_{11}$ to $AD_{18}$ are then acquired as the degree of reverberation during the 0.8 ms interval after stopping the application of an AC voltage.

In FIG. 30, step S521, application of an AC voltage to the piezo-electric element 4 is started (time t1 in FIG. 31). Next, in step S522, the value of variable n is reset to 1. Furthermore, in steps S523-S527, during application of the AC voltage, the output voltage (envelope detection waveform: bottom portion of FIG. 31) of the signal conversion circuit 20 (FIG. 22) is sampled and A/D converted 8 times every 100 μsec. Thus in a 0.8 ms excitation period, 8 output voltage values $AD_{21}$ to $AD_{28}$ are acquired from the signal conversion circuit 20 (lower portion of FIG. 31).

Next, in step S528, the outputs from the microcomputer 16 (FIG. 2) ports P1 and P2 are respectively set to Hi and Lo, which results in turning off both the PNP transistor 18*a* and the NPN transistor 18*b* (end of AC voltage output; time t2 in FIG. 31). In step S529, the value of variable n is reset to 1. Furthermore, in steps S530-S534 immediately after stopping the application of the AC voltage, the signal conversion circuit 20 output voltage is sampled and A/D converted 8 times each 100 μsec. Thus in the 0.8 ms reverberation period after excitation stops, 8 output voltage values $AD_{11}$ to $AD_{18}$ are acquired from the signal conversion circuit 20 (lower portion of FIG. 31) are acquired, one iteration of the processing in the FIG. 30 flow chart is completed, and the system returns to (step S501 of) the touch detection flow shown in FIG. 24.

Next, in step S502 of FIG. 24, a calculation is made of the smallest value subtracted from the largest value amount the output voltage values $AD_{21}$ to $AD_{28}$ acquired in step S501; this value is deemed $AD_{2PP}$. In the example shown in FIG. 31, because $AD_{23}$ is the largest and $AD_{21}$ is the smallest, $AD_{2PP}$ is calculated as $AD_{23}-AD_{21}$.

In addition, in step S503 a calculation is made of differences in adjacent data for the output voltage values $AD_{21}$ to $AD_{28}$ acquired in step S501; the maximum value for this difference is deemed $AD_{2DIF}$. In the example shown in FIG. 31, the difference between $AD_{23}$ and $AD_{22}$ is largest among the adjacent data, so $AD_{2DIF}$ is calculated using $AD_{23}-AD_{22}$.

Next, in step S504, a total SUM1 for the output voltage values $AD_{11}$ to $AD_{18}$ acquired in step S501 is calculated. This SUM1 value is strongly correlated to the area of the diagonally shaded portion in FIG. 31, and indicates the reverberation energy of the sensing portion 2*a* vibration.

Moreover, in step S505 a determination is made of whether the output voltage value $AD_{11}$ to $AD_{18}$ is monotonically decreasing. I.e., if later values are smaller than earlier values in the order of $AD_{11}$ to $AD_{18}$, a monotonic decrease can be assumed. In the example shown in FIG. 31, $AD_{14}$ is growing relative to $AD_{13}$, so it is judged that $AD_{11}$ to $AD_{18}$ "are not monotonically decreasing."

In addition, in step S0 an average value $SUM1_{AV}$ is calculated from each of the SUM1 values respectively calculated when the FIG. 24 flow chart is executed for the most recent 3 minutes, I.e., $SUM1_{AV}$ is a moving average value for the last 3 minutes of SUM1. Here the time during which a user is touching the sensing portion 2*a* in a single operation is approximately 1 sec at the longest, therefore the majority of the SUM1 values calculated during the past 3 minutes may be assumed to have been acquired in the "no touch" state. Hence the $SUM1_{AV}$, which is the average of SUM1, indicates the size of the average reverberation energy in the "no touch" state.

Next, in step S507, the $AD_{2DIF}$ calculated in step S503 is compared with the noise determination threshold; if the $AD_{2DIF}$ is smaller than the noise threshold, the system advances to step S508; if the $AD_{2DIF}$ is larger than the noise threshold, the system advances to step S511. I.e., if the detection circuit 12 picks up electrical noise, or a stiff object like a knife contacts the sensing portion 2a, a disturbance in the envelope detection waveform pulse shape occurs. FIG. 31 shows an example of noise picked up by the detection circuit 12; a disturbance of the envelope detection waveform is occurring in the part shown as "noise" in the middle figure. When such a disturbance occurs, the envelope detection waveform changes suddenly, and the time derivative value thereof increases, allowing a determination of whether a disturbance in the envelope detection waveform has occurred by comparing the maximum value $AD_{2DIF}$ of the difference with the adjacent detection value. Note that by making a determination based on the maximum value $AD_{2DIF}$ of the difference vs. the adjacent detection value, a clear differentiation can be made between a waveform disturbance caused by noise or the like and a waveform disturbance occurring when the frequency of the applied AC voltage and the resonant frequency are offset (FIGS. 9, 11 etc.).

Next, in step S511 of FIG. 24, because detected data picks up noise and the like, no determination pertaining to touch detection from the present instance of the envelope detection waveform is made, and the "touch" or "no touch" determination from the previous execution is maintained as is, completing one iteration of the flow chart shown in FIG. 24.

In step S507, on the other hand, when the $AD_{2DIF}$ is smaller than the noise determination threshold value, the system advances to step S508. In step S508, a judgment is made of whether the value of $AD_{11}$ to $AD_{18}$, which expresses reverberation, is monotonically decreasing; if monotonically decreasing, the system advances to step S509; if not monotonically decreasing, the system advances to step S511. As described above, the envelope detection waveform is disturbed when the detection circuit 12 picks up noise or the like, and the value of $AD_{11}$ to $AD_{18}$ stops monotonically decreasing. In this case, because the detected data is picking up noise or the like, the system advances to step S511 and no determination pertaining to touch detection is made from the envelope detection waveform on this occasion.

Meanwhile in step S509 the SUM1 and the $SUM1_{AV}$ values are compared. If SUM1 is ½ or less of $SUM1_{AV}$, the system advances to step S510; if SUM1 is greater than ½ of $SUM1_{AV}$, the system advances to step S514. I.e., when SUM1 is greater than ½ $SUM1_{AV}$, the reverberation energy SUM1 detected in the current iteration does not differ greatly from the average reverberation energy $SUM1_{AV}$ in the "no touch" case, therefore in step S514 a determination of "no touch" is made, and one iteration of the FIG. 24 flow chart processing is completed. This "no touch" determination is used to make a judgment in the main flow (FIG. 23) step S408.

Meanwhile, when SUM1 has a value ½ or less of $SUM1_{AV}$, the system advances to step S510. I.e., when SUM1 is ½ or less of $SUM1'_{AV}$, the reverberation energy SUM1, detected in the current iteration, has dropped much more than the average reverberation energy $SUM1_{AV}$ in the "no touch" case, so there is a high potential that the sensing portion 2a has been touched. I.e., in the present embodiment, a determination is made of whether a "touch" of the sensing portion 2a has been made based on the sensing portion 2a vibration energy after application of an AC voltage is stopped, and when the vibration energy is at or below a predetermined threshold, it is determined that a "touch" has been made.

In step S510, the difference between the maximum and minimum values for the output voltage values $AD_{21}$ to $AD_{28}$ calculated in step S502 is compared with a predetermined offset determination threshold. When the difference $AD_{2PP}$ between the maximum and minimum values is less than the determination threshold, the system advances to step S512, and determines a "touch" in step S512, completing the FIG. 24 flow chart 1. This "touch" determination is used to make a judgment in the main flow (FIG. 23) step S408.

Meanwhile in step S510, if the difference $AD_{2PP}$ between maximum and minimum values is at predetermined offset determination threshold value or above, the system advances to step S513. Thus when reverberation energy is small and the envelope detection output waveform during excitation is not a fixed value, it is believed that, as explained with reference to FIG. 9, etc., the frequency of the AC voltage applied to the piezo-electric element 4 and the sensing portion 2a resonant frequency are offset. Hence in step S513 a "frequency offset" is determined, and in step S514 a "no touch" is determined, ending one iteration of the FIG. 24 flow chart. I.e., the anomaly sensing circuit 16c built into the microcomputer 16 senses an anomaly when the envelope detection waveform output voltage value fluctuates by more than a predetermined offset determination threshold value during application of an AC voltage to the voltage element 4, and does not determine a "touch."

Thus if there is an offset between the resonant frequency and the frequency of the applied AC voltage, a phenomenon arises whereby the pulse waveform is disturbed during application of the AC voltage, and the amplitude changes. To prevent detection of a "touch" resulting in false sensing in such frequency offset states, a "no touch" determination is made when the difference between the maximum value and the minimum value during application of the AC voltage is greater than a predetermined offset determination threshold value in step S510 of FIG. 24.

Next, referring to FIGS. 25 and 32A through 32C, we explain the touch confirming detection flow, which confirms the "touch" determination and results in a "touch determination fixing."

Figure 32A:
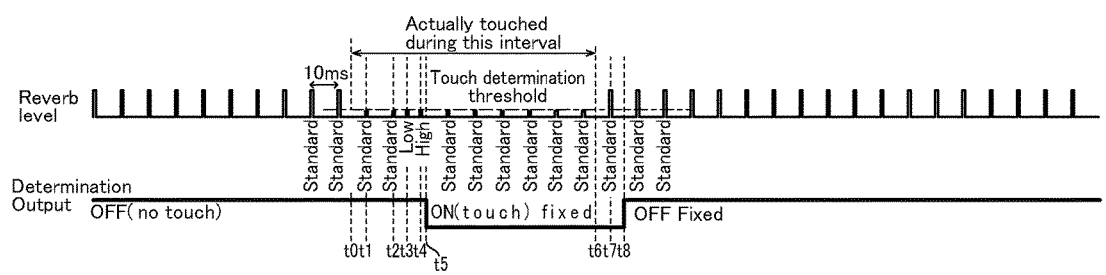
FIG. 32A A time chart explaining a "touch" determination and the processing to fix the "touch" determination.
Figure 32B:
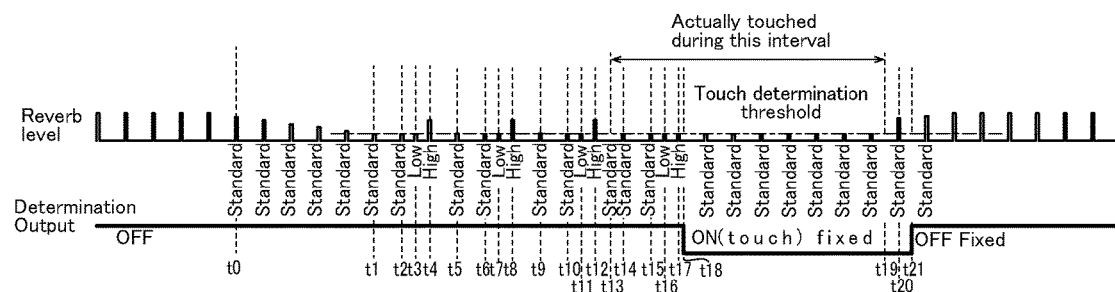
FIG. 32B A time chart explaining a "touch" determination and the processing to fix the "touch" determination.
Figure 32C:
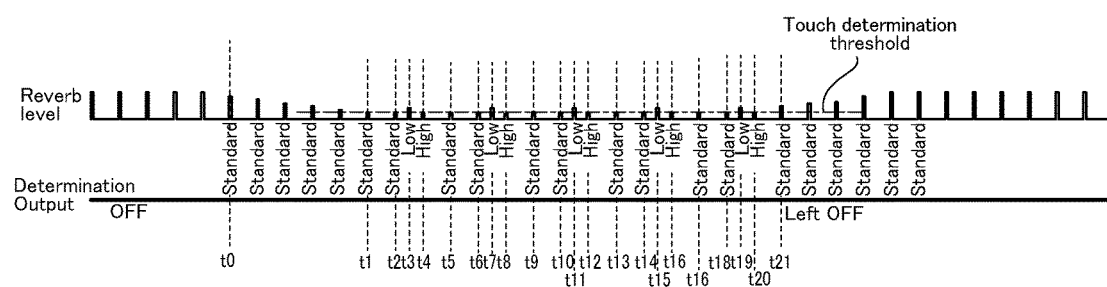
FIG. 32C A time chart explaining a "touch" determination and the processing to fix the "touch" determination.

FIG. 25 is a touch confirming detection flow; this touch confirming detection flow is called as a subroutine at step S412 in the main flow shown in FIG. 23. FIGS. 32A-32C are a time chart explaining a "touch" determination and the processing to fix the "touch" determination.

First, in step S541 of FIG. 25, the frequency of the AC voltage applied to the piezo-electric element 4 is set at a confirmation frequency 1% lower than the frequency applied in a normal touch detection. In this embodiment, because the frequency of the applied AC voltage in a touch detection is approximately 40 kHz, the frequency of the AC voltage is set to 39.6 kHz in step S541. Thus as a contact determination confirmation action the contact determination confirming circuit 16b applies an AC voltage to the piezo-electric element 4 at a frequency different from the normal AC voltage frequency, after a user's touch is first determined using the contact determination circuit 16a (FIG. 23, step S410).

Next, in step S542, the above-described touch detection flow (FIG. 24) is called as a subroutine. The touch detection flow executed here is the same as the above-described processing except that the frequency of the AC voltage applied to the piezo-electric element is changed to approximately 39.6 kHz.

In addition, in step S543 the frequency of the AC voltage applied to the piezo-electric element 4 is set to a confirmation frequency 1% higher than the normal touch detection frequency. In step S543, therefore, the AC voltage frequency is set to approximately 40.4 kHz.

Next, in step S544, the above-described touch detection flow (FIG. 24) is again called as a subroutine. The touch detection flow executed here is the same as step S542 except that the frequency of the AC voltage applied to the piezo-electric element 4 is changed to approximately 40.4 kHz.

Next, in step S545, the touch detection results of step S542 and S544 are determined. I.e., if the returned values from the touch detection flow executed as a subroutine in steps S542 and S544 are both a "touch" determination (FIG. 24, steps S512), the system advances to step S546; if one is a "no touch" determination (FIG. 24, step S514), the system advances to step S547.

In step S546, a determination is made that the user really is touching the sensing portion 2a, and the "touch" determination is fixed (there is a transition from step S413→S415 in the FIG. 23 main flow). Thus when a user "touch" is determined by the contact determination circuit 16a through the application of an AC voltage at a confirming frequency, as well, the contact determination confirming circuit 16b fixes the determination that the sensing portion 2a is "touched." Meanwhile, in step S547 (in the FIG. 23 main flow step S403), while a "touch" determination has been temporarily made, in fact it is determined that no touch has occurred, and the "no touch" determination is fixed (transition from step S413→S418 in the FIG. 23 main flow).

Next, referring to FIGS. 32A through 32C, we explain the principle of touch confirming detection.

In FIG. 32A through 32O, the horizontal axis shows time; the top portion shows reverberation vibration energy levels produced by the application of each AC voltage; on the bottom portion is a time chart showing whether there is a "touch determination fixing."

FIG. 32A shows an example when there is no resonant frequency offset in the sensing portion 2a. First, before time t0 in FIG. 32, there is no user "touch" of the sensing portion 2a, and a major reverberation vibration occurs after application of an AC voltage to the piezo-electric element 4, due to that application. Hence before time t0, reverberation vibration at a level higher than the threshold shown by the single dot and dash line in the upper portion of FIG. 32 is detected each 10 msec.

Next, at time t0, when a user "touches" the sensing portion 2a, the reverberation vibration energy in the touch detection executed immediately thereafter at time t1 (FIG. 23, step S403) drops to below the threshold value. As described above, once a "touch" is sensed, the "provisional touch flag" is changed to a 1 (FIG. 23, step S411), and a touch detection is again executed at time t2 (FIG. 23, step S403). In the touch detection executed at this time t2, as well, if the reverberation vibration energy is low, a touch confirming detection (FIG. 23, step S412) is executed.

In the touch confirming detection (the FIG. 25 subroutine called by FIG. 23, step S412), an AC voltage at a frequency lower than the normal touch detection is first applied at time t3 (FIG. 25, step S541). In a state in which a user "touches" the sensing portion 2a, reducing the AC voltage frequency results in a lowering of the reverberation vibration energy even if an offset is occurring relative to the sensing portion 2a frequency. Next, at time t4, an AC voltage at a frequency higher than the normal touch detection is applied to the piezo-electric element 4 (FIG. 25, step S54). If a user is "touching" the sensing portion 2a, similarly, the reverberation vibration energy will decrease even if the AC voltage frequency is raised. Thus a "touch" is determined (FIG. 25, step S545→S546) in a touch confirming detection flow (FIG. 25). Hence if a "touch" is determined in the touch confirming detection flow, a "touch" determination is fixed in the main flow (FIG. 23) (FIG. 23, step S413→S415, FIG. 32A, time t5).

After a "touch" determination has been fixed at time t5 in FIG. 32A, a touch detection (FIG. 23, step S403) is executed every 10 ms until changing to a "no touch" (until the user removes his/her hand from the sensing portion 2a) at time t6. During this period the detected reverberation vibration energy is at a lower value than the threshold value. Subsequent to time t6, when a touch detection is executed at time t7, the detected reverberation vibration energy becomes a higher value than the threshold value, and the fact that a "no touch" state has been reached is fixed (FIG. 32A, time t8; FIG. 23, step S408 S418).

Next, referring to FIG. 32B, we explain the effect of a touch confirming detection when the sensing portion 2a resonant frequency has risen due to temperature changes.

In FIG. 32B, no "touching" by a user occurs until time t13, but from time t0 forward, due to temperature changes in the sensing portion 2a, there is a trend toward lower reverberation vibration energy detected by touch detection (FIG. 23, step S403). I.e., the rise of the sensing portion 2a resonant frequency caused by a drop in the temperature of the sensing portion 2a results in an offset relative to the frequency of the AC voltage applied in touch detection. As a result, without the sensing portion 2a being sufficiently excited, the detected reverberation vibration energy drops.

At time t1 in FIG. 32B, the reverberation vibration energy drops due to the rise in the sensing portion 2a resonant frequency, and energy goes to a value below the threshold value even though there is no "touch." An incorrect "touch" determination is thus made (FIG. 23, step S408→S409); furthermore if a "touch" determination is made at time t2 (FIG. 23, step S408→S409→S410), a touch confirming detection is executed (FIG. 23, step S410→S412, FIG. 25).

In touch confirming detection, an AC voltage at a frequency lower than the normal touch detection is first applied to the piezoelectric element 4 (FIG. 25, step S541; FIG. 32B, time t3). At time t3, the user is not "touching" the sensing portion 2a, but the sensing portion 2a resonant frequency is rising, resulting in a large difference between the frequency of the applied AC voltage and the resonant frequency, such that the detected reverberation vibration energy drops. Next, at time t4, an AC voltage at a frequency higher than the normal touch detection is applied to the piezo-electric element 4 (FIG. 25, step S543). Here, because the sensing portion 2a resonant frequency is rising, the frequency of the applied AC voltage and the resonant frequency have similar values, and the detected reverberation vibration energy is higher than the threshold value. A "no touch" is thus determined in the touch confirming detection (FIG. 25, step S545→S547), and false sensing caused by a rising resonant frequency is avoided.

After time t4 in FIG. 32 up until time t13, no "touch" is performed by a user, but because the sensing portion 2a resonant frequency is rising in the touch detection, the reverberation vibration energy drops below the threshold value (reverberation vibration energy at times t5 to t7 and t9 to t11). However, because the AC voltage applied within the touch confirming detection is at a frequency higher than the normal AC voltage frequency, the reverberation vibration energy exceeds the threshold value (reverberation vibration energy at times t8, t12), and a "no touch" determination is made. False sensing due to resonant frequency rise can thus be avoided.

Next, after a user "touches" in FIG. 32B, time t13, reverberation vibration energy from touch detections at times t1 and t15 diminishes. In addition, reverberation vibration energy from touch confirming detections at times t16 and t17 also diminishes. I.e., when a user "touches" the sensing portion 2a, reverberation vibration energy decreases to below the threshold value even when the frequency of the applied AC voltage and the resonant frequency are close (time t17), and at time t18 a "fix touch determination" occurs. Thus in touch confirming detection, by applying AC voltages to the piezo-electric element 4 at frequencies higher and lower than normal touch detection, "touches" can be reliably detected, and false sensings avoided.

In FIG. 32B, subsequent to a "touch determination fixing" at time t18 up until changing to a "no touch" at time t19 (until the user removes his/her hand from the sensing portion 2a), a touch detection is executed every 10 ms. During this period the detected reverberation vibration energy is at a lower value than the threshold value. In the example shown in FIG. 32B, when a touch detection is performed at time t20 after time t19, the sensing portion 2a temperature rises and the resonant frequency approaches the frequency of the AC voltage in a normal touch detection. The reverberation vibration energy detected by the touch detection at time t20 is therefore at a higher value than the threshold value, and the change to a "no touch" state is fixed (FIG. 323, time t12 forward).

In the example shown in FIG. 32B we explained the case in which the sensing portion 2a resonant frequency rises due to a temperature drop, but it is also the case that when the sensing portion 2a resonant frequency drops due to a temperature rise or water droplet adhesion or the like, touch confirming detection allows "touches" to be reliably detected while avoiding false sensings. Note that in cases where the resonant frequency is only expected to decrease due to factors such as the constitution and usage environment of the sensing portion 2a, the invention can be constituted so that touch confirming detection is performed only at frequencies lower than that of the AC voltage used in normal touch detection. Conversely, in cases where the resonant frequency is only expected to increase, the invention can be constituted so that touch confirming detection is performed only at frequencies higher than that of the AC voltage used in normal touch detection.

Next, referring to FIG. 32C, we explain the effect of a touch confirming detection when the sensing portion 2a resonant frequency has dropped due to a temperature rise.

In FIG. 32O, no "touching" by a user occurs; but from time t0 forward, due to sensing portion 2a temperature changes, there is a trend toward lower energy of the reverberation vibration detected by touch detection. I.e., the drop in the sensing portion 2a resonant frequency caused by a rise in the temperature of the sensing portion 2a results in an offset relative to the frequency of the AC voltage applied in touch detection. Hence the detected reverberation vibration energy drops off, with insufficient excitation of the sensing portion 2a at the AC voltage frequency used in normal touch detection.

Therefore at times t1 and t2 in FIG. 32O, the reverberation vibration energy in the touch detection can drop below a threshold value so that a "touch" determination is made even though no user has "touched." When a "touch" is determined, a touch confirming detection (FIG. 23, step S412) is executed. In a touch confirming detection, an AC voltage is applied at a lower frequency than in normal touch detection (FIG. 25; step S541; FIG. 32C, time t3), then an AC voltage is applied at a higher frequency than in normal touch detection (FIG. 25, step S543; FIG. 32C, time t4).

Here, because the sensing portion 2a resonant frequency drops due to a temperature rise, the AC voltage is applied at time t3 at a frequency lower than in normal touch detection, and approaches the resonant frequency of the sensing portion 2a. In the application of the AC voltage at time t3, the reverberation vibration energy exceeds a threshold value. Meanwhile in the application of an AC voltage at a higher frequency than in normal touch detection, performed at time t4, reverberation vibration energy drops due to drifting from the resonant frequency of the sensing portion 2a. In touch confirming detection, reverberation vibration energy exceeded a threshold value during application of an AC voltage at time t3, therefore a "no touch" determination is made (FIG. 25, step S545→S547), and false sensings are excluded.

Similarly, in the state in which the sensing portion 2a temperature is rising and the resonant frequency is falling, the reverberation vibration energy falls below a threshold value in normal detections (FIG. 32C, times t5, t6, t9, t10, t13, t14, t17, t18). When applying a low frequency AC voltage in touch confirming detection (FIG. 32C, time t7, t11, t15, t19), reverberation vibration energy exceeds a threshold value and false sensings are avoided. Also, when the sensing portion 2a temperature drops and the resonant frequency returns to a normal value at time t21 in FIG. 32C, the reverberation vibration energy in the normal touch detection exceeds a threshold value, after which a "no touch" determination is made, without executing a touch confirming detection.

Next, referring to FIG. 26, we explain initial frequency adjustment.

FIG. 26 is a frequency initial adjustment flow executed by a frequency adjustment circuit 16d. The flow chart shown in FIG. 26 is what is called as a subroutine in step S401 of the main flow shown in FIG. 23. As a first adjustment mode, the frequency adjustment circuit 16d searches for the sensing portion 2a resonant frequency within a predetermined frequency range. I.e., the frequency adjustment circuit 16d applies an AC voltage to the piezo-electric element 4 at multiple frequencies within a predetermined frequency range, obtains respective output signals from the piezo-electric element 4 when these AC voltages are applied, and executes frequency adjustment by analyzing these output signal envelope detection waveforms. In the first adjustment mode, the frequency of the AC voltage applied to the piezo-electric element 4 in touch detection is determined so as to match the actual resonant frequency of the sensing portion 2a.

In FIG. 26, step S601, the frequency of the AC voltage applied to the piezo-electric element 4 is set at 90% of the standard frequency Fr. Note that standard frequency Fr is a design value for the resonant frequency when the sensing portion 2a and the piezo-electric element 4 vibrate as an integral unit. In the present embodiment the standard frequency Fr=40 kHz, therefore the AC voltage frequency is first set at 36 kHz. In the FIG. 26 flow chart, AC voltages are applied to the piezo-electric element 4 at multiple frequencies between 90% and 110% of the standard frequency Fr, and the frequency of the AC voltage to be applied to the piezo-electric element 4 is determined based on the resulting reverberation vibration energy. I.e., in the first adjustment mode, the resonant frequency is searched within a first frequency range which includes the standard frequency Fr.

Next, in step S602, the flow chart shown in FIG. 30 is executed as a subroutine. As described above, in the flow chart shown in FIG. 30 an AC voltage with a frequency set in step S601 is applied, and output voltage values $AD_{11}$ to $AD_{18}$ and $AD_{21}$ to $AD_{28}$ (FIG. 31) are acquired for the envelope detection waveform acquired at that time.

Next, a value is calculated by subtracting the minimum value from the maximum value among the output voltage values $AD_{21}$ to $AD_{28}$ acquired in Step S602; this value is deemed $D_{2PP}$ This value is stored together with the applied AC voltage frequency.

Furthermore, in step S604 the difference is calculated for adjacent data for the output voltage values $AD_{21}$ to $AD_{28}$ acquired in step S602; the maximum value for this difference is deemed $AD_{2DIF}$. This value is stored together with the applied AC voltage frequency.

Next, in step S605, a total SUM1 is calculated for the output voltage values $AD_{11}$ to $AD_{18}$ acquired in step S602. This value is stored together with the frequency of the applied AC voltage.

Also, in step S606 a determination is made of whether the output voltage value $AD_{11}$ to $AD_{18}$ is monotonically decreasing. The result of whether it is monotonically decreasing is stored together with the frequency of the applied AC voltage.

Next, at step S607, the AC voltage frequency set in step S601 is increased by 0.5%. I.e., the AC voltage frequency in step S607 is changed to 36.2 kHz; and the processing following step S602 is repeated by step S608. After this, the frequency of the AC voltage is increased in 0.2 kHz increments, and the processing in step S602 to step S607 is repeated until reaching 44 kHz.

Next, in step S609, the $AD_{2DIFs}$ calculated for each frequency in step S604 is compared with a predetermined noise determination threshold; if all the $AD_{2DIFs}$ are smaller than the noise determination threshold, the system advances to step S610; if even one of the $AD_{2DIFs}$ is at or above the noise determination threshold, the system returns to step S601. I.e., when the $AD_{2DIF}$ value is equal to or above a noise determination threshold value, there is a high probability that noise is mixed into the detection data, so the system advances to step S601 and re-measures.

On the other hand, in step S609, when the $AD_{2DIF}$ is smaller than the noise determination threshold value, the system advances to step S610. In step S610, a judgment is made of whether the value of $AD_{11}$ to $AD_{18}$, which expresses reverberation, is monotonically decreasing; if monotonically decreasing at all frequencies, the system advances to step S611; if not monotonically decreasing; the system advances to step S601. As described above, the envelope detection waveform is disturbed when the detection circuit 12 picks up noise or the like, and the value of $AD_{11}$ to $AD_{18}$ stops monotonically decreasing. In this case, because the detected data picks up noise, etc., the system returns to step S601 and re-measures.

Next, in step S611, the frequency at which reverberation vibration is greatest (total value SUM1 of output voltage values $AD_{11}$ to $AD_{18}$) is selected as the resonant frequency. Then, if there are multiple frequencies at which reverberation vibration is maximized, the frequency at which the difference $AD_{2PP}$ between the maximum and minimum values is smallest is selected as the resonant frequency. If there are multiple frequencies at which both the reverberation vibration and the difference $AD_{2PP}$ between the maximum and minimum values are equal, the lowest frequency among them is selected as the resonant frequency.

In addition, in step S611 the total value SUM1 of the output voltage values $AD_{11}$ to $AD_{18}$ at the frequencies where the reverberation vibration is greatest is compared with a predetermined threshold value. If the total value SUM1 is smaller than the predetermined threshold value, the system returns to step S601 and re-measures. I.e., if the reverberation vibration at the resonant frequency is far smaller than the design-anticipated reverberation vibration, there may be errors in the measurement, so the measurement is re-performed. The frequency of the AC voltage applied to the piezo-electric element 4 serves as the foundation for touch detection, so the frequency adjustment circuit 16d repeats the resonant frequency search until frequency adjustment is successful. Note that after the start of the FIG. 26 processing, the present invention can be constituted so that processing is stopped and an alarm is issued if processing does not end despite the elapse of a predetermined time.

On the other hand if the total value SUM1 is at or above a predetermined threshold value, the system advances to step S613. In step S613, the frequency selected in step S611 is measured as the frequency of the AC voltage applied to the piezo-electric element 4 (the drive frequency), and the first processing of the flow chart shown in FIG. 26 ends. Frequencies determined by the flow chart shown in this FIG. 26 are used in touch detection as initial values for the AC voltage frequencies applied to the piezo-electric element 4 (FIG. 23, step S403).

Figure 28:
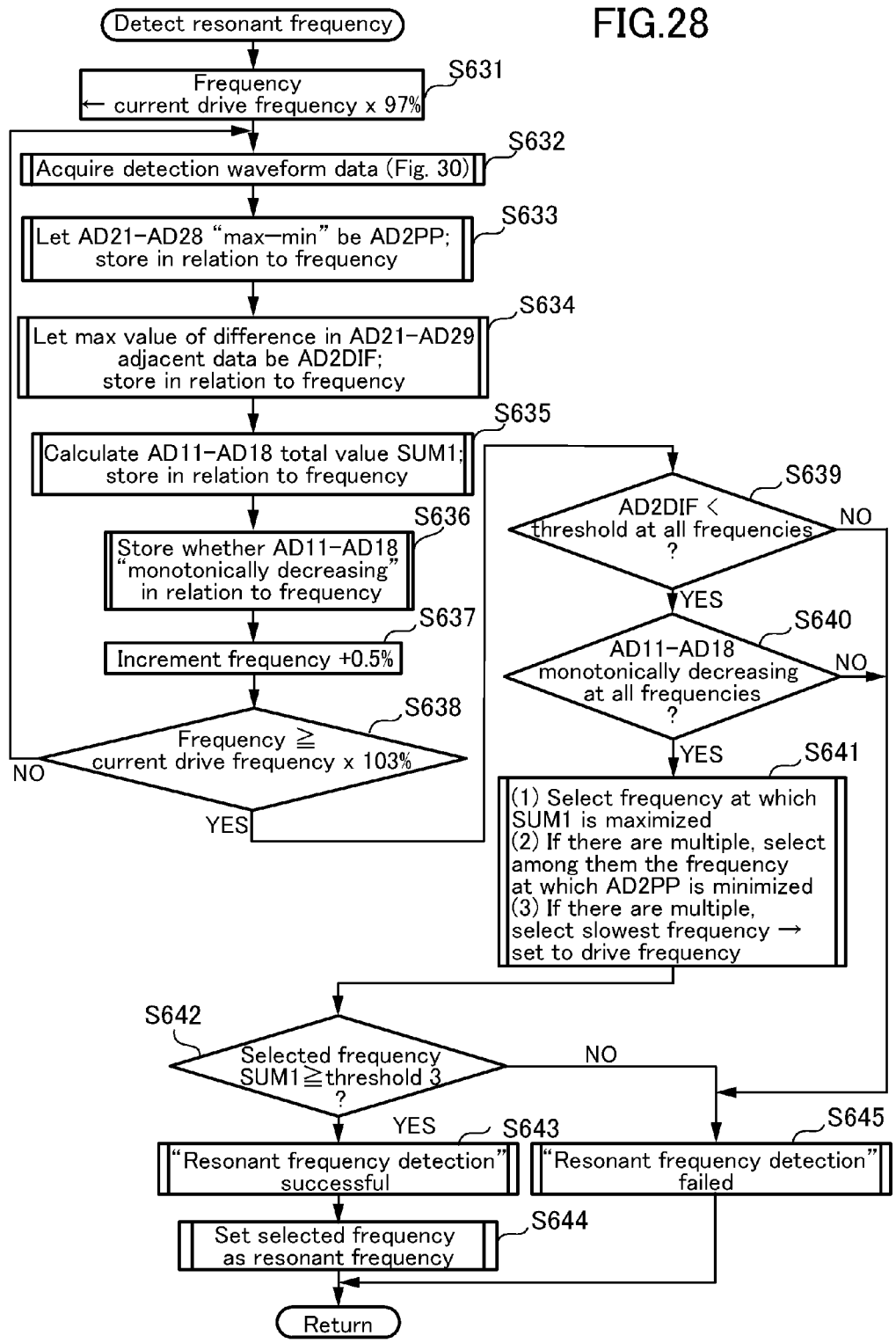
FIG. 28 A resonant frequency detection flow called as a subroutine from the resonant frequency confirmation flow.

Next, referring to FIGS. 27 and 28, we explain resonant frequency confirmation processing.

FIG. 27 is a resonant frequency confirmation flow called as a subroutine from the main flow shown in FIG. 23; FIG. 28 is resonant frequency detection flow called as a subroutine from the flow chart shown in FIG. 27.

As described above, in the touch detection device of the present embodiment, it is desirable for the frequency of the AC voltage applied to the piezo-electric element 4 to be well matched to the sensing portion 2a resonant frequency. This AC voltage frequency, as discussed above, is accurately adjusted by the frequency initial adjustment flow shown in FIG. 26 when execution of the main flow starts (FIG. 23, step S401). However the frequency of the sensing portion 2a may change due to temperature changes in the sensing portion 2a, adhesion of water droplets to the sensing portion 2a, aging, etc. Therefore in the present embodiment the sensing portion 2a resonant frequency is confirmed at a predetermined time interval even during execution of the main flow. Specifically, during main flow execution processing transitions from step S404 to step S405 in FIG. 23 with each elapsed minute and, starting with step S405, the resonant frequency confirmation flow shown in FIG. 27 is executed as a subroutine.

First, in FIG. 27, step S621, the resonant frequency detection flow shown in FIG. 28 is executed as a subroutine. As described below, in the resonant frequency flow shown in FIG. 28 the resonant frequency of the sensing portion 2a is detected by the same type of processing as in the above-described frequency initial adjustment flow (FIG. 26).

Next, in step S622 of FIG. 7, in the resonant frequency detection flow shown in FIG. 28 a judgment is made of whether the resonant frequency detection was successful. If the resonant frequency detection was successful, the system advances to step S623; if the resonant frequency detection failed, the system advances to step S625.

Next, in step S623, a judgment is made of whether the resonant frequency detected in step S621 and the current frequency of the AC voltage applied to the piezo-electric element 4 match. In the present embodiment, if the difference between the resonant frequency and the current frequency of the AC voltage is less than 0.5%, a determination is made that there is no offset between the resonant frequency and the AC voltage frequency, and the system advances to step S625.

If the difference between the resonant frequency and the current frequency of the AC voltage is equal to greater than 0.5%, a determination is made that there is an offset between the resonant frequency and the AC voltage frequency, and the system advances to step S624. These determination results are used to judge whether there is a frequency offset in the main flow step S406 shown in FIG. 23.

On the other hand in step S622, when there is a determination that frequency detection has failed, the system advances to step S625 and determines that "there is no offset between the resonant frequency and the AC voltage frequency." In this case, the frequency was actually detected, but because the detection was mid-stream during main flow operation, if the detection were hypothetically repeated until successfully detecting a resonant frequency, no touch detection could be processed during that period, and touch detection device functionality would be lost. Therefore in the present embodiment even if resonant frequency has failed, it will be processed as "no frequency offset," and the main flow processing will continue. In the present embodiment the resonant frequency detection flow shown in FIG. 28 is executed at 1 minute intervals, therefore a single failure in resonant frequency detection would not adversely the touch detection device functionality.

Next, referring to FIG. 28, we explain the resonant frequency detection flow.

As shown in FIG. 28, the resonant frequency detection flow performs essentially the same processing as the above-described frequency initial adjustment flow shown in FIG. 26.

First, step S631 to step S638 of the resonant frequency detection flow shown in FIG. 28 correspond to step S601 to step S608 of the frequency initial adjustment flow shown in FIG. 26. However, they differ on the point that while in the frequency initial adjustment flow (FIG. 26) the sensing portion 2a resonant frequency is searched within a range of ±10% of the standard frequency Fr, whereas in the resonant frequency detection flow (FIG. 28) the resonant frequency is searched within a range of ±3% of the current AC voltage frequency. I.e., as a second adjustment mode the frequency adjustment circuit 16d searches for the sensing portion 2a resonant frequency within a second frequency range which is narrower than the first frequency range and includes the frequency of the current AC voltage.

Here, in the frequency initial adjustment flow (FIG. 26), it is necessary to search for the resonant frequency responsive to individual differences between sensing portions 2a, model changes, etc. In this regard, based on the inventors' knowledge, it is sufficient for the resonant frequency detection flow (FIG. 28) to respond to post-frequency initial adjustment resonant frequency offsets, and the post-frequency initial adjustment resonant frequency are not greatly offset. Also, in the resonant frequency detection flow (FIG. 28), setting a narrow range for searching a resonant frequency can shorten the time required for resonant frequency searching.

Also, step S639 to step S642 of the resonant frequency detection flow shown in FIG. 28 correspond to step S609 to step S612 of the frequency initial adjustment flow shown in FIG. 26. I.e., the determining circuit 16f, which is achieved using the microcomputer 16, determines the success or failure of a frequency adjustment by the frequency adjustment circuit 16d. However, in a frequency initial adjustment flow (FIG. 26: first adjustment flow), when noise or the like is mixed into the detected data (steps S609, S610), or when the degree of reverberation vibration is insufficient (step S612), the flow chart was returned to the beginning and detection repeated. In contrast, in the resonant frequency detection flow (FIG. 28) executed as the second adjustment mode, in these cases (step S639, S640, S642) a determination of a "resonant frequency search failure" (step S645) is made without repeating the resonant frequency search, completing one iteration of the flow chart processing.

I.e., when there are items included for which the waveform does not monotonically diminish after completing the application of an AC voltage (step S640→S645), the determining circuit 16f determines that the frequency adjustment by the frequency adjustment circuit 16d failed. The determining circuit 16f also determines that frequency adjustment by the frequency adjustment circuit 16d has failed if the vibration energy of the sensing portion 2a after stopping the application of an AC voltage at the decided upon resonant frequency does not reach a predetermined threshold (step S642→S645). Thus when detection of a resonant frequency fails, the current AC voltage frequency is maintained.

Meanwhile if there has been a successful resonant frequency detection (step S643), the frequency selected in step S641 is set as the current resonant frequency of the sensing portion 2a (step S644), thus completing one iteration of the FIG. 28 flow chart. The resonant frequency set in this step S644 of FIG. 28 is compared in step S623 of the resonant frequency detection flow shown in FIG. 27 with the current frequency of the AC voltage applied to the piezo-electric element 4, which is then used to judge if there is a frequency offset.

Next, referring to FIG. 29, we explain the AC voltage frequency readjustment flow.

As described above, while the main flow (FIG. 23) is operating, the sensing portion 2a resonant frequency is detected and compared with the current AC voltage frequency, and a determination is made of whether there is a frequency offset (FIG. 23, step S406). However, as explained below, even when a frequency offset has been sensed, the AC voltage frequency will not be immediately changed to match the resonant frequency.

For example, if the sensing portion 2a resonant frequency has dropped due to adhesion of water droplets on the sensing portion 2a, then dropping or evaporation of the water droplets results in a relatively short time in the restoration of the resonant frequency to the original frequency. If the resonant frequency changes due to cold water or hot water impinging on the sensing portion 2a, the frequency returns in a relatively short time to the original frequency if the sensing portion 2a temperature returns to room temperature. For this reason, if the frequency of the AC voltage changes every time a resonant frequency change is sensed, the applied AC voltage frequency can become unstable, or the difference between the resonant frequency and the AC voltage frequency can actually increase due to the time lag. Thus in the present embodiment, as a result of the frequency readjustment flow, the AC voltage frequency (the drive frequency) is readjusted based on the how long the divergence between the resonant frequency and the AC voltage frequency has continued.

As described above, if a judgment is made that an offset exists between the sensing portion 2a resonant frequency and the current AC voltage frequency, a count is made of the time over which the frequency offset continues (FIG. 23, step S419). While this frequency offset is continuing, the AC voltage frequency readjustment flow shown in FIG. 29 is executed once a minute (FIG. 23, step S421).

First, in FIG. 29, step S651, the above-described resonant frequency detection flow (FIG. 28) is executed as a subroutine.

Next; in step S652, a judgment is made of whether detection of the resonant frequency executed in step S651 has succeeded. If it has succeeded, the system advances to step S635; if it has failed, the system advances to step S656.

In step S656, no readjustment of the frequency of the AC voltage applied to the piezo-electric element 4 (the drive frequency) is executed, and one iteration of the flow chart processing shown in FIG. 29 is completed with the current frequency maintained as is. I.e., when the AC voltage frequency is changed without obtaining a high reliability detection result in the resonant frequency detection; the AC voltage frequency in some cases actually drifts from the resonant frequency due to measurement error or the like.

Meanwhile if detection of a resonant frequency is successful, the system advances to step S653, where the frequency detected in step S651 and the frequency of the current AC voltage are compared. If the resonant frequency is lower than the AC voltage frequency, the system advances to step S655; if the resonant frequency is at or above the AC voltage frequency, the system advances to step S654.

In step S654, a judgment is made of whether the accumulated frequency offset continuous time is at or above 5 minutes, which is the frequency offset determination time. If the continuous time is 5 minutes or greater, the system advances to step S657; if not 5 minutes or greater, the system advances to step S656. In step S656, no readjustment of the frequency of the AC voltage 4 (the drive frequency) is executed, and one iteration of the flow chart processing shown in FIG. 29 is completed with the current frequency maintained as is. I.e., if the frequency offset has not continued for 5 minutes or greater, there is a potential that the resonant frequency will return to the original frequency by leaving the frequency offset alone.

Meanwhile, if the frequency offset continuation time is 5 minutes or greater, the system advances to step S657, and in step S657 the frequency of the AC voltage applied to the piezo-electric element 4 (the drive frequency) is changed (readjusted), and in step S651 is matched to the detected resonant frequency. Thus if the frequency offset between the resonant frequency and the AC voltage frequency is sensed by the frequency offset sensing circuit 16e, the frequency adjustment circuit 16d adjusts the AC voltage frequency (drive frequency) to match the resonant frequency. However a frequency adjustment by the frequency adjustment circuit 16d is executed when the state in which a frequency offset is sensed by the frequency offset sensing circuit 16e continues for a predetermined frequency offset determination time or greater.

On the other hand if the resonant frequency is lower than the AC voltage frequency, the system advances to step S655. In step S655, a judgment is made of whether the accumulated frequency offset continuous time is 30 minutes or greater, which is the frequency offset determination time. If the frequency offset continuous time is 30 minutes or greater, the system advances to step S657: if not 30 minutes or greater, the system advances to step S656. As described above, in step S656 no readjustment of the AC voltage frequency (drive frequency range) is executed. In step S657, the AC voltage frequency (drive frequency) is matched to the resonant frequency.

Thus in the present embodiment the frequency offset determination time differs when the resonant frequency is higher (step S654) or lower (step S655) than the AC voltage frequency; when the resonant frequency is lower than the AC voltage, a longer time is set for the frequency offset determining time. I.e., when the resonant frequency is lower than the AC voltage frequency (step S655), the highest probability state is the one in which water droplets adhere to the sensing portion 2a and the resonant frequency drops. On the other hand the highest probability state in which the resonant frequency is higher than the AC voltage frequency (step S654) is the one in which water droplets were adhered to the sensing portion 2a in the past, and the AC voltage frequency was lowered, following which the water droplet fells off or evaporated so that the resonant frequency rose.

Therefore when the resonant frequency is higher than the AC voltage frequency it is desirable to match the AC voltage frequency to the true resonant frequency as early as possible. By contrast, when the resonant frequency is lower than the AC voltage frequency, there is a high potential that the resonant frequency will gradually return to the AC voltage frequency due to the gradual dropping off or evaporation of water droplets, even if the frequency offset is neglected. Hence when the resonant frequency is lower than the AC voltage frequency, it is preferable to take a long frequency offset determination time and prevent the AC voltage frequency from becoming unstable.

The touch detection device of the third embodiment comprises a frequency offset sensing circuit 16e for sensing the occurrence of an offset between the sensing portion 2a resonant frequency and the frequency of the AC voltage applied to the piezo-electric element 4, whereby when a frequency offset is sensed by the frequency offset sensing circuit 16e, the frequency adjustment circuit 16d performs an adjustment so that the AC voltage frequency matches the resonant frequency of the sensing portion resonant frequency (FIG. 23, step S406→S419→S420→S421), so that frequency offsets can be monitored and the touch detection device constantly maintained in a favorable state.

Also, in the touch detection device of the present embodiment the frequency adjustment circuit 16d executes a frequency adjustment when frequency offset sensing by the frequency offset sensing circuit 16e has continued for a predetermined determination period or longer (FIG. 23, step S654→S657, and step S655→S657), therefore automatic adjustment by the frequency adjustment circuit 16d can be more reliably performed.

In addition, using the touch detection device of the present embodiment the frequency offset determination time is set to be longer when the sensing portion 2a resonant frequency is less than the frequency of the AC voltage applied to the piezo-electric element 4 (FIG. 29, step S653→S655) than when the sensing portion 2a resonant frequency is higher than the frequency of the AC voltage applied to the piezo-electric element 4 (FIG. 29, step S653→S654), therefore temporary changes in resonant frequency caused by the adhesion of water droplets can be effectively handled.

Also, using the touch detection of the present embodiment, in the first adjustment mode (FIG. 26) the resonant frequency is searched within a first frequency range (±10% of the standard frequency) which includes the sensing portion 2a standard frequency, and in the second adjustment mode (FIG. 28) the resonant frequency is searched within a second frequency range (±3% of the current AC voltage frequency) narrower than the first frequency range which includes the current AC voltage frequency, therefore adjustments responsive to the cause for the frequency offset can be executed in a short time.

Furthermore, in the touch detection device of the present embodiment, in the first adjustment mode (FIG. 26), if frequency adjustment has failed, a resonant frequency is repeatedly searched until succeeding (FIG. 26, step S609→S601, S610→S601, S612→S601); in the second adjustment mode (FIG. 28), if frequency adjustment has failed, searching for a resonant frequency is not repeated; the current AC voltage frequency is maintained (FIG. 28, step S639→S645, S640→S645, S642→S645), so an appropriate faucet apparatus 2 can be performed in response to the conditions producing the frequency offset, the touch detection device usage conditions, and so forth, and the goals of reliable frequency adjustment and the reduction of unusable time periods can both be achieved.

Also, using the touch detection device of the present embodiment, if the envelope detection waveform includes a waveform which does not monotonically diminish after application of an AC voltage is completed (lower portion of FIG. 31), a determination is made that frequency adjustment by the frequency adjustment circuit failed (FIG. 26, step S610, FIG. 2, step S640), so mistaken frequency adjustments caused by the effect of noise, etc. can be prevented).

Furthermore, using the touch detection device of the present embodiment, if the sensing portion 2a vibration energy does not reach a predetermined threshold value after stopping the application of an AC voltage at the decided-upon resonant frequency, a determination is made that frequency adjustment by the frequency adjustment circuit has failed (FIG. 26, step S612→S601: FIG. 28, step S642→S645), therefore mistaken frequency adjustments caused by frequency adjustments in an inappropriate environment can be avoided. For example, mistaken frequency adjustments can be avoided when a user touches a sensing portion 2a during execution of a frequency adjustment.

Also, using the touch detection device of the present embodiment, an AC voltage at a confirming frequency different from the normal AC voltage frequency (FIG. 25, steps S541, S543) is applied to the piezo-electric element 4 as a contact determination confirming operation (FIG. 25); if target object contact is also determined by the contact determination circuit 16a through the application of this confirming frequency AC voltage, then the determination of contact with the sensing portion 2a is fixed. Thus even if a mistaken determination of target object contact is made by the contact determination circuit 16a due to a frequency offset, the contact determination confirming circuit 16b performs an excitation using an AC voltage at a confirming frequency different from the normal AC voltage frequency, so that even if the resonant frequency is offset, a large reverberation vibration is excited as the confirming frequency approaches the resonant frequency, and false sensing due to frequency offsets can be effectively suppressed.

We have explained preferred embodiments of the invention above, but other variations may also be added to the above-described embodiments. In particular, in the above-described embodiments the present invention was applied to the detection of switching between spouting and shutting off of a faucet apparatus, but the present invention may also be applied to the detection of switching between spouting forms (shower spouting, straight spouting, etc.), or to freely selected operations such as flow volume adjustment, temperature adjustment, and the like. In the present embodiment the touch detection device was applied to a faucet apparatus to which a spouting portion is affixed, but the touch detection device may also be applied to a pull-out type faucet apparatus in which the spouting head can be pulled out. In such cases, a signal line can be built along a hose pulled out from the faucet apparatus main body, and a sensing portion disposed at the end of the spouting head can be electrically connected to a detection circuit disposed on the bottom side of a counter board. Also, in the present embodiment the touch detection device was applied to a faucet apparatus, but the present invention may also be applied to any desired water handling equipment, such as a water spout apparatus, a flow adjustment apparatus, a temperature adjustment apparatus, or an apparatus combining these.

In the above-described embodiments a piezo-electric element was used as a vibration excitation element, but any element or device capable of exciting vibration in the sensing portion may be used as the vibration excitation element. In the above-described embodiments, reverberation vibration was detected by a piezo-electric element after exciting a vibration in the sensing portion using a piezo-electric element, but it is also possible to provide an element or device for detecting reverberation vibration in the sensing portion separate from the element or device used to excite vibration. Also, in the above-described embodiments an AC voltage was applied to one terminal of a piezo-electric and a signal for detecting reverberation vibration was acquired from that same terminal, but it is also possible to separately provide a reverberation vibration detection terminal on the piezo-electric or the vibration excitation element, separate from the terminal for applying an AC voltage.

Also, in the above-described embodiments the frequency of the AC voltage applied to the piezo-electric element was matched to the resonant frequency of the sensing portion and piezo-electric element vibrating as a single integral piece, but the AC voltage frequency does not have to match the resonant frequency. I.e., even if these frequencies differ, the reverberation vibration is smaller when the sensing portion is not touched than when it is touched, therefore in principle a touch can be detected based on reverberation vibration. Also, in the above-described present embodiment AC voltage was directly applied to the piezo-electric element by switching two transistors, but it is also possible to apply an AC voltage to a piezo-electric element through a boost transistor or a capacitor, etc.

EXPLANATION OF REFERENCE NUMERALS

1: faucet apparatus in a first embodiment of the invention
2: faucet main body
2a: sensing portion
2b: spout opening
4: piezo-electric element (vibration excitation element)
4a, 4b: signal lines
6: hot/cold mixing valve
8a: hot water electromagnetic valve (on-off valve)
8a: cold water electromagnetic valve (on-off valve)
10: faucet controller
12: detection circuit
14a: hot water supply pipe
14b: cold water supply pipe
16: microcomputer
16a: contact determination circuit
16b: contact determination confirming circuit
16c: anomaly sensing circuit
16d: frequency adjustment circuit
16e: frequency offset sensing circuit
16f: determining circuit
18: drive circuit
18a: PNP transistor
18b: NPN transistor
18c, 18d: resistors
20: signal conversion circuit
20a, 20b: capacitors
20c: diode 20d: resistor
22: voltage divider circuit
22a, 22b: resistors

The invention claimed is:

1. A touch detection device used in water handling equipment, comprising:
   a sensing portion for sensing contact with a target object;
   a vibration excitation element attached to the sensing portion;
   a drive circuit for exciting a vibration in the sensing portion by intermittently applying an AC voltage at a predetermined frequency to the vibration excitation element; and
   a contact determination circuit configured to determine whether the target object has contacted the sensing portion based on vibration of the sensing portion after application of the AC voltage to the vibration excitation element by the drive circuit;
   wherein the vibration excitation element comprises a piezo-electric element, and the contact determination circuit determines whether the target object has contacted the sensing portion based on an output signal from the vibration excitation element detected after stopping of the application of the AC voltage to the vibration excitation element;
   wherein the vibration excitation element comprises an input terminal to which the AC voltage is applied by the drive circuit, the output signal from the vibration excitation element is obtained from the input terminal of the vibration excitation element, and the output of the drive circuit becomes high impedance after application of the AC voltage stops; and
   wherein the contact determination circuit is configured to determine whether or not the target object has contacted the sensing portion based on a total of a plurality of voltage value acquired from the output signal of the vibration excitation element detected after the stopping of the application of the AC voltage by the drive circuit, and the contact determination circuit determines that the target object has made contact when the total is at or below a predetermined threshold value.

2. The touch detection device of claim 1, further comprising a contact determination confirming circuit, wherein after the determination has first been made by the contact determination circuit that the target object has made contact, the contact determination confirming circuit performs a contact determination confirming operation to further reduce the possibility of false sensing.

3. The touch detection device of claim 2, wherein once the contact by the target object has first been determined by the contact determination circuit, the contact determination confirming circuit performs the contact determination confirming operation in which the AC voltage at a confirming frequency different from the normal frequency of the AC voltage is applied, and the contact determination confirming circuit fixes the judgment of contact with the sensing portion when the contact of the target object is also determined by the contact determination circuit by applying the AC voltage at the confirming frequency.

4. A faucet apparatus for switching between water spouting and shut off by a touch operation, comprising:
   the touch detection device of claim 1;
   an operating portion including the sensing portion; and
   an on-off valve for opening and closing based on a determination of contact by the target object with the sensing portion performed by the touch detection device.

5. A touch detection device used in water handling equipment, comprising:
   a sensing portion for sensing contact with a target object;
   a vibration excitation element attached to the sensing portion;
   a drive circuit for exciting a vibration in the sensing portion by intermittently applying an AC voltage at a predetermined frequency to the vibration excitation element; and
   a contact determination circuit configured to determine whether the target object has contacted the sensing portion based on vibration of the sensing portion after application of the AC voltage to the vibration excitation element by the drive circuit;
   wherein the vibration excitation element comprises a piezo-electric element, and the contact determination circuit determines whether the target object has contacted the sensing portion based on an output signal from the vibration excitation element detected after stopping of the application of the AC voltage to the vibration excitation element;
   wherein the vibration excitation element comprises an input terminal to which the AC voltage is applied by the drive circuit, the output signal from the vibration excitation element is obtained from the input terminal of the vibration excitation element, and the output of the drive circuit becomes high impedance after application of the AC voltage stops; and
   wherein the contact determination circuit comprises an anomaly sensing circuit configured to prevent false sensing, and the anomaly sensing circuit senses an anomaly based on the output signal from the vibration excitation element detected during application of the AC voltage to the vibration excitation element.

6. The touch detection device of claim 5, wherein the anomaly sensing circuit senses the anomaly when the amplitude of the output signal detected during application of the AC voltage is larger than the amplitude in normal operations, and the contact determination circuit does not determine the contact of the target object when the anomaly has been sensed.

7. The touch detection device of claim 5, wherein during application of the AC voltage to the vibration excitation element, the anomaly sensing circuit is configured to sense an anomaly when fluctuations in the amplitude of the output signal exceed a predetermined level, and the contact determination circuit does not determine the contact of the target object when the anomaly has been sensed.

8. A touch detection device used in water handling equipment, comprising:
   a sensing portion for sensing contact with a target object;
   a vibration excitation element attached to the sensing portion;
   a drive circuit for exciting a vibration in the sensing portion by intermittently applying an AC voltage at a predetermined frequency to the vibration excitation element;
   a contact determination circuit configured to determine whether the target object has contacted the sensing portion based on vibration of the sensing portion after application of the AC voltage to the vibration excitation element by the drive circuit; and
   a frequency adjustment circuit configured to adjust the frequency of the AC voltage applied to the vibration excitation element wherein the frequency adjustment circuit adjusts the frequency of the AC voltage to a resonant frequency of the sensing portion, to which the vibration excitation element is attached;

wherein the vibration excitation element comprises a piezo-electric element, and the contact determination circuit determines whether the target object has contacted the sensing portion based on an output signal from the vibration excitation element detected after stopping of the application of the AC voltage to the vibration excitation element;

wherein the vibration excitation element comprises an input terminal to which the AC voltage is applied by the drive circuit, the output signal from the vibration excitation element is obtained from the input terminal of the vibration excitation element, and the output of the drive circuit becomes high impedance after application of the AC voltage stops; and wherein the frequency adjustment circuit applies the AC voltage for a predetermined period multiple times at different frequencies, and the frequency at which the amplitude of the output signal from the vibration excitation element is maximal following the stopping of the AC voltage application, is determined by the frequency adjustment circuit to be the mechanical resonant frequency of the sensing portion, to which the vibration excitation element is attached.

9. The touch detection device of claim 8, wherein when there are multiple frequencies at which the amplitude of the output signal detected after application of the AC voltage, is maximized, then among the frequencies at which amplitude is maximized, the frequency at which amplitude fluctuations of the output signal are smallest during application of the AC voltage to the vibration excitation element, is determined by the frequency adjustment circuit to be the resonant frequency of the sensing portion, to which the vibration excitation element is attached.

10. The touch detection device of claim 8, further comprising a frequency offset sensing circuit configured to sense the occurrence of a frequency offset between the resonant frequency of the sensing portion and the frequency of the AC voltage applied to the vibration excitation element; wherein when the frequency offset is sensed by the frequency offset sensing circuit, the frequency adjustment circuit performs an adjustment so that the frequency of the AC voltage matches the resonant frequency of the sensing portion.

11. The touch detection device of claim 10, wherein the frequency adjustment circuit adjusts the frequency when the frequency offset sensed by the frequency offset sensing circuit is continuously present for a predetermined frequency offset determination time or greater.

12. The touch detection device of claim 11, wherein when the resonant frequency of the sensing portion is below the frequency of the AC voltage applied to the vibration excitation element, the frequency offset determination time is set to be longer than when the resonant frequency of the sensing portion is above the frequency of the AC voltage applied to the vibration excitation element.

13. The touch detection device of claim 10, wherein the frequency adjustment circuit is constituted to search for the resonant frequency of the sensing portion within a predetermined frequency range, and to be capable of executing a first adjustment mode and a second adjustment mode between which different search frequency ranges are used, wherein in the first adjustment mode the resonant frequency is searched within a first frequency range which includes a standard frequency of the sensing portion, and in the second adjustment mode the resonant frequency is searched within a second frequency range narrower than the first frequency range, which includes the current frequency of the AC voltage.

14. The touch detection device of claim 13, further comprising a determination circuit configured to determine whether a frequency adjustment by the frequency adjustment circuit has succeeded; wherein in the first adjustment mode, when the determination circuit determines that the frequency adjustment has failed, the resonant frequency is repeatedly searched until the frequency adjustment succeeds, while in the second adjustment mode, when the determination circuit determines that the frequency adjustment has failed, the frequency of the current AC voltage is maintained without repeatedly searching for the resonant frequency.

15. The touch detection device of claim 14, wherein the frequency adjustment circuit is constituted for applying AC voltages to the vibration excitation element at multiple frequencies within the predetermined frequency range, respectively obtaining output signals from the vibration excitation element for each application of an AC voltage, and performing the frequency adjustment by analyzing envelope detection waveforms of these output signals, while the determination circuit determines that the frequency adjustment by the frequency adjustment circuit has failed when the envelope detection waveforms include a waveform which does not decrease monotonically after application of the AC voltage.

16. The touch detection device of claim 14, wherein the frequency adjustment circuit is constituted to apply the AC voltage to the vibration excitation element at multiple frequencies within the predetermined frequency range, to acquire output signals from the vibration excitation element when each AC voltage is applied, to search for the resonant frequency based on these output signals, and then to make a determination, while the determination circuit determines that the frequency adjustment by the frequency adjustment circuit has failed when a vibration energy of the sensing portion detected after the AC voltage at the determined resonant frequency is applied, does not reach a predetermined threshold value.

* * * * *